(12) United States Patent
Mizuno et al.

(10) Patent No.: US 8,957,968 B2
(45) Date of Patent: Feb. 17, 2015

(54) MONITORING SYSTEM

(75) Inventors: Yoshiro Mizuno, Tokyo (JP); Hiroshi Kurita, Kanagawa (JP)

(73) Assignee: Yoshiro Mizuno, Tokyo (JP)

( * ) Notice: Subject to any disclaimer, the term of this patent is extended or adjusted under 35 U.S.C. 154(b) by 497 days.

(21) Appl. No.: 13/498,567

(22) PCT Filed: Sep. 28, 2010

(86) PCT No.: PCT/JP2010/066873
§ 371 (c)(1),
(2), (4) Date: Jul. 11, 2012

(87) PCT Pub. No.: WO2011/037266
PCT Pub. Date: Mar. 31, 2011

(65) Prior Publication Data
US 2012/0268597 A1 Oct. 25, 2012

(30) Foreign Application Priority Data

Sep. 28, 2009 (JP) ................................. 2009-222909
Oct. 29, 2009 (JP) ................................. 2009-248431

(51) Int. Cl.
*H04N 7/18* (2006.01)
*G06Q 50/22* (2012.01)
*G06Q 10/06* (2012.01)

(52) U.S. Cl.
CPC ............... *G06Q 50/22* (2013.01); *G06Q 10/06* (2013.01)
USPC ............. 348/143; 348/64; 348/180; 348/161; 348/94; 340/572.1; 340/572.4; 235/380

(58) Field of Classification Search
USPC ........................ 348/143, 161, 180, 64, 63, 94; 340/572.1, 572.4, 572.2, 995.22; 235/375, 380
See application file for complete search history.

(56) References Cited

U.S. PATENT DOCUMENTS

| 7,522,051 | B2 * | 4/2009 | Sanari et al. ............... 340/572.1 |
| 8,181,865 | B2 * | 5/2012 | Daily ............................ 235/383 |
| 2006/0267770 | A1 | 11/2006 | Sanari et al. | |
| 2008/0251575 | A1 | 10/2008 | Bowling et al. | |

FOREIGN PATENT DOCUMENTS

| JP | 2003-281157 | 10/2003 |
| JP | 2007-151001 | 6/2007 |
| JP | 2007-164718 | 6/2007 |
| JP | 2007-260390 | 10/2007 |
| WO | 01/46923 A1 | 6/2001 |

OTHER PUBLICATIONS

Extended European Search Report Issued Jun. 30, 2014.

* cited by examiner

*Primary Examiner* — Jefferey Harold
*Assistant Examiner* — Jean W Desir
(74) *Attorney, Agent, or Firm* — K&L Gates LLP; Louis C. Cullman; Michelle Glasky Bergman

(57) ABSTRACT

To construct a system composed as described hereafter, capable of easily calling out monitoring data from a monitoring system, where task information along with index information is a key, and for which tracking by a task system is desired, by linking the index information of the monitoring data managed by the index information of the task information and monitoring system, with the storage location, and which is composed of a first and second type work area where tasks are performed, a monitoring system server, a monitoring data storage device, monitoring objects, a task system server, and a task data storage device.

17 Claims, 73 Drawing Sheets

FIG. 8

| RECEIVED FIXED ID | INITIAL RECEPTION | | EFFECTIVE DEADLINE | GROUP ID | |
|---|---|---|---|---|---|
| | DATE | TIME | | | |
| k1 | 20091023 | 10:22 | 13:22 | g1 | ⎫ 8001 |
| k2 | 20091023 | 11:07 | 14:17 | g2 | |
| k3 | 20091023 | 11:30 | 14:30 | g3 | |
| k4 | 20091023 | 12:33 | 15:33 | g4 | |
| k5 | 20091023 | 13:01 | 16:01 | g5 | |
| k6 | 20091023 | 13:55 | 16:55 | g6 | |
| k7 | 20091023 | 14:11 | 17:11 | g7 | ⎫ 8002 |
| k1 | 20091023 | 15:11 | 18:11 | g8 | |

FIG. 13

| RECEIVED FIXED ID | INITIAL RECEPTION || EFFECTIVE DEADLINE | USE FREQUENCY |
|---|---|---|---|---|
| | DATE | TIME | | |
| k1 | 20091023 | 10:22 | 13:22 | 1 |
| k2 | 20091023 | 11:07 | 14:17 | 1 |
| k3 | 20091023 | 11:30 | 14:30 | 1 |
| k4 | 20091023 | 12:33 | 15:33 | 1 |
| k5 | 20091023 | 13:01 | 16:01 | 1 |
| k6 | 20091023 | 13:55 | 16:55 | 1 |
| k7 | 20091023 | 14:11 | 17:11 | 1 |
| k1 | 20091023 | 15:11 | 18:11 | 2 |

FIG. 16

| RECEIVED FIXED ID | INITIAL RECEPTION DATE | TIME | EFFECTIVE DEADLINE | GROUP ID | URI |
|---|---|---|---|---|---|
| k1 | 20091023 | 10:22 | 13:22 | g1 | http//www.drug.com/trace.exe?ID=g1 |
| k2 | 20091023 | 11:07 | 14:17 | g2 | http//www.drug.com/trace.exe?ID=g2 |
| k3 | 20091023 | 11:30 | 14:30 | g3 | http//www.drug.com/trace.exe?ID=g3 |
| k4 | 20091023 | 12:33 | 15:33 | g4 | http//www.drug.com/trace.exe?ID=g4 |
| k5 | 20091023 | 13:01 | 16:01 | g5 | http//www.drug.com/trace.exe?ID=g5 |
| k6 | 20091023 | 13:55 | 16:55 | g6 | http//www.drug.com/trace.exe?ID=g6 |
| k7 | 20091023 | 14:11 | 17:11 | g7 | http//www.drug.com/trace.exe?ID=g7 |
| k1 | 20091023 | 15:11 | 18:11 | g8 | http//www.drug.com/trace.exe?ID=g8 |

FIG. 21

```
                                  ─── 21000
┌──────────────────────────────────────────────────────────────┐
│                          ── 21001                            │
│   GROUP ID:    ┌──────┐                                      │
│                │  g1  │                                      │
│                └──────┘                                      │
│                                                              │
│    ACTION      LOCATION (CAMERA)    PHOTOGRAPHY COMMENCEMENT DATE/TIME │
│                                                              │
│  RECEPTION         C1                  20091023  10:07 ── 21002 │
│  PRESCRIPTION      C2                  20091023  10:17       │
│  PRESCRIPTION      M2                  20091023  10:19       │
│   DELIVERY         C3                  20091023  10:31 ── 21003 │
│   DELIVERY         M3                  20091023  10:32       │
│  ACCOUNTING        C4                  20091023  10:42       │
│                                                              │
└──────────────────────────────────────────────────────────────┘
```

FIG. 30

| RECEIVED TAG ID | INITIAL RECEPTION | | EFFECTIVE DEADLINE | GROUP ID | |
|---|---|---|---|---|---|
| | DATE | TIME | | | |
| k1 | 20091023 | 10:22 | 13:22 | g1 | ⎫ 30001 |
| k2 | 20091023 | 11:07 | 14:17 | g2 | |
| k3 | 20091023 | 11:30 | 14:30 | g3 | |
| k4 | 20091023 | 12:33 | 15:33 | g4 | |
| k5 | 20091023 | 13:01 | 16:01 | g5 | |
| k6 | 20091023 | 13:55 | 16:55 | g6 | |
| k7 | 20091023 | 14:11 | 17:11 | g7 | ⎫ 30002 |
| k1 | 20091023 | 15:11 | 18:11 | g8 | |

FIG. 34

| WRITTEN INFORMATION | TAG ID |
|---|---|
| A | k1 |
| B | k2 |
| C | k3 |
| D | k4 |
| E | k5 |
| F | k6 |
| G | k7 |
| H | k8 |

FIG. 35

```
                                    ─3500
                        ─3501
TAG ID:       K1

GROUP           PHOTOGRAPHY COMMENCEMENT DATE/TIME
                                                     ─3502
          G1                    20091023 10:22
                                                     ─3503
          G8                    20091023 15:11
```

(FRONT SURFACE)　　(REAR SURFACE)

— 4402  (MONITORING DATA)

| TEMPORARY ID | UNIQUE ID | DATE | TIME | LOCATION | MONITORING INFORMATION | GROUP ID |

— 4403

— 4404  (MONITORING DATA)

| TEMPORARY ID | UNIQUE ID | DATE | TIME | LOCATION | MONITORING INFORMATION |

— 4405

| GROUP | MONITORING DATA BELONGING TO GROUP ||||
|---|---|---|---|---|
| | TEMPORARY ID | DATE | TIME | LOCATION |
| $g^1$ | 200910230922 | 1023 | 10:22 | RECEIVED |
| | 200910230922 | 1023 | 10:32 | PRESCRIBED |
| | 200910230922 | 1023 | 10:35 | DELIVERY |
| | 200910230922 | 1023 | 10:45 | ACCOUNTING |

FIG. 45

| RECEIVED TEMPORARY ID | INITIAL RECEPTION DATE | TIME | EFFECTIVE DEADLINE | GROUP ID | |
|---|---|---|---|---|---|
| 200910230922 | 20091023 | 10:22 | 13:22 | g1 | ⎤ 45001 |
| 200910230923 | 20091023 | 11:07 | 14:17 | g2 | |
| 200910230924 | 20091023 | 11:30 | 14:30 | g3 | |
| 200910230925 | 20091023 | 12:33 | 15:33 | g4 | |
| 200910230926 | 20091023 | 13:01 | 16:01 | g5 | |
| 200910230927 | 20091023 | 13:55 | 16:55 | g6 | |
| 200910230928 | 20091023 | 14:11 | 17:11 | g7 | ⎤ 45002 |
| 200910230922 | 20091023 | 15:11 | 18:11 | g8 | |

FIG. 49

| TEMPORARY ID | UNIQUE ID |
|---|---|
| 200910231022 | 10000000k1 |
| 200910231023 | 10000000k2 |
| 200910231024 | 10000000k3 |
| 200910231025 | 10000000k4 |
| 200910231026 | 10000000k5 |
| 200910231027 | 10000000k6 |

FIG. 54

```
                              ─5400
                         ─5401
PRESCRIPTION ID:   10000000K1

GROUP          PHOTOGRAPHY COMMENCEMENT DATE/TIME
                                                    ─5402
          J1                    20091001  11:45
                                                    ─5403
          G1                    20091023  10:22
```

FIG. 55

```
                                    ─5500
                           ─5501
    GROUP ID:     G1

ACTION    LOCATION (CAMERA)   PHOTOGRAPHY COMMENCEMENT DATE/TIME

RECEPTION      C1              20091023 10:22  ─5502
    PRESCRIPTION   C2              20091023 10:27
    PRESCRIPTION   M2              20091023 10:29
    DELIVERY       C3              20091023 10:35  ─5503
    DELIVERY       M3              20091023 10:37
    ACCOUNTING     C4              20091023 10:45
```

FIG. 64

| RECEIVED MEMBER NUMBER | INITIAL RECEPTION | | EFFECTIVE DEADLINE | GROUP ID | |
|---|---|---|---|---|---|
| | DATE | TIME | | | 64001 |
| 20091022k1 | 20091023 | 10:22 | 13:22 | g1 | |
| 20091022k2 | 20091023 | 11:07 | 14:17 | g2 | |
| 20091022k3 | 20091023 | 11:30 | 14:30 | g3 | |
| 20091022k4 | 20091023 | 12:33 | 15:33 | g4 | |
| 20090922j1 | 20091023 | 13:01 | 16:01 | g5 | |
| 20090716j1 | 20091023 | 13:55 | 16:55 | g6 | |
| 20090927k3 | 20091023 | 14:11 | 17:11 | g7 | 64002 |
| 20091022k1 | 20091023 | 15:11 | 18:11 | g8 | |

FIG. 70

```
                                    ┌──── 7000
                             ┌─── 7001
MEMBER NUMBER:  │  20091022K1  │

GROUP          PHOTOGRAPHY COMMENCEMENT DATE/TIME
                                                        ┌──── 7002
               G8                  20091023  15:11
                                                        ┌──── 7003
               G1                  20091023  10:22
```

FIG. 71

```
                              ┌─── 7100
┌─────────────────────────────────────────────────────┐
│                    ┌─── 7101                         │
│  GROUP ID:    │ G1 │                                 │
│               └────┘                                 │
│                                                      │
│   ACTION      LOCATION (CAMERA)   PHOTOGRAPHY COMMENCEMENT DATE/TIME │
│                                                      │
│  RECEPTION        C1              20091023  10:22 ── 7102 │
│  PRESCRIPTION     C2              20091023  10:27    │
│  PRESCRIPTION     M2              20091023  10:29    │
│  DELIVERY         C3              20091023  10:35 ── 7103 │
│  DELIVERY         M3              20091023  10:37    │
│  ACCOUNTING       C4              20091023  10:45    │
│                                                      │
└──────────────────────────────────────────────────────┘
```

MONITORING SYSTEM

CROSS REFERENCE TO RELATED APPLICATIONS

The present application is a National Stage of International Application No. PCT/JP2010/066873 filed on Sep. 28, 2010, which claims priority to Japanese Patent Application No. 2009-248431, filed in the Japanese Patent Office on Oct. 29, 2009, and Japanese Patent Application No. 2009-222909, filed in the Japanese Patent Office on Sep. 28, 2009, the entire contents of which are being incorporated herein by reference.

BACKGROUND

A system which monitors tasks with a video camera is used in various tasks with the objective of preventing the occurrence of task related incidents or offenses.

However, conventional monitoring systems simply use a video camera to photograph and record a work area in which a task is progressing or being performed. Owing to this, if blemishes in products relating to task incidents or tasks are discovered, attempting to trace the cause or scope of the blemish requires time to search the related images from a huge amount of video data. This has made it difficult to realize a high degree of traceability.

Technology for realizing traceability is disclosed in Patent Literature 1. Here, monitoring of the monitoring system is controlled by detecting the RFID (Radio Frequency Identification) moving in accompaniment with the task workflow. However, ID information for linking task data relating to monitoring must be read into the RFID tag prior to commencing a task. Therefore, the operation is a hindrance when introducing a monitoring system.

In addition, for each task in each work area, a link is established with the task data controlled by the monitoring data and task system, and where there are multiple work areas, there is a need to establish a relationship with the task data for each image storage of a task in the respective areas. Also, following the progress of task flow, it would be difficult to establish a link with the photographed image data through ID information. Owing to this, establishing a link for each task data is burdensome, and an obstacle to the introduction of a monitoring system.

Furthermore, if an adequate number of RFID tags are not prepared, among the tasks for each day, since there is a need to put the RFID tags to use, monitoring data becomes mixed in relation to different tasks relative to single ID information, and there are cases of an excessive tracking burden. Owing to this, it has been difficult to realize a high degree of traceability.

Patent Literature 1: Japanese Patent No. 4276654.

Providing an image monitoring system which realizes such high traceability is the problem of the present invention.

First of all, the problem is to collect and efficiently retrieve data relating to tasks which are the object of tracking by grouping monitored data relating to one or prescribed task and increasing their visibility by manifesting the retrieval results in task groups.

In addition, there is also the problem of making it possible to directly call monitoring data relating to the task from data items included in a task system or register.

Furthermore, in introducing a monitoring system, there is also the problem of realization of linking to task data and monitoring data without adding the entry of a data item for newly linking to task systems relating to the execution of tasks which are the subject of monitoring. This is because it would be undesirable to obscure the management responsibilities of the task system manager.

There is also the problem of suppressing and keeping the amount of labor during a task to a minimum, and activating a monitoring system without making burdensome the task of the operation of the monitoring system.

Also, in such medical institutions as pharmacies compounding medicine and the like, in handling medical supplies, there is also the problem of linking with visual data which manages image information with a monitoring system which uses a magnifying glass introduced to monitor tasks in which large medical errors may occur, even if there are no great visual differences.

SUMMARY

The monitoring system relating to the first aspect of the present invention, provided with one or multiple motion picture or still picture devices, wherein:

tasks for each of one or multiple work areas is established so as to be provided within photographic parameters, connection is made to a network, a trigger signal is received which provides notification of the timing of a task, the progress of the task is continuously photographed, and the photographed image information is transmitted to a specific transmission destination; and, included as compositional elements are, 1) an RFID tag which is added to something supplied to the task,
2) an RFID reader which transmits a trigger signal in a specific format to the photographic device connected to the network, and, the detection area of the RFID tag is set so as to detect an RFID tag which is located on the standard position that is assumed corresponding to the nature of the task accomplished in the work area, the detection area of the RFID tag is set so as to provide the position, and upon detecting the RFID tag, the tag ID which stores the RFID tag is read out, and the initial/termination timing of the task is extracted from a specific detection/non-detection pattern of the RFID tag, and
3) a monitoring system server connected to the network, which receives the image information, and creates index information which at least includes the tag ID, stored as monitoring data related to the image information; a specific effective deadline being set from the point in time at which the tag ID is initially read out,
and monitoring data which hold the same tag ID acquired within the effective deadline as index information are recognized as the task sequence group relating to a single task, and the monitoring data are retrieved for each group.

The tag ID stored in the RFID tag is a read-only fixed ID; the fixed ID is input to the input means attached to a task system which performs input relating to the execution of the task, and by adding the fixed ID to the index information of the task data handled by the task system, the monitoring data and the task data may be linked.

By making such a composition, there is no need to enter ID information to the RFID tag for each task, effectively greatly lightening the task burden.

The tag ID stored in the RFID tag is a read-only fixed ID; and upon inputting the fixed ID to the input means attached to a task system which performs input relating to the execution of a task, and by adding a URI which shows the storage location of the task sequence/group holding the fixed ID as index information to the index information of a task handled by the task system, the monitoring data and the task data may also be linked.

Making such a composition effectively performs a browser display of monitoring data which calls monitoring data relating to task data currently being handled through the WEB from a task system, as pages recorded in a specific format such as HTML and the like, without arranging for separate retrieval from a database.

A reference table is attached which calls out the corresponding tag ID from written information in which written information corresponding to the tag ID stored in the RFID tag is displayed on items supplied to the task, and a reference table is provided which calls out the corresponding tag ID from the written information. By inputting written information transcribed to a ledger or prescription as a retrieval key, monitoring data may also be retrieved.

Such a composition effectively suppresses the amount of labor within a task to a minimum, simplifying the introduction of a monitoring system.

Written information corresponding to a tag ID stored in the RFID tag is displayed on items supplied to the task, and a reference table is provided which reads out the corresponding tag ID from the written information, and upon inputting the written information to an input means provided in the task system which performs input relating to the execution of the task, by adding a URI which shows the storage location of the task sequence/group's monitoring data holding the tag ID corresponding to the written information as index information, to the index information of task data handled by the task system, the task data and monitoring data are linked.

Prior to commencing a task, the temporary ID is entered to the RFID tag, and at the time of detection/entry by the RFID reader/writer attached to the monitoring system after task commencement, a unique ID which has been allocated to each task is entered to the RFID tag, and index information which includes the temporary ID may be rewritten to index information including the unique ID.

The RFID tag is a component of a membership card storing the membership number, and index information including the membership number has a relationship established with the image information, and is stored in the monitoring system server as monitoring data, and by providing a reference table in which a relationship is established between the unique ID which the task system has pre-allocated to a task and the membership number, monitoring data may be directly retrieved relating to a task from the task data while being handled by the task system connected to the monitoring system server.

By such a composition, data items for linking to the task system are newly established, effectively realizing a link between the task data and the monitoring data by providing a common key for the member number without the need to make an entry.

The unique ID may also be the prescription ID of a prescription relating to a task.

The items provided to the task may also be at least one selected from an operation indication sheet, document holder, or tray.

The task system may also be at least one chosen from among a compounding system, a receptor system, or accounting system which manages compounding tasks in a pharmacy.

When adding a fixed ID to the index information, and by further adding the use frequency of the fixed ID, when monitoring data is retrieved which belongs to the frequency task sequence/group, relative to a single fixed ID, it may also be specified in the monitoring data of one task sequence group by referring to the item value relating to the use frequency of a fixed ID in the task data and the monitoring data, When calling the monitoring data linked from the task data during handling by the task system, in the case of retrieving the monitoring data belonging to multiple task/sequence groups relative to a fixed ID included in task data index information, the monitoring data of task data information may also be specified with reference to other data items.

The input means is an RFID reader wherein, if the RFID tag is placed within detection parameters, the tag ID stored by the RFID tag is read out, and the action of linking the task data of a task being handled by the task system, with the monitoring data is executed.

By inputting the information as a retrieval key, in the case of retrieving monitoring data of a task sequence group, the monitoring data of a task sequence group may also be specified with reference to other data items.

Aforesaid task data, as data items, may also include prescribed ID, patient name, date, time received, and prescription content.

Aforesaid monitoring data, as data items, may also include tag IDs, date, time, location of photographic device, image information, and task sequence/group ID.

Aforesaid monitoring data includes image information obtained by means of a magnifying glass used for task in a working area in which it is attached; the magnified image information is received, and index information is generated which includes aforesaid tag ID during detection in the work area, with which a relationship is then established with the magnified image information, and may be stored as monitoring data in aforesaid monitoring system server.

By making such a composition, even if the external appearance of such as medical supplies is not very different, tasks which include large medical errors and accidents are then efficiently monitored, and high traceability can be effectively realized.

Additional features and advantages of the present invention are described herein, and will be apparent from, the following Detailed Description and the Figures.

BRIEF DESCRIPTION OF THE FIGURES

FIG. 8 is a diagram showing the composition of an effective deadline table.

FIG. 13 is a diagram showing the composition of a use frequency reference table.

FIG. 16 is a diagram showing the composition of a storage location management table.

FIG. 21 is a diagram showing an initially displayed screen.

FIG. 30 is a diagram showing the composition of an effective deadline table.

FIG. 34 is a diagram showing a reference table.

FIG. 35 is a diagram showing an initially displayed screen.

FIG. 44 is a summary diagram which compares grouped formats.

FIG. 45 is a diagram showing the composition of an effective deadline table.

FIG. 49 is a diagram showing a unique ID reference table.

FIG. 54 is a diagram showing an initially displayed screen.

FIG. 55 is a diagram showing a detailed display screen of grouped monitoring data.

FIG. 64 is a diagram showing the composition of an effective deadline table.

FIG. 70 is a diagram showing the initially displayed screen.

FIG. 71 is a diagram showing a detailed display screen of grouped monitoring data.

DETAILED DESCRIPTION

The present disclosure relates to a monitoring system wherein the monitoring system monitors tasks using a photographic device, and particularly relates to a monitoring system which groups and manages monitoring data, and to a monitoring system linked to a task system relating to the execution of tasks becoming the monitoring object of the monitoring system.

Embodiment 1

(Entry Format of Fixed IDs Into a Task System)

Figure 1:
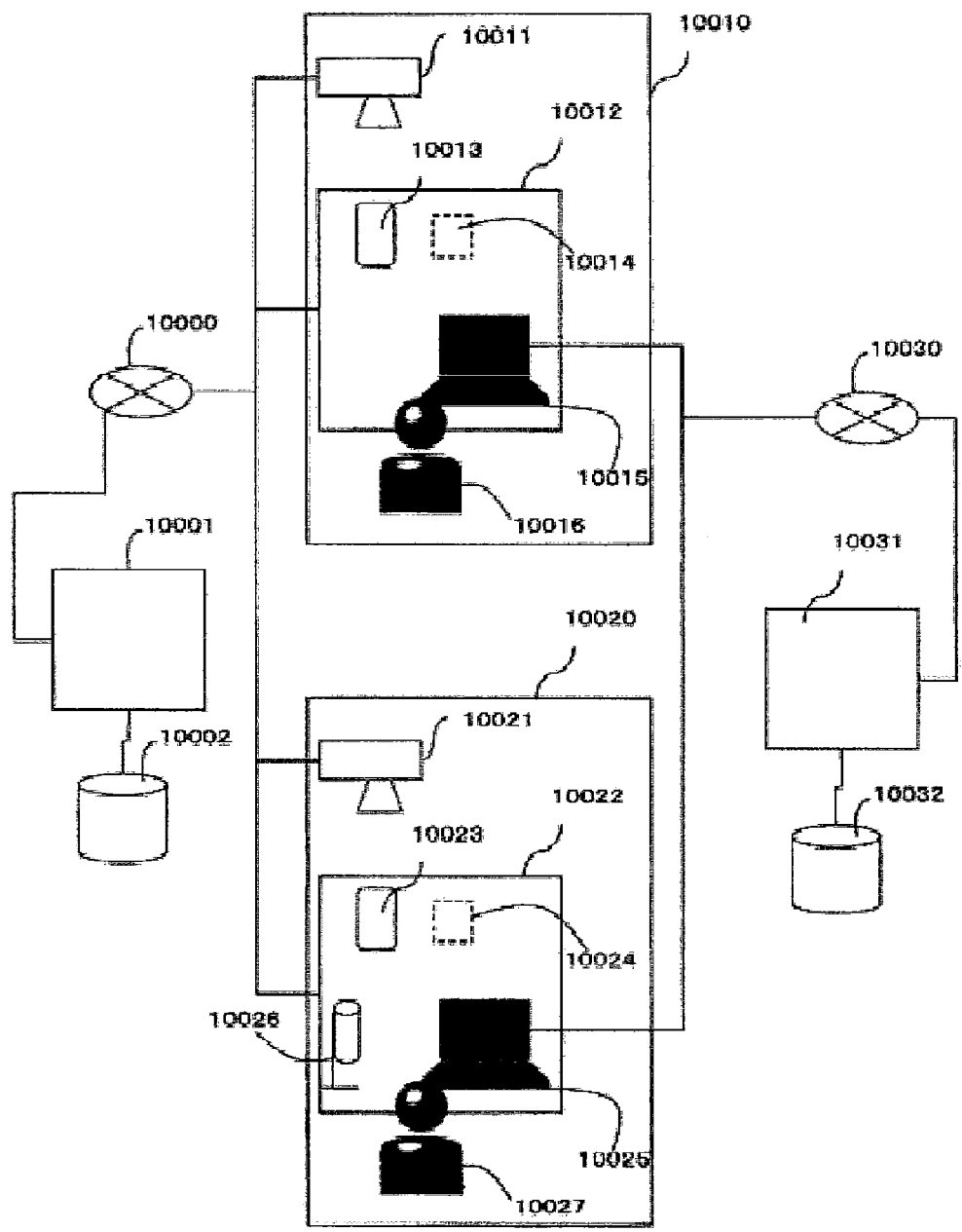
FIG. 1 is a summary composition diagram of the monitoring system relating to embodiment 1.

FIG. 1 is a summary composition diagram of the monitoring system relating to Embodiment 1 of the present invention. This is an embodiment form of a case of introducing reception in a pharmacy, a prescription location, a delivery location, and accounting to a system. This system is composed of a first type of work area 10010, a second type of work area 10020, a network 10030, a task system server 10031, and a task data storage device 10032 in which tasks are accomplished of a network 10000, a monitoring system server 10001, a monitoring data storage device 10002, and tasks comprising the monitoring object.

Here, conveniently, two networks 10000, and 10030 are shown in the drawings, however, this is actually one network or a mutually connected substantially single network.

In addition, in this instance, conveniently explained two types of work areas are shown one at a time. The first type of work area 10010 is adopted as the reception location or accounting location, since the second type of work. 10020 is adopted as the prescription area and delivery area, these respective types of work areas exist as a total of four work areas shown two at a time. Furthermore, the work areas of the present invention are not limited to being two at a time for each type, but are composed such that appropriate selection may be made of one or two types of work area constructions corresponding to the introduced pharmacy, scale of operation location, or the number of work areas, and there may be either only one type or multiple types of work areas.

First of all, the composition of a first type of work area is as follows. A monitoring camera 10011, and workbench 10012 are arranged, and tasks on the workbench 10012 by an operator 10016 are photographed. Here, to the workbench 10012 is attached an RFID reader 10013, managed by the monitoring system server through the network. Also, a document holder 10014 which has an RFID tag used in the detection area task is arranged, and the RFID reader 10013 transmits a specific trigger signal. The operator performs tasks relating to compounding medicine, and provides task input to the personal computer terminal 10015 connected to the task system server via the network.

Next, the composition of the second type work area is as follows. A monitoring camera 10021 and a workbench 10022 are arranged, and the operator 10027 photographs task accomplished facing the workbench using the monitoring camera 10021.

Here, to the workbench 10022 is attached an RFID reader 10023 and a magnifying glass 10026. Also, a document holder 10024 is arranged which has an RFID tag used with tasks in the detection area of the RFID reader, and the RFID reader 10023 transmits a specific trigger signal. The magnifying glass 10026 is network connected, and the operator 10027 sets the object in the photographic parameters of the magnifying glass or faces the magnifying glass toward the object, and by operating a switch (not shown in the drawing) acquires a magnified image. Here, the magnified image is transmitted to the monitoring system server via the network, while also being used in confirming the task object by the operator 10027, by means of a monitor and the like (not shown in the drawing). The operator 10027 performs tasks relating to compounding, and task input to the personal computer terminal 10025 connected to the task system server.

Here, an explicit explanation is not provided, in order to simplify the drawing, and the monitoring system server 10001 and task system server 10031 are connected to the network, making mutual access possible.

Furthermore, the composition of the system shown here is nothing more than an example, and an appropriate composition may be accomplished corresponding to the established object or specific hardware. For example, task input was made to a personal computer terminal, however, task input of the present invention is not limited to this. It is possible for it to be an appropriately dedicated terminal corresponding to the scale of the pharmacy.

In addition, the operation of each functional "unit" of the monitoring system server or task system server in the following explanation is executed by a personal computer or the computer of a workstation or the like provided with a prepared program and interface of a monitor, keyboard, and mouse and the like, and realized by controlling each type of device. These programs are recorded for example, on a readable recording medium with the hard disk, USB memory, CD-ROM, MO, and in DVD and the like of a computer, and executed by the operation of a system user.

Figure 2:
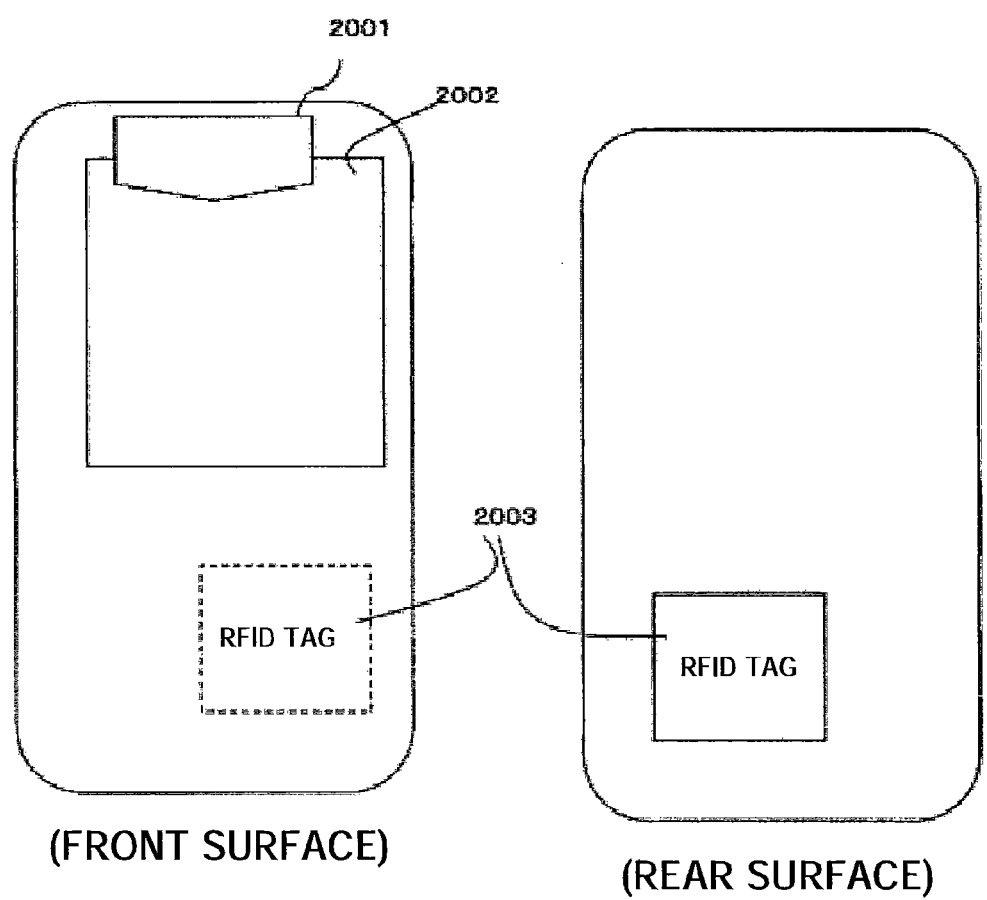
FIG. 2 is a compositional diagram of a document holder.

FIG. 2 is a diagram showing the composition of document holders 10014 and 10024 used by the present invention. 10014 and 10024 are prepared with one of the single tasks, by which a document is held of an operating manual or the like on which is recorded task operations, and which, along with the progress of the task, is transported to each work area. The operator, in the specific position of the workbench, performs tasks while referring to the indicated items held in the document holders 10014 and 10024. The document holders 10014 and 10024 are composed, for example, from a clip 2001 which holds the document, an operation instruction document 2002, and an RFID tag 2003. The RFID reader tag is detected upon placing the document holder on the workbench by means of RFID readers 10013 and 10023 provided on the workbench. The RFID readers 10013 and 10023 detect the progress of the task by means of detection/non-detection patterns, and image information of the sequence of task progress is acquired by transmitting a trigger signal to operate the monitoring camera. Control of the monitoring camera is already known, and recorded in Patent Literature 1. For example, while continuing detection of the RFID tag from the time of commencement of the operation T 1 to the time of completion of the operation T 2, the RFID tag continues transmission of a trigger signal relative to the monitoring camera, and photography is continued while the monitoring camera receives the trigger signal. Or, upon detecting the RFID tag at the time of commencement T 1, the RFID reader transmits an activation signal relative to the monitoring camera. Next, if detection ceases at the time of termination T 2, the RFID reader may also transmit a termination signal.

Figure 3:
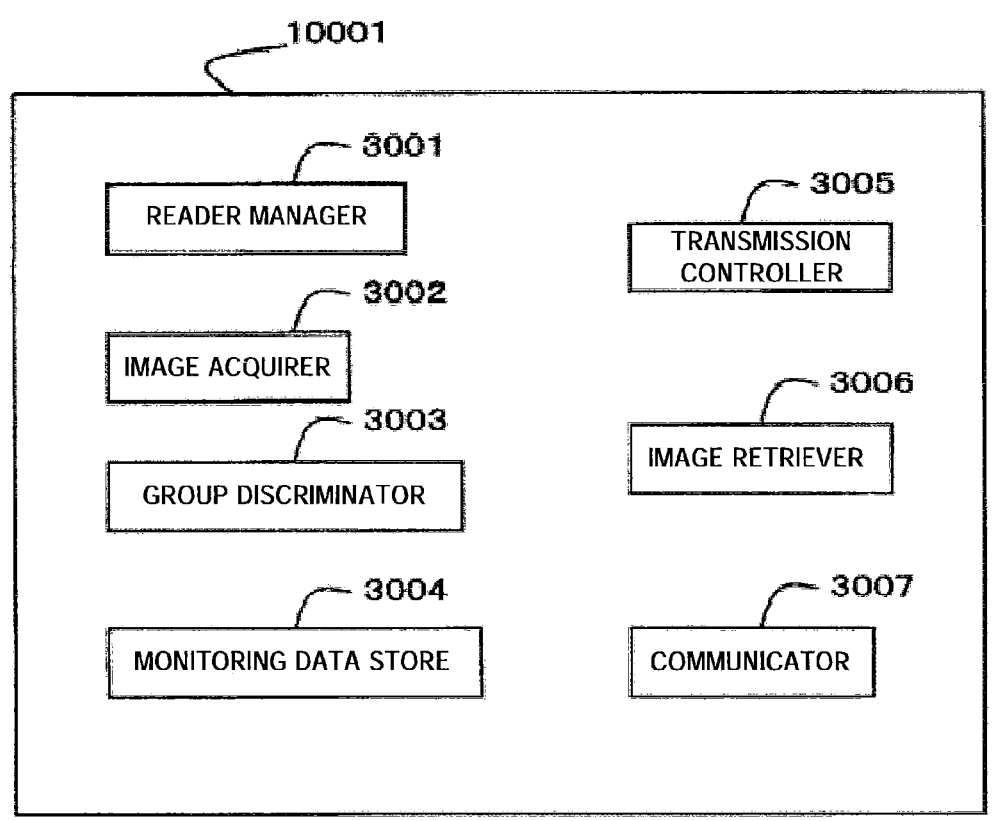
FIG. 3 is a diagram showing the internal composition of a monitoring system server.

FIG. 3 is a diagram showing the internal composition of the monitoring system server 10001 of the present invention. Monitoring system server 10001 is composed from a reader manager 3001 which manages detection of the RFID reader, the acquisition of image information transmitted from the monitoring camera, an image acquirer 3002 which creates/applies and stores index information, a group discriminator 3003 which discriminates task sequence/groups, a monitoring data store 3004 which stores monitoring data in a specific location, the creation of transmission information from specific index information, a transmission controller 3005 which transmits to the task system server 10031, an image retriever 3006 which receives the input of specific key information and calls out monitoring data, and a communicator 3007 which controls the communication operation of the network for the operation of each of the functional units. Here, the monitoring data is composed from information read from the detected RFID tag, the date, time, and index information created from information of the monitoring camera location and the like, and image information from the monitoring camera. The monitoring camera, depending upon whether acquisition has been accomplished within the period of the specific deadline from the initial detection of the RFID tag, and after/depending upon whether discrimination has been accomplished of what belongs to a single task sequence group, applies a specific group ID. Here, adoption is made of a terminal ID of the monitoring camera as the location of the monitoring camera; however, the location of the monitoring camera of the present invention is not limited to this, and it may also be, for example, the terminal ID of an RFID reader which transmits a trigger signal to activate the monitoring camera. In addition, the task sequence group, when patients come to the pharmacy, may be summarized as the understanding of a single sequence of all of the compounding tasks relating to prescriptions at the time (reception task, prescription task, delivery task, and accounting task).

Figure 4:
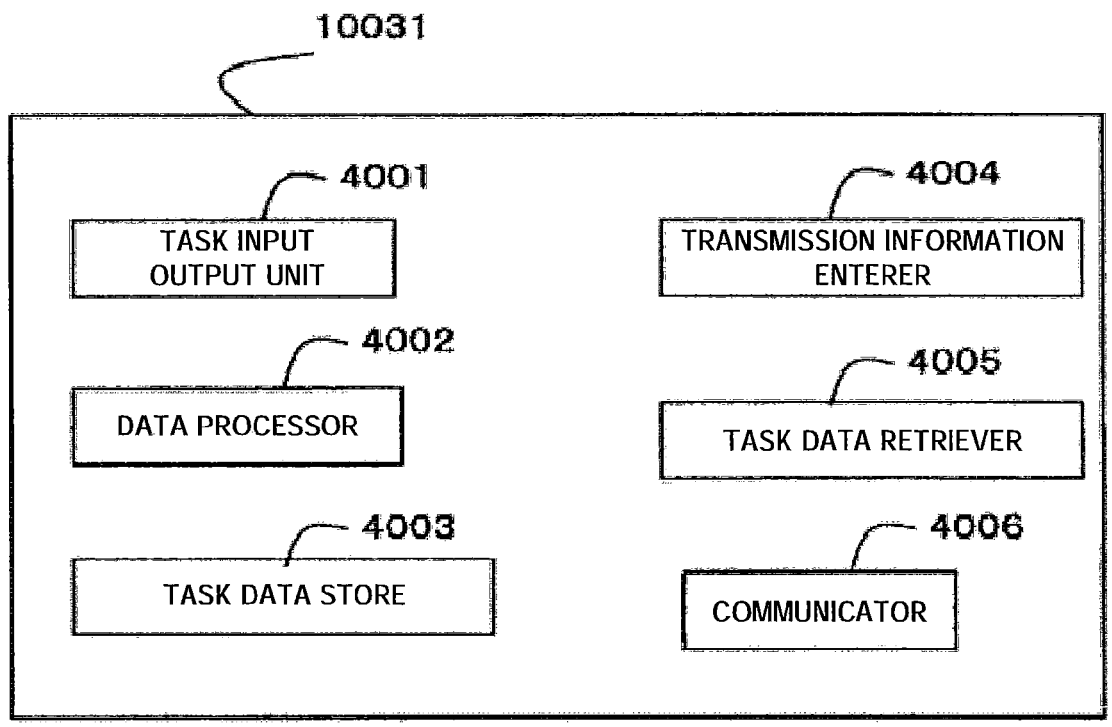
FIG. 4 is a diagram showing the internal composition of a task system server.

FIG. 4 is a diagram showing the internal composition of the task system server 10031 of the present invention. Task system server 10031 is composed from a data processor 4002 which processes input task information into the format of task data, a task data store 4003 which controls the storage of task data in the task data storage device 10032, a transmission information enterer 4004 which enters index information included in the transmission information into task data, a task data retriever 4005 which controls the retrieval of task data from specific key information input, and a communicator 4006 which controls the communications operation of the network for the operation of each functional unit. Here, the transmission information handled by the transmission information enterer 4004 monitors tasks relating to the task data during handling by the task system transmitted from the monitoring system server 10001, and is information which includes specific index information indicating the monitoring data. The index information, by means of the entry operation accomplished by the execution of the specific program is entered to pre-established items as index information of the task data. By making the entry information of the items to be a key in retrieval, it becomes capable to call out corresponding monitoring data, and establish a link between the monitoring data and the task data.

(Cooperative Action of Each Functional Unit in the Monitoring System Server)

Figure 5:
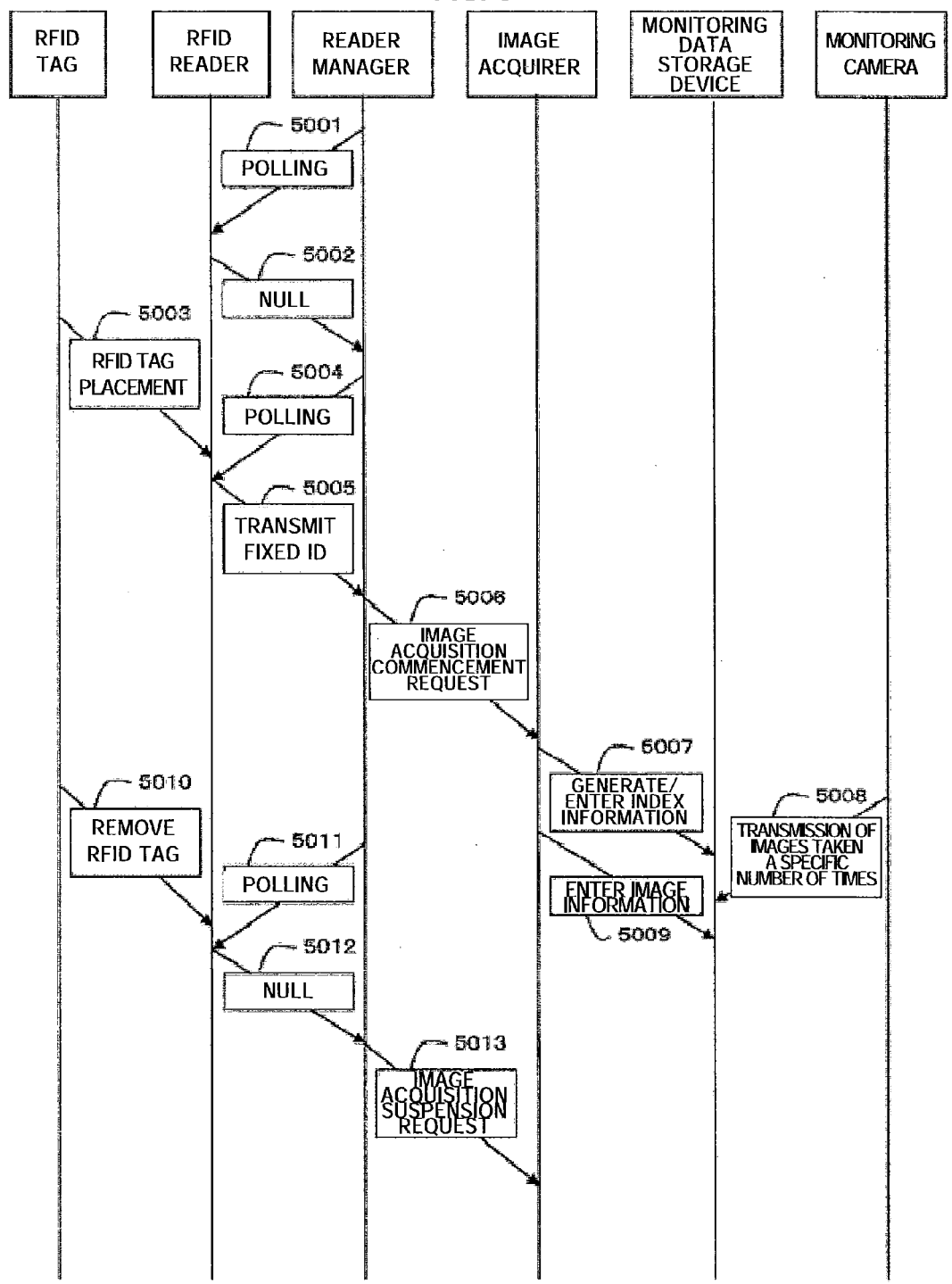
FIG. 5 is a sequence diagram showing the cooperative operation of each function/device.

Next, an explanation is provided concerning the process accomplished by the monitoring system server 10001. FIG. 5 is a sequence diagram showing the cooperative action by each functional unit/device of the reader manager and the like, showing image acquisition, creation of monitoring data, and storage action in the monitoring data storage device 10002.

First of all, in step 5001, polling is performed relative to the RFID reader by means of the action of the reader manager which executes a specific RFID reader management program. Here, if there is no transmission request, then in step 5002, a "Null" signal is returned. In step 5003, if the RFID tag is placed within specific detection parameters, then the specific ID of step 5005 is transmitted relative to the polling of step 5004. The fixed ID is a tag ID which had been pre-stored in the memory of the RFID tag.

The reader manager which received the transmission of the fixed ID, in step 5006, requests image acquisition relative to the image acquirer. The image acquirer, in step 5007, creates index information, and enters it to the monitoring storage device. The creation of the index information is explained hereafter.

In addition, the monitoring camera, in step 5008, transmits the image information of a specific amount to the monitoring data storage device. The image acquirer, in step 5009, enters the image information in the storage location of monitoring data into which the index information had been entered in the previous step. In step 5010, upon removal of the RFID tag from within the specific detection parameters, then in step 5012, "Null" is returned relative to the polling of step 5011.

The reader manager to which "Null" has been returned, in step 5013, transmits a request for the completion of image acquisition relative to the image acquirer.

(Creation of Index Information)

Figure 6:
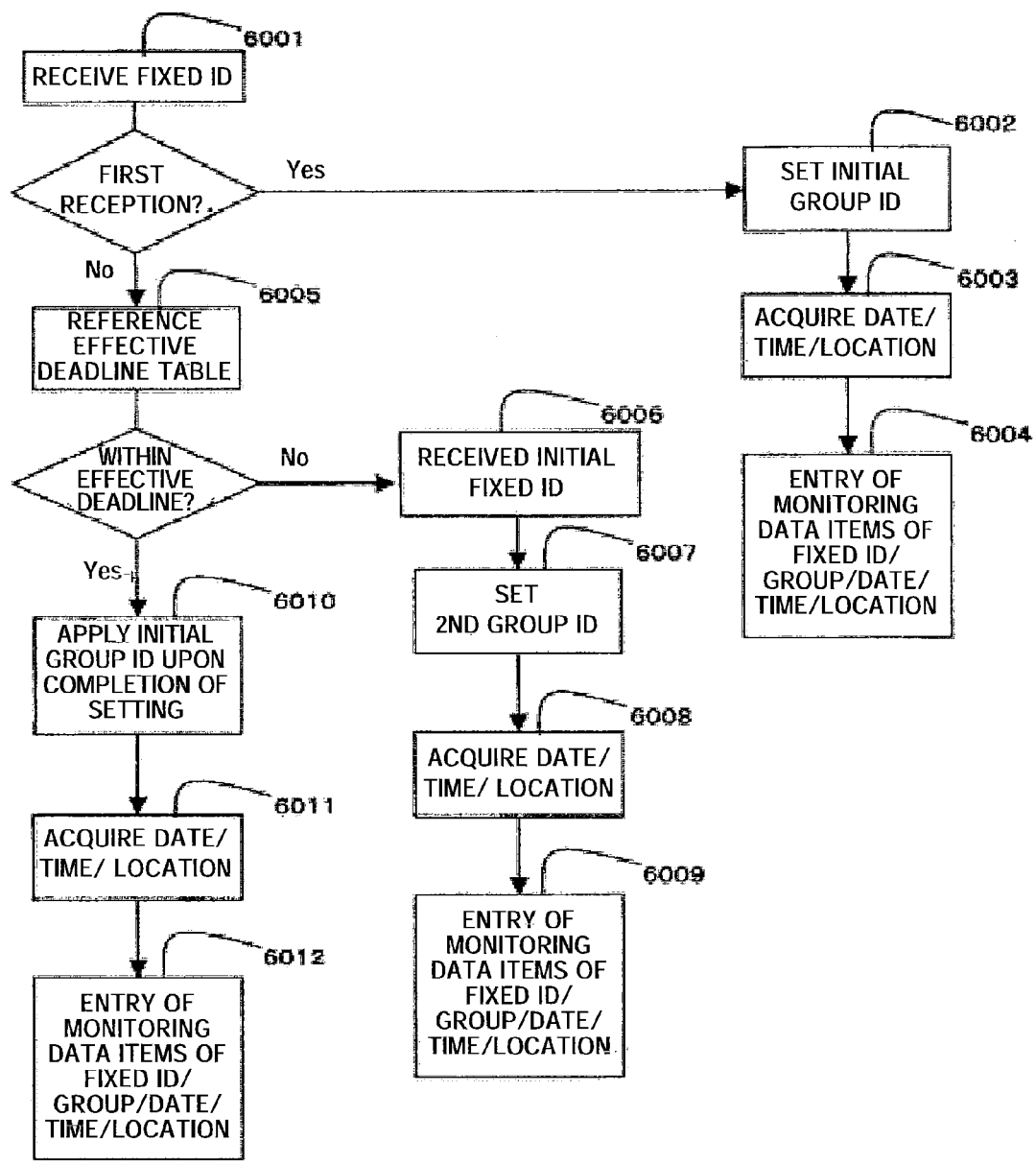
FIG. 6 is a flowchart which explains the operation of generation/entry of index information.

Next, an explanation is provided concerning the creation/entry method of index information. FIG. 6 is a flowchart for explaining the action of creation/entry of index information in step 5007 of FIG. 5.

First of all, in step 6001, the image acquirer received the fixed ID transmitted from the reader manager. Also, here, the image acquirer performs an inquiry of the monitoring data holding the fixed ID as index information relative to the monitoring data storage device, and makes a determination as to whether there has been an initial reception.

If the results of the determination is "Yes"; in other words, if there has been initial reception, the image acquirer sets the initial group ID in step 6002. Next, in step 6003, the image acquirer acquires information of date, time, and location relating to fixed ID detection. Here, information of the location is the terminal ID of the monitoring camera, by which terminal ID the work area is specific.

Furthermore, here, as the monitoring camera location, the terminal ID of the monitoring camera is adopted. However, the location of the monitoring camera of the present invention is not limited to this. For example, it may also be the RFID reader terminal ID which transmitted the trigger signal to activate the monitoring camera. Next, in step 6004, the image acquirer performs an entry to each item corresponding to the pre-established monitoring data of the set, acquired group ID, date, time, location and fixed ID.

On the other hand, when the results of discrimination are such that where the task sequence/group is already a fixed ID relating to the monitoring data which has already been set, in step 6005, the image acquirer refers to a specific effective deadline table. Also, the image acquirer discriminates as to whether or not a task is within the effective deadline. If not within the effective deadline, then in step 6006, the image acquirer receives an initial fixed ID, and in step 6007, already the group ID which is already been set establishes a different second group ID. Next, in step 6008, the image acquirer acquires date, time, and location information relating to the detection of the fixed ID. Also, in step 6009, the image acquirer enters the set or acquired group ID, date, time, location and fixed ID to each of the pre-established items corresponding to the monitoring data.

In step 6005, referring to the specific effective deadline table, if within the effective deadline, in step 6010, the image acquirer applies the already established first group ID. Next, in step 6011, the image acquirer acquires date, time, and location information relating to the detection of the fixed ID. Also, in step 6012, the image acquirer enters the applied or acquired group ID, date, time, location and fixed ID to each item corresponding to the pre-established monitoring data.

Furthermore, setting the group ID, a format establishing a group ID in each monitoring data was adopted. However, the invention relating to the task sequence/group of the present invention is not limited to this format, and monitoring data belonging to the same task sequence/group is registered in the management table established for each group, without establishing a data item relating to a group in the monitoring data, and a group management format would also be good.

Figure 7:
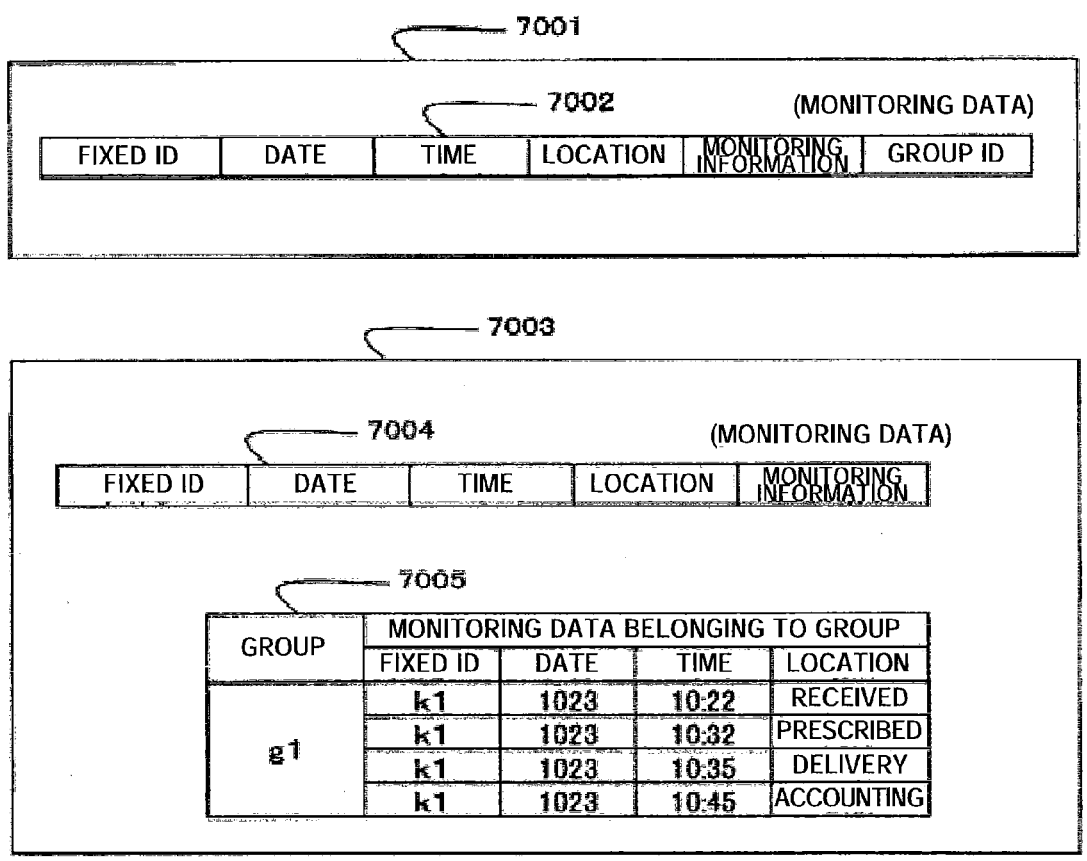
FIG. 7 is a summary diagram comparing the grouped formats.

FIG. 7 is a summary diagram which compares the grouped formats. Here, in step 6002 or step 6007 of FIG. 6, is shown an example of a method of establishing a group ID. Shown is monitoring data 7002 stored in the data storage device 7001, and monitoring data relating to the same task sequence is registered in management table 7003 without attaching a group ID, and a monitoring data storage device which stores monitoring data 7004 and 7005 without attaching a group ID item. Furthermore, the monitoring information is image information which has been acquired with a monitoring camera or image information which has been magnified by a magnifying glass.

(Effective Deadline Table)

FIG. 8 is a diagram which shows the composition of the effective deadline table referenced in step 6005 of FIG. 6. In this instance, it was effective for within three hours from the initial fixed ID reception. The table is appended each time the "initial fixed ID reception" is recognized. This item is composed from the received fixed ID, the date relating to initial reception, the time relating to the initial reception, the effective deadline, and the group ID. Referencing this table, the image acquirer applies the same group ID relative to the monitoring data relating to the same fixed ID within the effective deadline. Data shown in the effective deadline table 8001 and 8002 of FIG. 8 both have the fixed ID "k 1"; however, concerning monitoring data 7002 following the passage of the effective deadline of the task sequence of "g1", a different task sequence is recognized, and a second group ID "g8" is set which differs from the initial group ID "g1".

(Action Attaching a Link Between the Monitoring Data and the Task Data)

Figure 9:
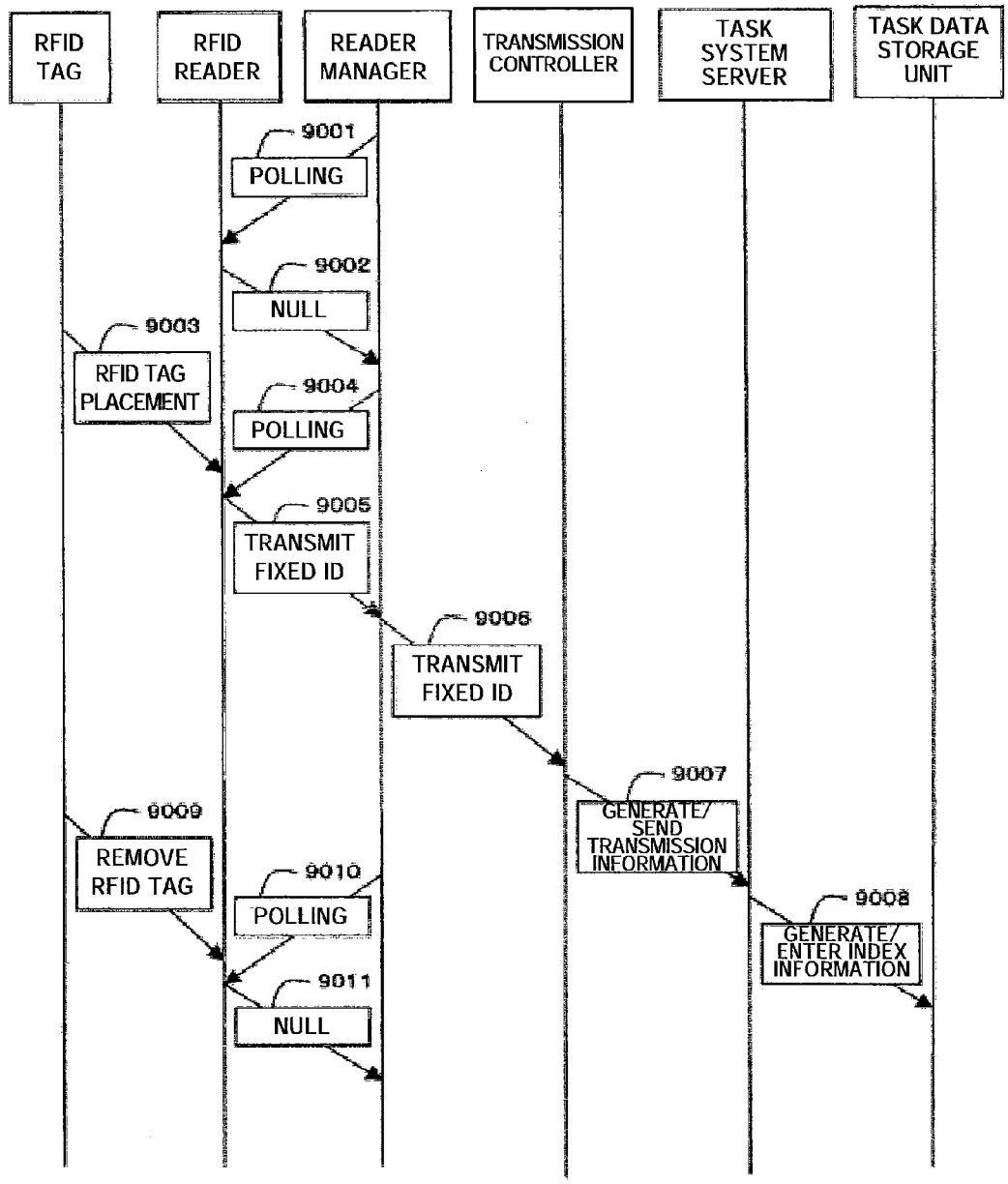
FIG. 9 is a sequence diagram showing the link attachment operation.

FIG. 9 is a sequence diagram showing the link attaching action which cooperates between the transmission controller 3005 of the monitoring system server and the transmission information enterer 4004 and the like of the task system server.

First of all, in step 9001, polling is performed relative to the RFID reader by the action of the reader manager which executes a specific RFID reader management program. Here, in the absence of a transmission request, in step 9002, a "Null" signal is returned. Next, in step 9003, upon placing the RFID tag within specific detection parameters, fixed ID transmission is performed of step 9005 relative to the polling of step 9004. The reader manager which received the fixed ID, in step 9006, transmits the fixed ID relative to the transmission controller. The transmission controller, in step 9007, generates transmission information, and sends it to the task system server. Here, as transmission information, corresponding to the need, if the received fixed ID is in a format in which it is transmitted as it is, there is a variation format transmitting the fixed ID and its use frequency and a variation format transmitting the storage location of the monitoring data relating to the received transmission information. An explanation will be provided hereafter concerning the respective formats, along with an explanation of the task system server.

In step 9008, the task system server provides entry to specific items of transmission information as items of the item of index information established in the task data currently being called out. This entry displays a specific execution button on the input screen of the task system, and as needed, a link attachment is provided with the monitoring data relating to the RFID tag which places the task data currently being called out within specific detection parameters, executed by adding the action of a click or the like on the execution button; but if while calling out the task data the RFID tag is set to within detection parameters, a format may also be provided in which the click action is automatically executed. Also, in step 9009, if the RFID tag is removed from the specific detection parameters, a "Null" signal is returned in step 9011 relative to the polling of step 901.

(Transmission Information Processing Action: Basic Format)

Figure 10:
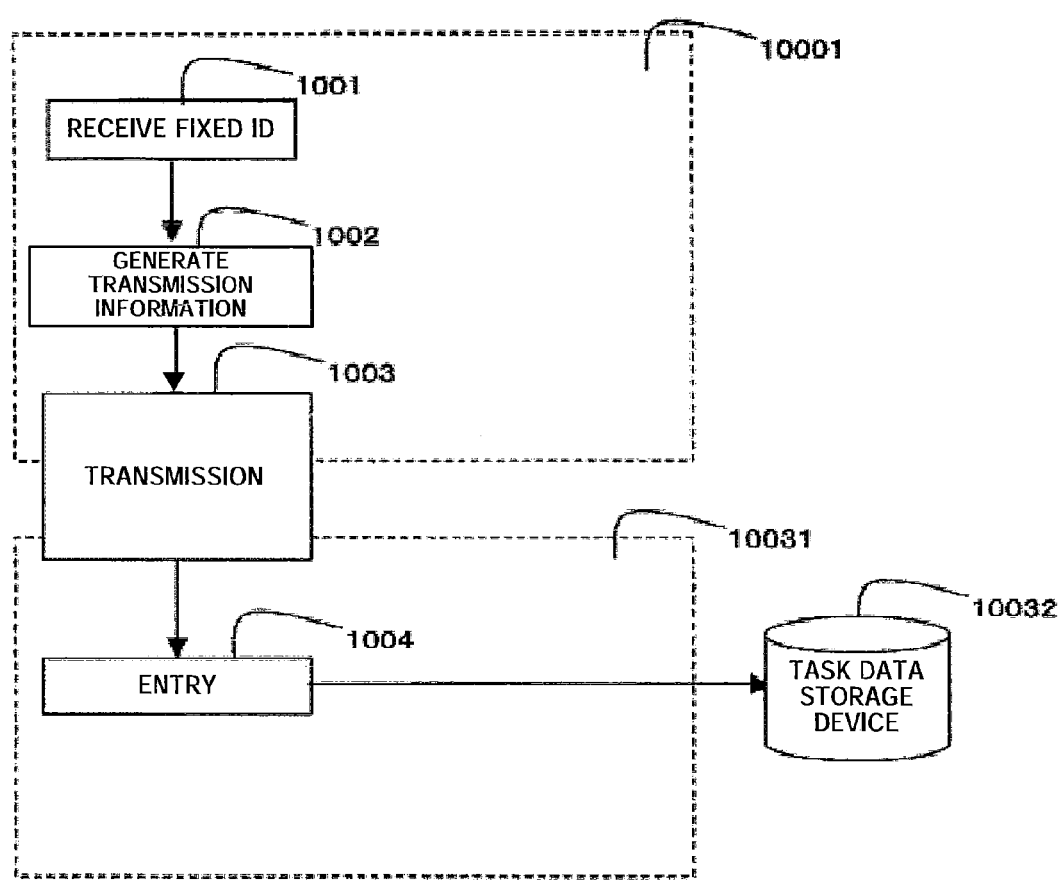
FIG. 10 is a flowchart showing the basic formula of cooperative operation in a monitoring system server.

FIG. 10 is a flowchart showing the basic format of cooperative action which performs the generation/transmission of transmission information in a monitoring system server, and reception of transmission information in a task system server, the creation of index information, and its entry to the task data storage device 10032.

Here, each step of the region 10001 shown by the broken line is an action of the monitoring server; and in addition, each step of the region 10031 shown by the broken line is an action of the task system server.

First of all, in step 1001, the monitoring system server is such that the transmission controller 3005 receives the fixed ID from the reader manager 3001. Next, in step 1002, the monitoring system server generates transmission information which includes the fixed ID. Also, in step 1003, the monitoring system server, by executing a specific transmission program of the transmission duty controller by adding the action of clicking the execution button, the transmission information is transmitted to the task system server. In step 1004, the task system server enters the fixed ID included in transmitted transmission information to the task data storage device 10032.

Figure 11:
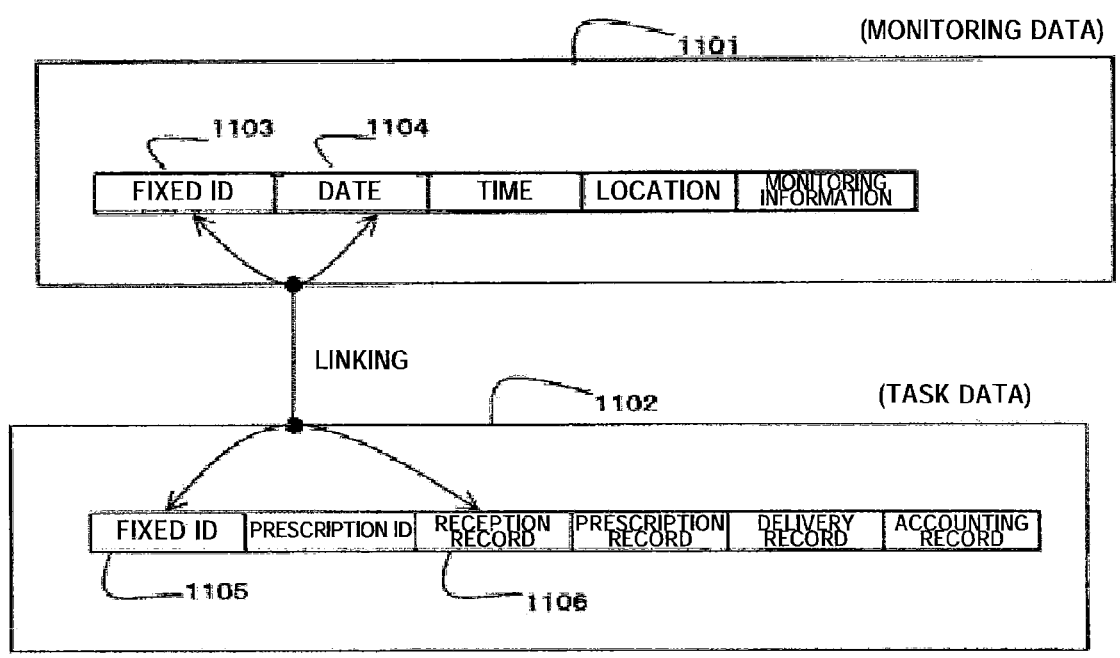
FIG. 11 is a diagram showing the composition of task data and monitoring data.

FIG. 11 is a diagram which, in step 1004 of FIG. 10, shows the composition of task data and monitoring data after completing the entry of a fixed ID. Monitoring data 1101 is composed from data items of fixed ID, date, time, location, and monitoring information. Here, the monitoring information is image information acquired by a monitoring camera. In addition, task data 1102 is composed from data items of a fixed ID, prescription ID, reception record, prescription record, delivery record, and accounting record. Here, the reception record and the like, conceptually suggest something related to task information, and establishes specific and practical items corresponding to essential tasks.

By establishing a correspondence between the data items with the fixed ID 1103 and the date1104 of monitoring data 1101 and the another data items with the fixed ID1105 and the reception record 1106 of task data 1102 so as to be used as the retrieval keys, a link can be established with the task data of a task relating to the monitoring data. In other words, the item values of the fixed ID items conform, and with the condition that a specific value of the value of the date item and the specific value of the reception record be within the parameters of the same task, it is determined to be (linked) monitoring data relating to the task, and an arrangement can be constructed which makes a call while referring to items going from data of one type to data of another type. Here, the use of fixed data and other items in establishing a link is a fixed ID without rewriting the tag ID in which is stored in the RFID tag, and a holder can be used to which an RFID tag is attached. Owing to this, after the elapse of a fixed period of time, since the same fixed ID is again received, there is a need for a link to be established in order to indicate the intention as to which task the monitoring data is related.

Here, the diagram has conveniently explained one monitoring data and task data, however, data handled by the present invention comprises bundles of multiple data, which also have attached links.

In addition, here, as other items of other than a fixed ID used in establishing a link, use was made of a date and reception record, however, the present invention is not limited to these, and appropriate selection may be made of time and reception records and the like.

(Transmission Information Processing Action in a Task System Server: Modification 1)

Figure 12:
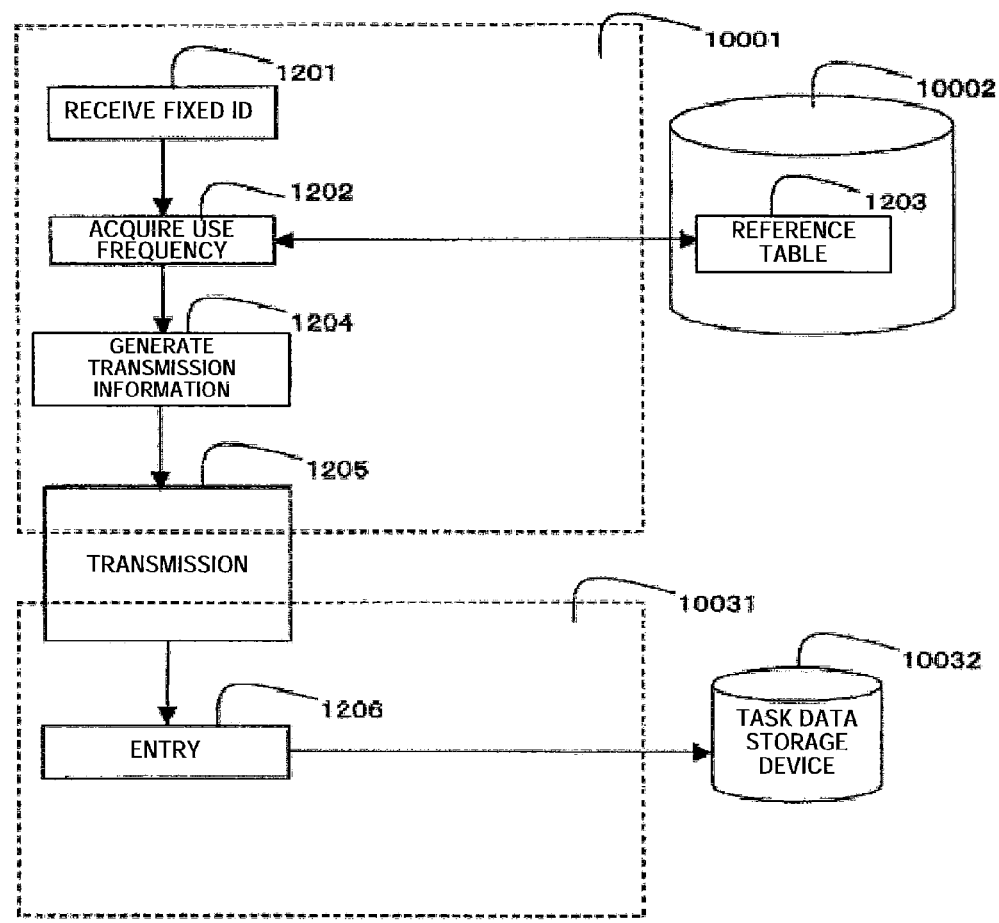
FIG. 12 is a flowchart showing the shape change 1 format of corporative operation in a monitoring system server.

FIG. 12 is a flow chart showing the modification 1 of cooperative action for creating/transmitting transmission information in a monitoring system server and for receiving the transmission of transmission information in a task system server, creating index information, and entering it in a task data storage device 10032.

Here, each step of the region 10001 shown by the broken line is an action of the monitoring system server, and each step of the region 10031 shown by the broken line is an action of the task system server.

First of all, in step 1201, the transmission controller 3005 receives the fixed ID from the reader manager 3001. Next, in step 1202, the monitoring system server refers to the use frequency reference table 1203, to acquire the fixed ID use frequency. The tag ID which stores the RFID tag is a fixed ID which is not rewritten, and since the document holder on which the RFID tag is attached is put to heavy use, after the passage of a fixed period of time, since the same fixed ID is received again, information showing the number of times and specifying which monitoring data relates to which task can be used as an index.

FIG. 13 shows the composition of the use frequency reference table 1203 referenced in step 1202. Here, there are also cases of validity within three hours from reception of the initial fixed ID. The use frequency reference table 1203 is a table posted for each recognition of the referenced "initial fixed ID reception". The use frequency reference table 1203 is composed from the received fixed ID, the date relating to initial reception, the time relating to initial reception, the effective deadline, and the frequency of use. Data shown in tables 1301 and 1302, along with the fixed ID "k 1", regarding the monitoring data following the passage of the effective time of the initial task sequence is recognized as a different task sequence, and the use frequency value becomes "2".

Next, the monitoring system server, in step 1204, creates transmission information which includes the fixed ID and use frequency, and in step 1205, by adding the action of clicking and the like on the execution button, a specific transmission gram of the transmission duty controller is executed. By this means, the transmission information is transmitted to the task system server. In step 1206, the task system server enters the fixed ID and use frequency included in the transmission information sent to the task data storage device 1032.

Figure 14:
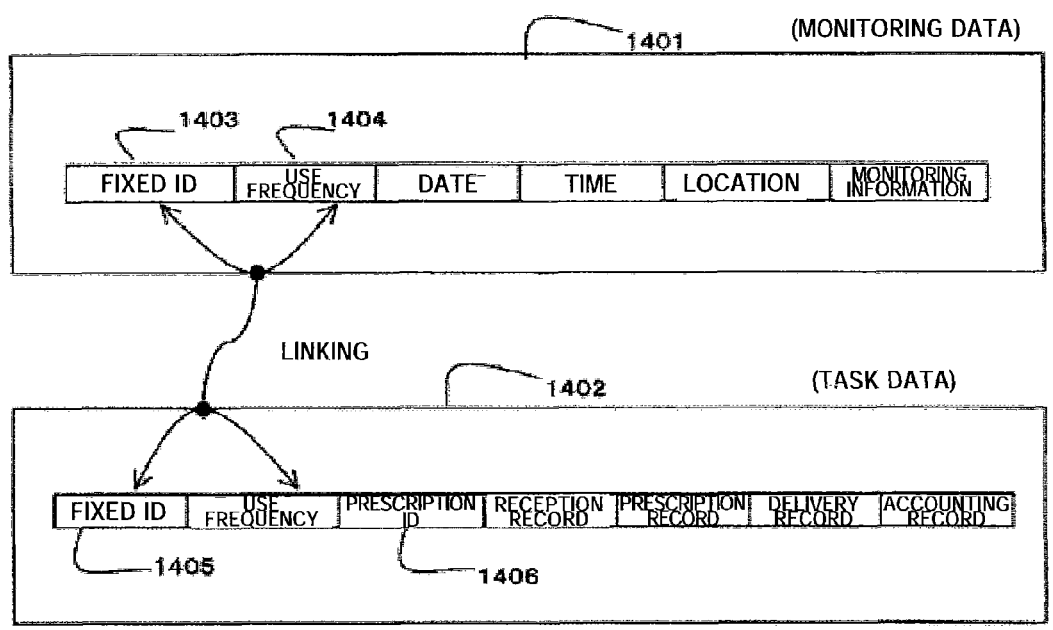
FIG. 14 is a diagram showing the composition of the task data and the monitoring data.

FIG. 14 is a diagram showing the composition of task data and monitoring data following the completion of the entry of FIG. 13 step 1206. The monitoring data 1401 is composed from the data items of fixed ID, use frequency, date, time, location, and monitoring information. Here, the monitoring information is image information acquired by the monitoring camera. Task data 1402 is composed from the data items of the fixed ID, use frequency, prescription ID, reception record, prescription record, delivery record, and accounting record. Here, the reception record and the like summarily suggest items relating to task information, established as detailed and practical items in accordance with the requirements of the task. Here, by referring to the item values relating to the monitoring data asked ID and use frequency, it is possible to directly call out the task data of tasks relating to monitoring data. In other words, by ' the item value of the fixed ID and use frequency as task data items, a link can be established to the monitoring data from the task data. Here, use is made of a fixed ID and other items in the link attachment comprising the fixed ID without rewriting the tag ID stored in the RFID tag, and since the document holder to which the RFID tag is attached is put to heavy use, the same fixed ID is again received after the passage of a fixed amount of time. Owing to this, in order to uniquely specify which task to which the monitoring data relates, it is necessary to attach a link in providing coordination with the other items.

Here, one monitoring data and task data have been conveniently shown in the drawing; however, data handled by the present invention comprises a bundling of multiple data, for which there is an attached linkage.

(Transmission Information Processing Action in a Task System Server: Modification 2)

Figure 15:
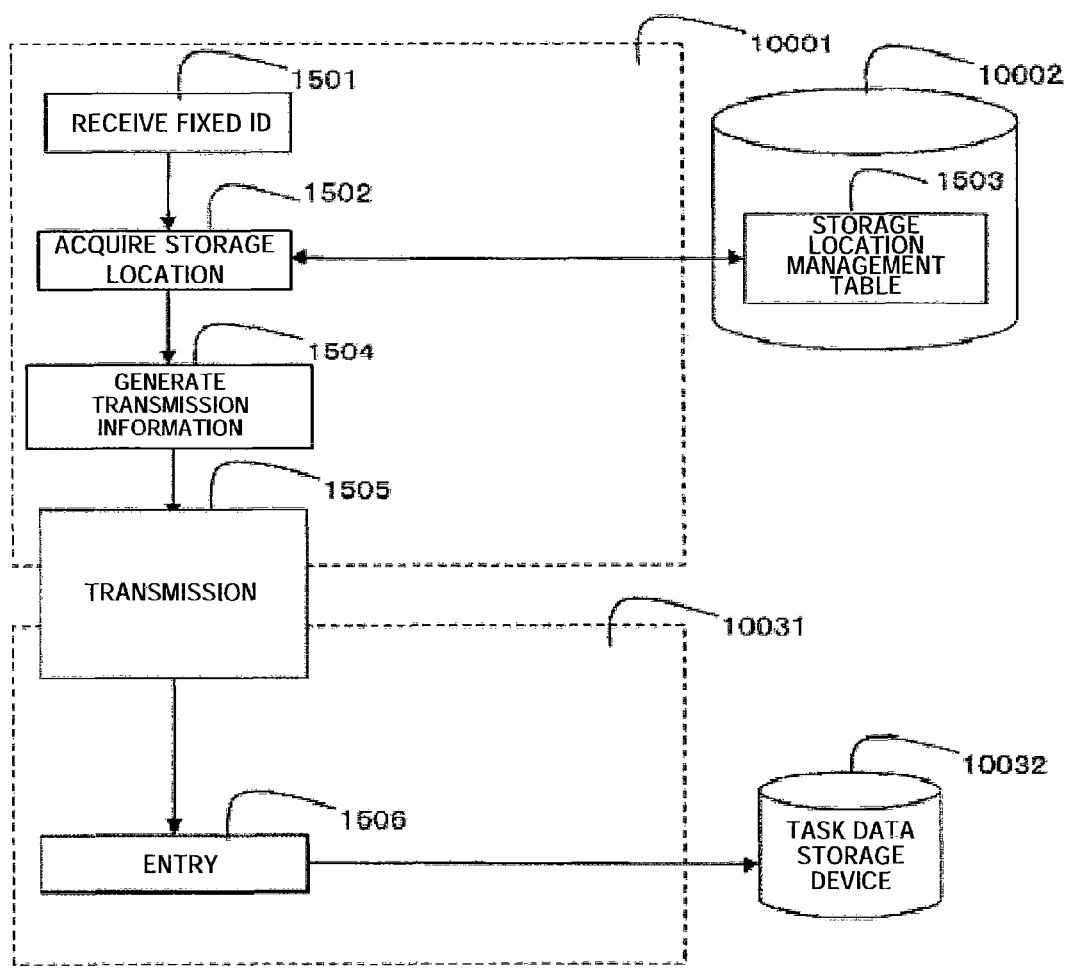
FIG. 15 is a flowchart showing the shape change 2 format of a cooperative operation in the monitoring system server.

FIG. 15 is a flow chart showing the modification 2 of cooperative action for creating/transmitting transmission information in a monitoring system server and for receiving the transmission of transmission information in a task system server, creating index information, and entering it in a task data storage device 10032.

Here, each step of the region 10001 shown by the broken line is an action of the monitoring system server, and each step of the region 10031 shown by the broken line is an action of the task system server.

First of all, in step 1501, the transmission controller 3005 receives the fixed ID from the reader manager 3001. Next, in step 1502, the monitoring system server refers to the storage location management table 1503, to acquire the monitoring data storage location. In the storage location, the URI (Uniform Resource Identifier) is adopted.

FIG. 16 is a diagram showing the composition of the storage location management table 1503 referenced in step 1502. Here, there are also cases of validity within 3 hours from reception of the initial fixed ID. The storage location management table 1503 is a table posted for each recognition of the referenced "initial fixed ID reception". Items in the storage location management table 1503 are composed from the received fixed ID, the date relating to initial reception, the time relating to initial reception, the effective deadline, and the URI. Data shown in tables 1601 and 1602, along with the fixed ID "k 1", regarding the monitoring data of 1602 following the passage of the effective time of the initial task sequence is recognized as a different task sequence. Here, the URI is shown as an http scheme, and indicates the storage location in which a program is stored which creates a monitoring screen for displaying monitoring data for each task sequence/group, and by creating a screen relating to specific monitoring data, it becomes an arrangement for calling out. Subsequently when explaining the retrieval/display of monitoring data used for tracking, a detailed explanation will be provided concerning the created display screen.

Next, in step 1504, the monitoring system server creates transmission information which includes the URI, and in step 1505, execution is accomplished of a specific transmission gram of a transmission duty controller by adding the action of linking and the like to the execution button. By this means, the transmission information is transmitted to the task system server. In step 1506, the task system server enters the URI included in the transmitted transmission information to the task data storage device 10032.

Figure 17:
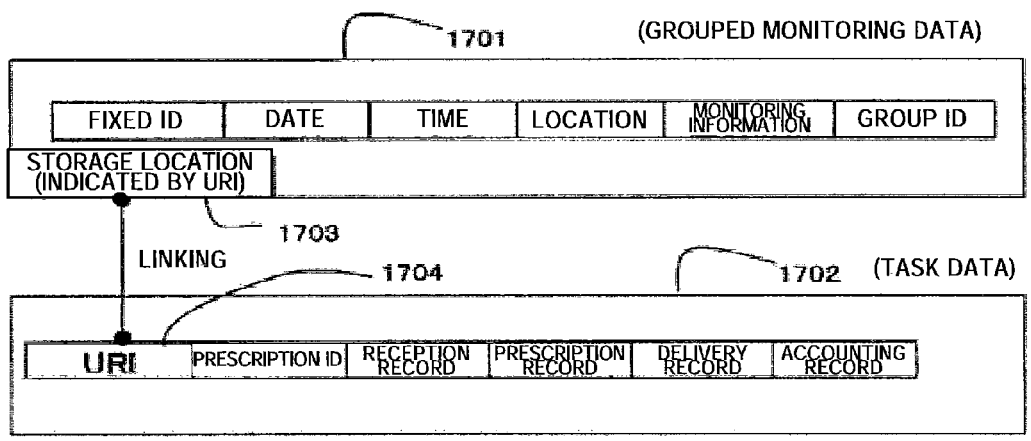
FIG. 17 is a diagram showing the composition of task data and monitoring data.

FIG. 17 is a diagram showing the composition of task data and monitoring data after the completion of the entry of step 1506 of FIG. 16. The monitoring data 1701 is composed from the data items of fixed ID, use frequency, date, time, location, monitoring information, and group ID. Here, the monitoring data is image information acquired by the monitoring camera. Task data 1702 is composed from the data items of a URI, prescription ID, reception record, prescription record, delivery record, and accounting record.

Here, by referring to the item values relating to the URI of the task data, the storage location 1703 of the monitoring data of tasks relating to the task data is indicated, and can be directly called out. In other words, by entering the item value of the URI as a task data item, a link is established from the task data to the monitoring data.

Figure 18:
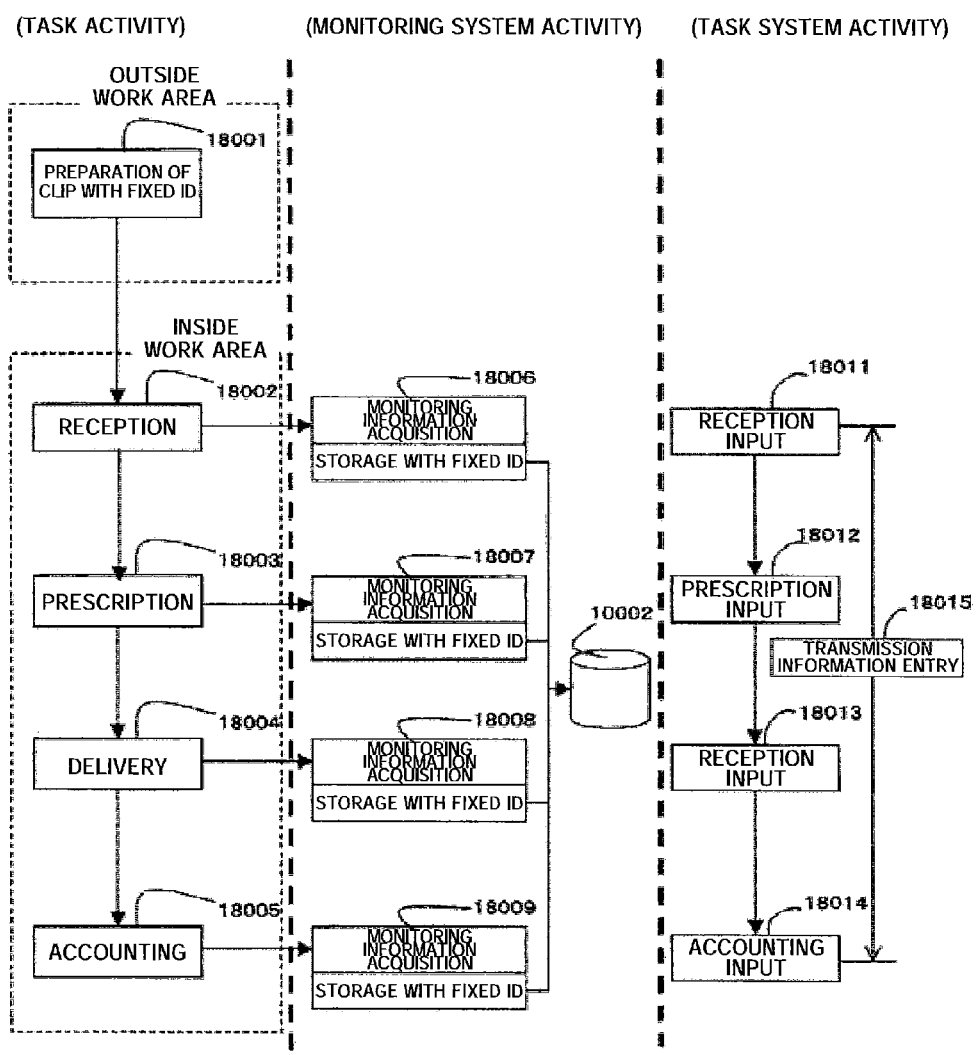
FIG. 18 is a sequence diagram showing the operation of the entire system of embodiment 1.

FIG. 18 is a sequence diagram showing the action of the entire system of the first embodiment. Here, the three items of: tasks accomplished within a work area and outside of a work area which are the object of monitoring, actions of the monitoring system relating to monitoring within the work area, and actions of the task system are chronologically described in a time sequence.

Step 18001 is a clip preparation step which prepares the document holder supplied to the task. Here, the document holder is prepared which has an RFID tag which stores the fixed ID as the tag ID. In this embodiment, the RFID tag memory is used as read-only memory, and there is no need for memory entry, or rewriting.

This task is external to the monitoring object of the monitoring system. Furthermore, the monitoring data of this task step is not managed by the system of the present embodiment.

Here, the document holder is adopted as an RFID attachment; however, the document holder is not limited to this, and appropriate adoption is possible in which it is provided to a task.

The following steps 18002-18005 are tasks within the work area, and are the object of monitoring. An explanation is provided of the chronological timeline activity of the monitoring server and task system server. Furthermore, the monitoring camera, operator, and personal computer terminal, concerning the composition of the same type of work area, use the same convenient writing, but it is not actually the same, and is nothing more than being the same in terms of the essential compositional elements of the system or monitoring object. Step 18002 is reception. In the reception location, adoption is made of the first type of work area composition shown in 10010 of FIG. 1. The action of the task system server at this time is that of the reception input step 18011, and the recipient, as the operator 10016 performs reception tasks for patients and the like who come to the pharmacy, and performs reception input from the personal computer terminal.

At this time, the monitoring system server, in the monitoring acquisition step 18006, acquires task image information photographed by the monitoring camera 10011, generates index information which includes the tag ID comprising the fixed ID, and generates monitoring data by adding index information to the image information. Also, the monitoring system server discriminates the task sequence group, and stores the monitoring data in a specific location of the image storage device 10002.

Step 18003 is the prescription step. This is the second type of work area composition provided with magnifying glass 10026 shown by 10020 of FIG. 1. The action of the task system server at this time is the prescription input step 18012, and the pharmacist, as the operator 10027, provides prescriptions for patients as written in the instruction manual, and inputs prescriptions from the personal computer terminal 10025.

The monitoring system server, at this time, in monitoring information acquisition step 18007, acquires image information of tasks photographed by the monitoring camera 10021, creates index information including the tag ID comprising the fixed ID, and creates monitoring data by adding the index information to the image information. Also, the monitoring system server discriminates the task sequence group, and stores monitoring data in a specific location of the image storage device 10002. Here, the operator 10027, in the case of detailed monitoring concerning the task object, operates the magnifying glass 10026, and acquires a magnified image. The acquired magnified image is sent to the monitoring system server, and by executing a specific program, processes the image from the magnifying glass provided in the image acquirer, and index information relating to the tag ID during detection, and stores it as monitoring data in a specific location of the image storage device 10002.

Here, in the case where operator 10027 monitors the task object, the magnifying glass 10026 is operated, and a magnified image is acquired. The acquired magnified image is transmitted to the monitoring system server, and by executing a specific program to process the image from the magnifying glass provided in the image acquirer, index information relating to the tag ID is added during detection, and is stored in a specific location of the image storage device 10002.

Figure 19:
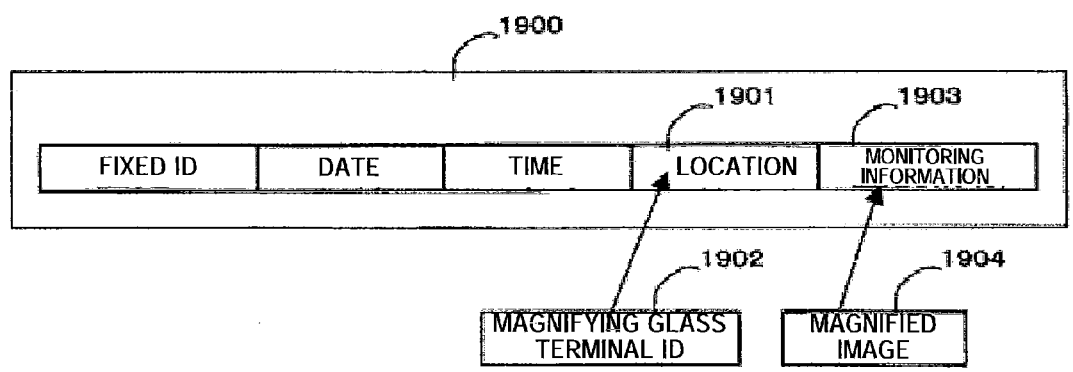
FIG. 19 is a diagram showing the composition of monitoring data relating to a magnified image.

FIG. 19 shows the composition of monitoring data relating to a magnified image. Composing the monitoring data 1900 relating to the magnified image from the data items of fixed ID, date, time, location and monitoring data is the same as monitoring data relating to image information obtained by the monitoring camera. Here, in location 1901, the magnifying glass terminal ID 1902 is entered, and the magnified image is stored in monitoring information 1903. Storage/retrieval of the monitoring data is executed by the same action as for the monitoring data relating to the image of the monitoring camera. In addition, discrimination of the task sequence group is also the same, and the group ID may also be set as the data item of the monitoring data, corresponding to the need.

Step 18004 is the delivery step. This is the second type of work area composition, provided with a magnifying glass 10026 shown by 10020 of FIG. 1. The action of the task system at this time is the delivery input step 18013, and the deliverer, as the operator 10027, performs the task of delivery to patients coming to the pharmacy, and delivery input is provided from the personal computer terminal 10025.

The monitoring system server at this time, in the monitoring information acquisition step 18008, acquires image information of tasks photographed by the monitoring camera 10021, creates index information which includes the tag ID comprising the fixed ID, and generates monitoring data by adding to the image information. Also, the monitoring system server performs discrimination of the task sequence/group, and stores the monitoring data in a specific location of the image storage device 10002.

Here, the operator 10027, in the case of a detailed monitoring of the task object, operates the magnifying glass 10026, and acquires a magnified image. The acquired magnified image is sent to the monitoring system server, and by executing a specific program which processes the image from the magnifying glass provided in the image acquirer, adds index information relating to the tag ID during detection, which is then stored as monitoring data in the specific location of the image storage device 10002.

Step 18005 is an accounting step. In the accounting location, adoption is made of a first type work area composition shown by 10010 of FIG. 1. The action of the task system at this time is accounting input step 18014, and the accounting contact supervisor, as the operator 10016, performs accounting tasks relative to patients who come to the pharmacy, and performs accounting input from the personal computer terminal 10016. The monitoring system server at this time, in monitoring information acquisition step 18009, acquires image information of tasks photographed by the monitoring camera 10011, creates index information including the tag ID comprising the fixed ID, and generates task data by adding index information to the image information. Also, the monitoring system server discriminates the task sequence/group, and stores the monitoring data in the specific location of the image storage device 10002.

(Tracking)

Figure 20:
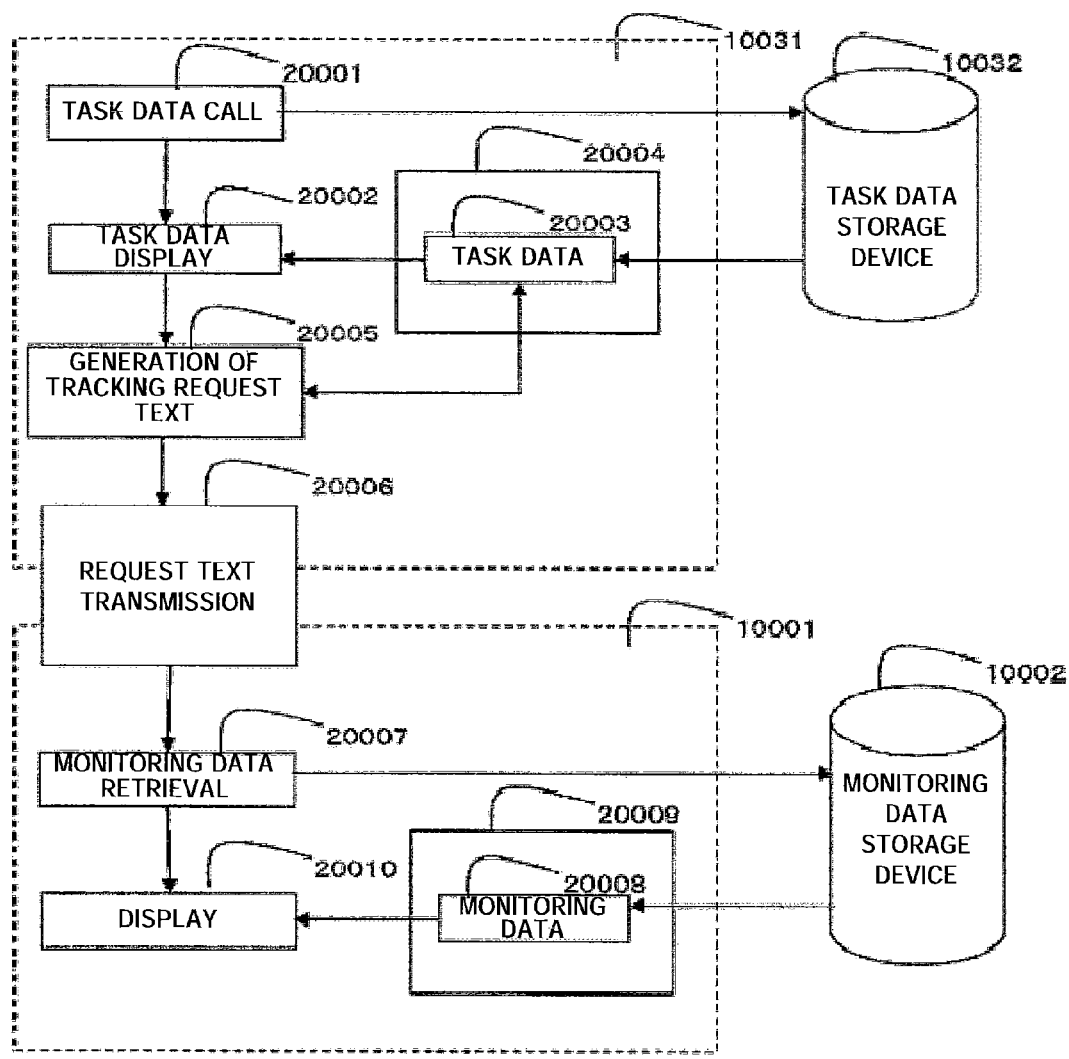
FIG. 20 is a flowchart showing the operation in the case of performing tracking.

FIG. 20 is a flowchart which generates problems and the like concerning tasks relating to task data during handling by the task system, and shows the actions taken in the case of performing tracking for confirmation purposes.

Here, the action of the steps of the region of 10031 shown by the broken line is actions of the task system server. In addition, actions of the region 10001 shown by the broken line are actions of the monitoring system server.

In step 20001, the task system server calls out desired task data relative to the task data storage device 10032 in a known format which provides key input and the like for patient names etc. The task data 20003 becoming the objects developed in work area 20004 maintained in the memory (not shown in the drawing) of the task system server, in which real time data processing becomes possible, and is displayed in step 20002, in a specific format on a monitor (not shown in the drawing).

Next, in step 20005, the task system server generates tracking request text which includes a retrieval key necessary to monitoring data retrieval from the data items of the task data developed in the work region. Also, in step 20006, the task system server transmits the generated request text to the monitoring system server.

Next, in step 20007, the monitoring system server extracts the retrieval key from the received request, and retrieves the monitoring data. The retrieval key indicates the data item and its item value in a format such as that described below.

Here, in the case where monitoring data is specific with a fixed ID and date, the format is (fixed ID, k 1) and (date, 20091023).

Or, if it is a specific format then the fixed ID and use frequency is the format of (fixed ID, k 1) and (use frequency, 2).

With the URI, if in a specific callout format, then as the format of (URI, http//www/drug.com/trace.exe?id=g1).

In step 20010, the monitoring system server performs display of monitoring data 20008 developed in work region 20009 of the memory (not shown in the drawing) of the monitoring system server, which is retrieved and called out. Here, the called out monitoring data records the convenient first data of the diagram, all of which belong to the same task sequence/group. Since each monitoring data establishes and manages a group ID, callout and display can be accomplished for each group.

Figure 22:
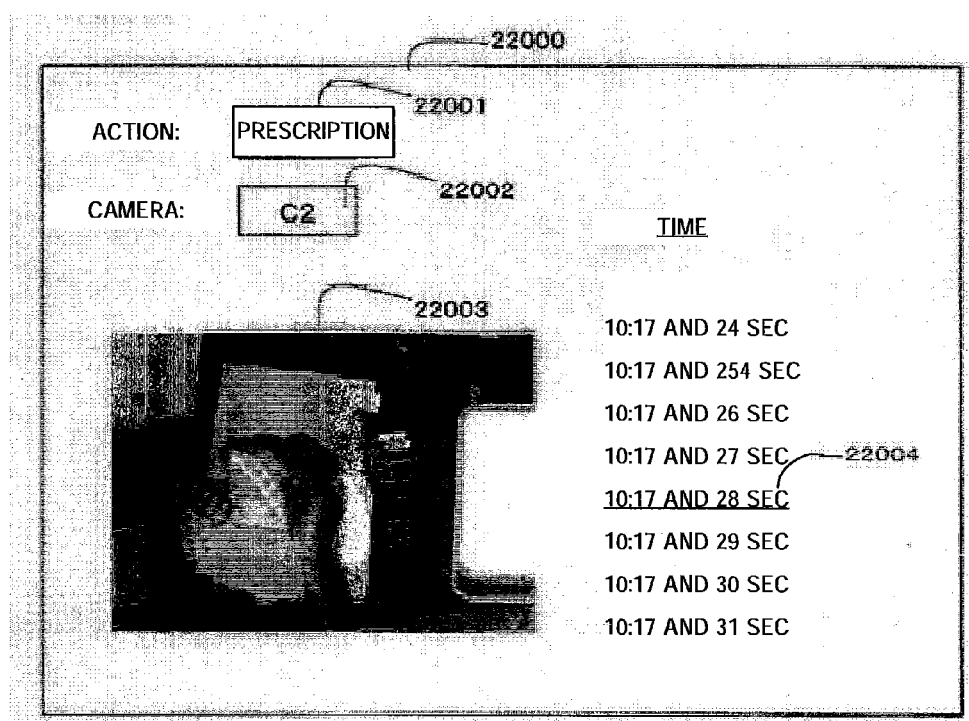
FIG. 22 is a diagram showing a screen on which is displayed monitoring data.
Figure 23:
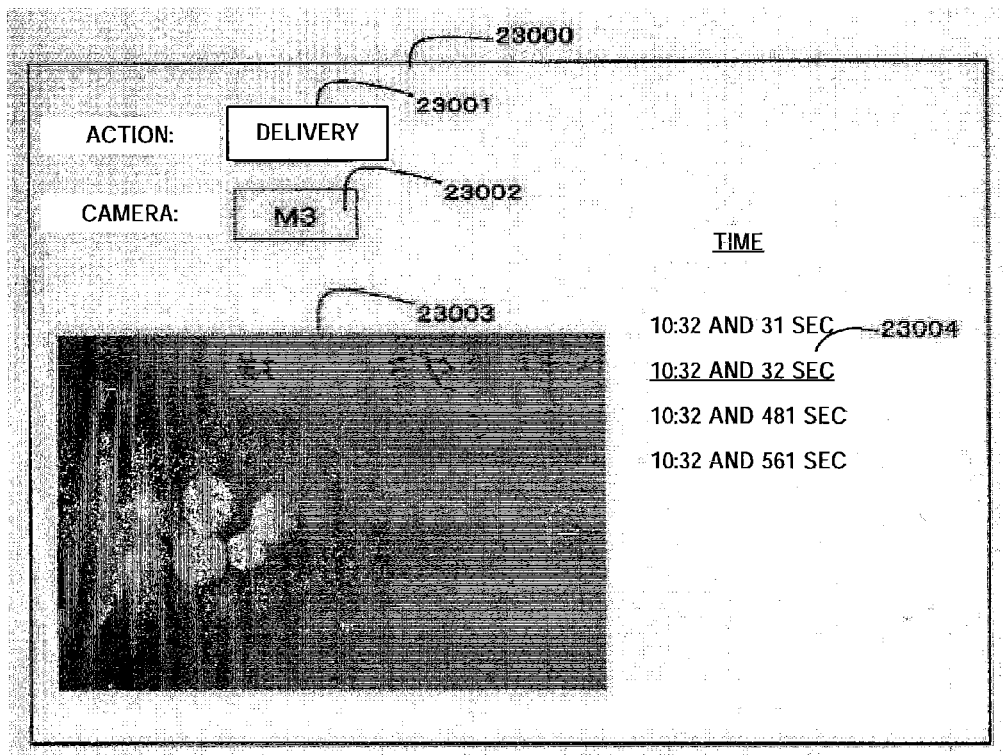
FIG. 23 is a diagram showing a screen on which is displayed monitoring data which includes a magnified image.

FIG. 21-23 are examples of the display screen of the retrieval results. The display of the retrieval results relating to the present invention can be appropriately changed corresponding to the nature of the task of the monitoring object.

In FIG. 21, a display screen 21000 is the screen initially displayed after calling out the monitoring data. The group ID of the retrieved monitoring data is displayed in the image region 21001. Here, monitoring data is called out which relates to the task sequence/group grouped as "g1". Each monitoring data is displayed as a list discovering the action, location, (monitoring camera and terminal ID of the magnifying glass), and the date and time of commencement of photography, and the display displays the monitoring data discovered by adding the appropriate action of the referenced clicking at the HTML document.

FIG. 22 shows the screen that displayed the monitoring data shown in the image region 21002 in FIG. 21. The operation of the monitoring object is the "prescription" displayed in the image region 22001, and the camera terminal ID is the "C 2" displayed in the image region 22002. C 2 is the terminal ID showing the monitoring camera of the prescription place. Image region 22003 is an image at the time shown in 22004. Here, the "time" displayed in a spreadsheet is HTML text, and by adding the appropriate action of clicking and the like, the image of the desired time can be displayed.

FIG. 23 shows the screen which displayed the monitoring data shown in the image region 21003 in FIG. 21. The operation of the monitoring object is the "delivery" displayed in image region 23001, and the camera terminal ID is "M 3" shown in 2302. M 3 is the terminal ID which shows the magnifying glass of the delivery location. The image region 2303 is a magnified image monitored by the operator at the time shown in 23004. Here, the "time" shown in a spreadsheet is an HTML document, and by adding the appropriate action of clicking and the like, the magnified image of the specific time can be displayed.

Embodiment 2

(Transcribing Format of Written Information)

Figure 24:
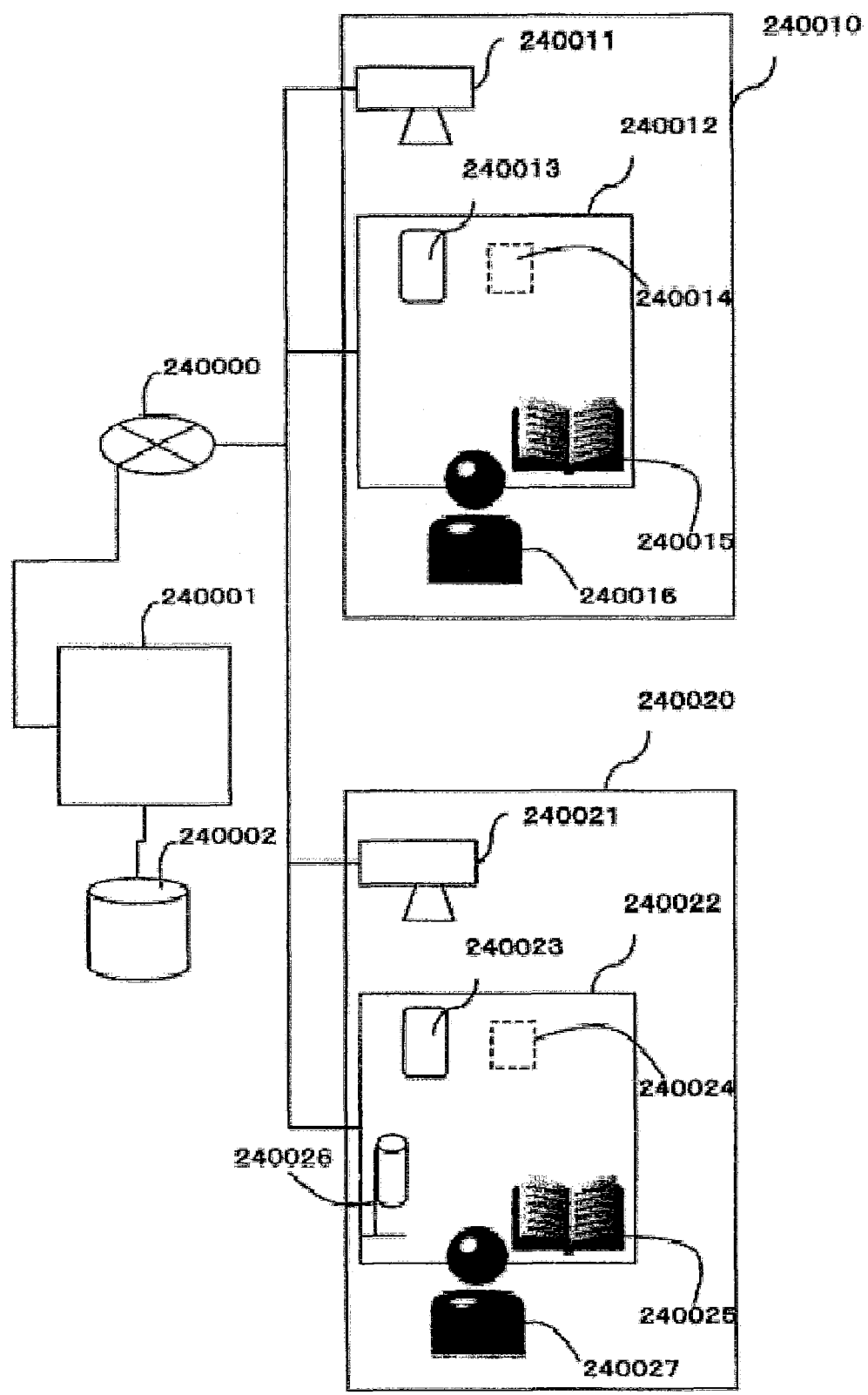
FIG. 24 is a summary composition diagram of a monitoring system relating to embodiment 2.

FIG. 24 is a summary abbreviated compositional diagram of a monitoring system relating to the second embodiment of the present invention. This is the embodiment form of a case of introducing a system to the pharmacy reception, prescription location, delivery location, and accounting. The monitoring system is composed from a network to four is 0000, and monitoring system server 240001, and monitoring data storage device 240002, a first type work area 240010 which performs these tasks comprising the monitoring object, and the second type of work area 240020.

Here, conveniently two types of work areas are explained one at a time. The first type of work area 240010 adopts a receive location and accounting location, and the since the second type of work area 240020 is adopted to a prescription location and delivery location, a total of four respective types of work areas exist, provided two at a time.

Furthermore, the work area of the present invention is not limited to each type being handled two at a time, but a composition may be appropriately selected with the composition of the first or second type of work, but only one type of work area may also accommodate multiple work areas.

The composition of the first type of work area is as follows. A monitoring camera 240011 and a workbench 240012 are set to photograph the task while the operator 240016 is facing the workbench 240012. Here, an RFID reader 240013 is provided on the workbench 240012 and is managed by the monitoring system server via the network. Upon placing a document holder 240014 fitted with an RFID tag used by tasks in the detection area, a specific trigger signal is transmitted. The operator 240016 performs tasks relating to compounding, and inputs tasks into the compounding record 240015.

Here, task input is accomplished in written format to the compounding record; however, a composition may also be used which is performed on a personal computer provided with a ledger function, without being limited to the ledger of a paper medium, such as that of the compounding record.

The composition of the second type of work area is as follows. A monitoring camera 240021 and workbench 240022 are arranged, and the monitoring camera 240021 is used by an operator 240027 to photograph tasks while facing the workbench. Here, to the workbench 240022 is attached an RFID reader 240023 and a magnifying glass 240026. Upon placing the document holder 240024 which has an RFID tag used by the task of the detection area of the RFID reader, a specific trigger signal is transmitted. The magnifying glass is connected to the network, and the operator either sets the subject object within the photographic parameters of the magnifying glass, or faces the magnifying glass toward the subject object, and by operating a switch (not shown in the drawing) is able to acquire the magnified image. Here, the magnified image, along with being used by the operator to confirm the task object by means of a monitor (not shown in the drawing) or the like, is transmitted to the monitoring system server via the network. The operator 240027 performs tasks relating to compounding, and performs task entry to the task record 240025. Here, task input is provided in a written format to the compounding record; however, a composition may also be accomplished on a personal computer provided with a ledger function, without being limited to the ledger of a paper format such as in the compounding record.

The composition of the system shown here, is nothing more than an example, and an appropriate composition can be had corresponding to an established object or specific hardware device.

In addition, the action of each functional "unit" of a monitoring system server explained below, is executed by a prepared program on a personal computer or the computer of a workstation or the like provided with a monitor, keyboard, and interface of a mouse and the like, and is realized by controlling each device. In addition, these programs are read out from a recording medium by means of the computer, and are recorded on a readable storage medium by a computer having, for example, hardware, a USB memory, a CD-ROM, an MO, and DVD and the like, and executed by the operation of the system user.

Figure 25:
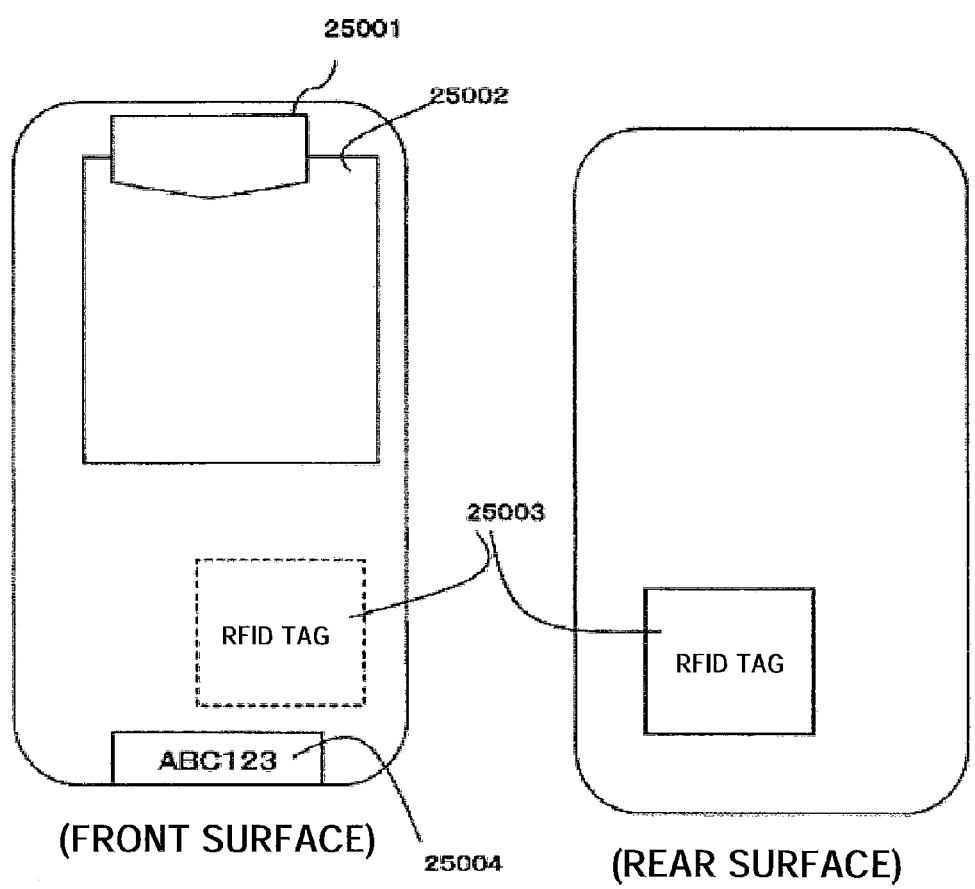
FIG. 25 is a diagram showing the composition of a document holder.

FIG. 25 is a diagram showing the composition of document holders 240014 and 240024 used by the present invention. The document holders 240014 and 240024 make one preparation relative to one task, and hold documents of operational instructions on which are the recorded instructions concerning actions relating to the task, carried to each work area as the task progresses. The operator, in a specific position of the workbench, performs the task while referring to the instruction items held in the document holders 240014 and 240024. Holders 240014 and 240024 are composed from a clip 25001, a display 25004 on which is recorded the operating instruction sheet 25002, the RFID tag 25003, and the tag ID. Upon placing the document holder on the workbench, the RFID tag is detected by means of the RFID reader provided on the workbench. By means of the detection/non-detection pattern, progress of the task is detected, and a trigger signal is transmitted to activate the monitoring camera, acquiring the image information of the sequence of tasks progress. The monitoring camera control is already known, and is recorded in Patent Literature 1.

Figure 26:
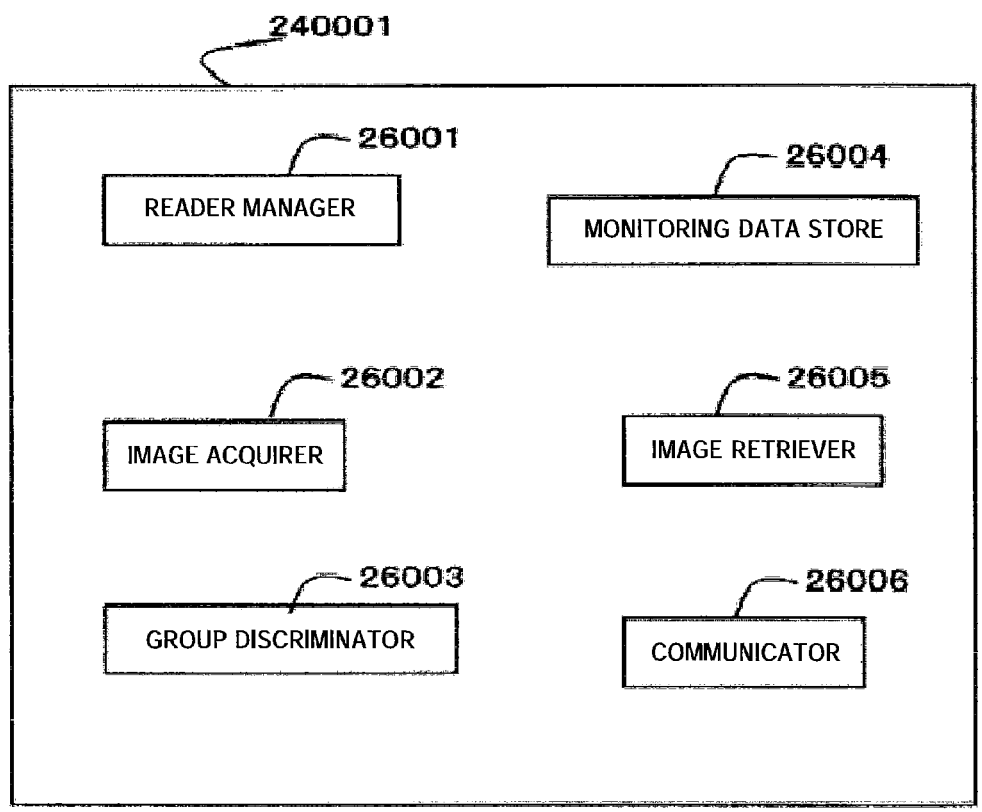
FIG. 26 is a diagram showing the internal composition of monitoring system server.

Here, the tag ID is displayed as a display, and visibility relating to the tag ID may be provided with a good symbol. In addition, the document holder is used as an RFID tag addition; however, the present invention is not limited to this, and the operating instruction documents or medical drug products may be stored in a tray, FIG. 26 is a monitoring system server 240001 which is a diagram which shows the internal composition of the monitoring system server 240001 of the present invention, composed of: a reader manager 26001 which manages the detection operation of the RFID reader, and an image acquirer 26002 which acquires image information transmitted from the monitoring camera, and stories index information which is been generated/assigned, and a group discriminator 26003 which discriminates and groups task sequence/groups, a monitoring data store 26004 which stores monitoring data in a specific location, an image retriever 26005 which calls out monitoring data receiving the input of specific the information, and a communicator 26006 which controls communications operations on the network for operating each of these functional units.

Here, the monitoring data is composed from information read from the detected RFID tag, date, time, index information generated from the information of a monitoring camera terminal ID (location) and the light, and image information from a monitoring camera. Furthermore, to the monitoring data, a specific group ID is assigned, after discriminating whether something belongs to one task sequence/group by whether it has been acquired within a specific effective deadline from the initial RFID tag detection.

The task sequence/group, when a patient comes to the pharmacy, summarily grasps all of the compounding tasks (reception task, prescription task delivery task and accounting task) relating to the prescriptions at the time, as one sequence.

(Cooperative Action of Each Functional Unit in A monitoring System Server)

Figure 27:
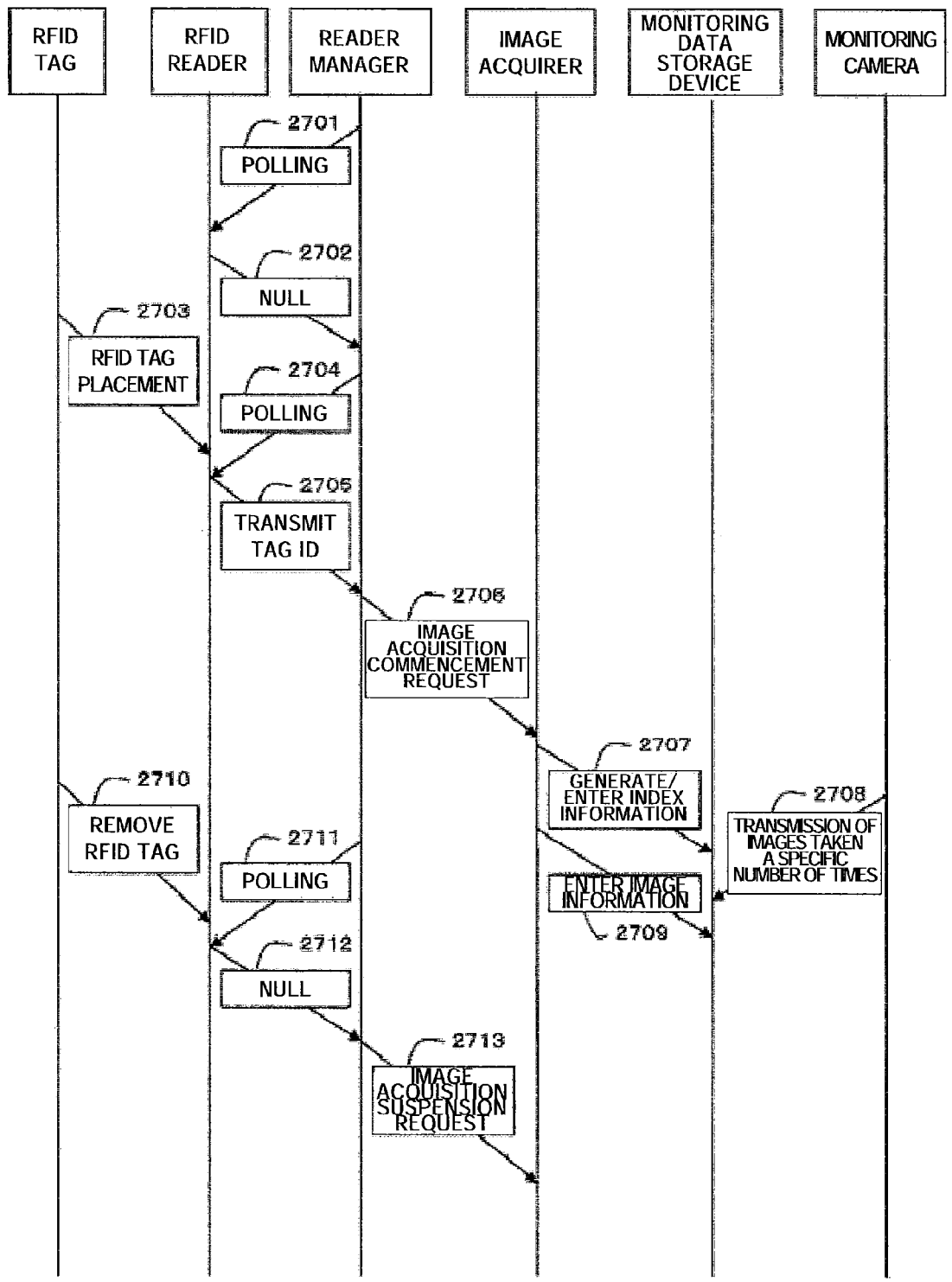
FIG. 27 is a sequence diagram showing the cooperative operation stored in a monitoring data storage device.

FIG. 27 is a sequence diagram showing image acquisition, the generation of monitoring data, and cooperative action by each functional unit/device of a reader manager or the like which shows the actions stored in the monitoring data storage device 10002.

In step 2701, polling is performed relative to an RFID reader by means of the action of a reader manager which executes a specific RFID reader management program. In the absence of a transmission request, in step 2702, a "Null" signal is returned. Also, in step 2703, if an RFID reader is placed within specific detection parameters, then transmission is accomplished of the tag ID of step 2705. The tag ID is a discrimination element pre-stored in the memory of the RFID tag.

The reader manager which received the tag ID, in step 2706, requests image acquisition relative to the image acquirer. The image acquirer, in step 2707, generates index information which includes a tag ID, and enters it into a monitoring data storage device. An explanation of the generation of index information is provided hereafter.

In addition, the monitoring camera, in step 2708, transmits the image information of a specific amount to the monitoring data storage device. In step 2709, the image acquirer enters the image information to the monitoring data storage location into which the index information had been entered in the previous step.

Next, in step 2710, if the RFID tag is removed from within the specific detection parameters, then, in step 2712, "Null" is returned relative to the polling of step 2711. The reader manager to which the "Null" has been returned, in step 2713, transmits an image acquisition termination request relative to the image acquirer.

(Generation of Index Information)

Figure 28:
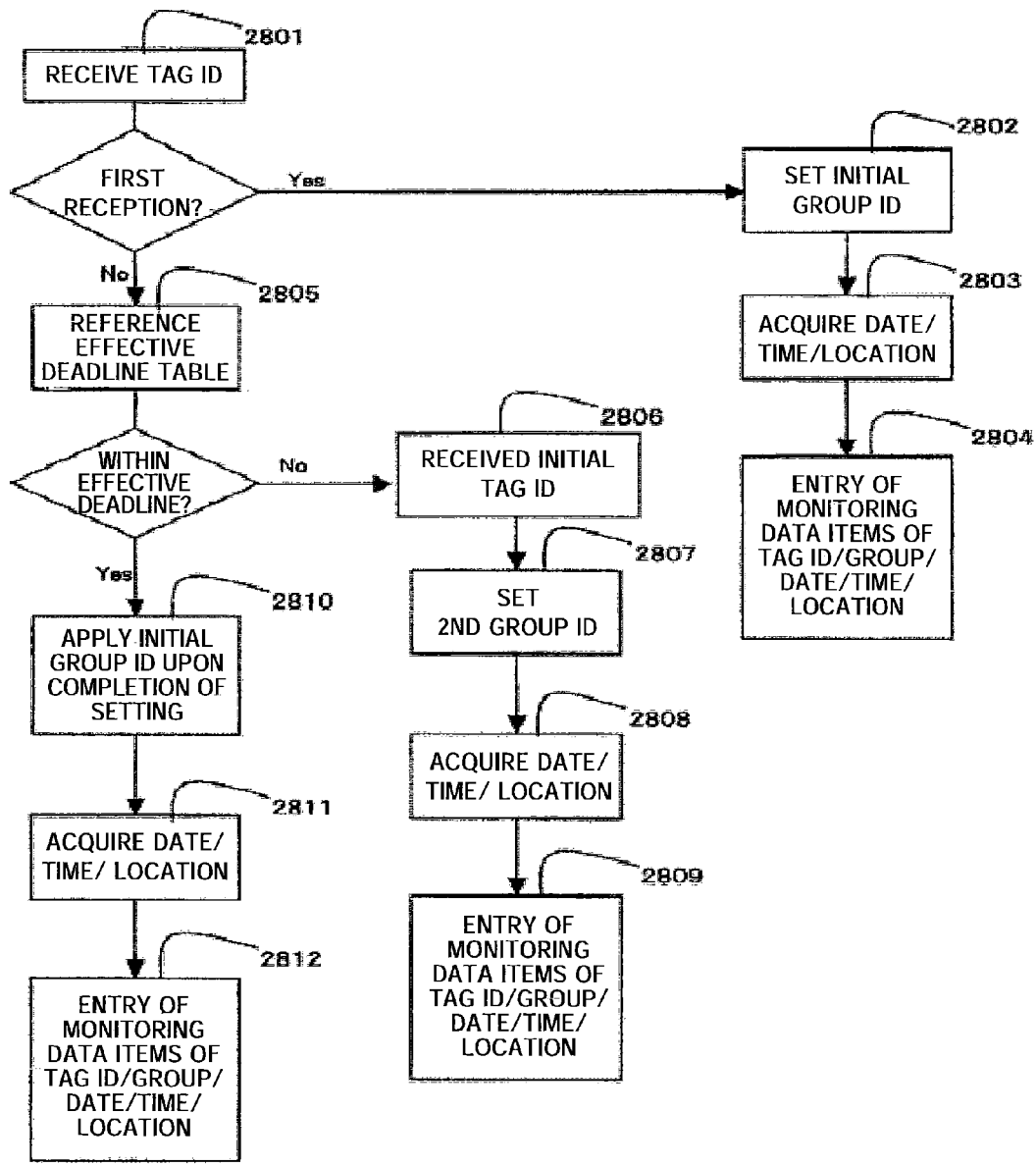
FIG. 28 is a flowchart which explains the operation of the generation/entry of index information.

FIG. 28 is a flow chart that explains the action of generation/entry of index information in step 2707 of FIG. 27.

First of all, in step 2801, the image acquirer receives the tag ID transmitted from the reader manager. The image acquirer discriminates whether it is an initial reception, by referencing the monitoring data which holds the tag ID relative to the monitoring storage device as index information.

If the discrimination results are "Yes", in other words, if it is an initial reception, then in step 2802, the image acquirer sets the initial group ID. Next, in step 2803, the image acquirer acquires the information of the date, time and location relating to the detection of the tag ID. Here, the information of location is the monitoring camera terminal ID, and the work area can be specific by the terminal ID. Also, step 2804, the image acquirer enters each item of group ID, date, time, location and tag ID into each item corresponding to the pre-established monitoring data.

On the other hand, if the results of discrimination are "No", in other words, if it is a tag ID already relating to monitoring data for which setting has already been completed of the task sequence/group, the image acquirer, in step 2805, refers to a specific effective deadline table. If not within the effective deadline, the image acquirer, in step 2806, receives the initial tag ID, and in step 2807, establishes a second group ID which is different from the group ID for which establishment has already been completed. Next, in step 2808, the image acquirer acquires information of the date, time and location relating to the detection of a tag ID. Also, in step 2809, the image acquirer makes an entry into each item corresponding to the monitoring data which pre-established a set or acquired tag ID, the date, time, and location.

In step 2805, referencing the specific effective deadline table, if within the effective deadline, then in step 2810, the image acquirer assigns an initial group ID which has already been set. Next, in step 2811, the image acquirer acquires information of the date, time, and location relating to the detection of the tag ID. Also, in step 2812, the image acquirer enters the assigned/acquired group ID, date, time, location and tag ID to each item corresponding to the monitoring data. Here, setting the group ID, a format is adopted which sets the group ID in each monitoring data. However, the invention relating to the task sequence/group of the present invention is not limited to this format, and a group management format may also be used in which the monitoring group belonging to the same task sequence/group can be registered in the management table set for each group without sending the data items relating to the groups in the monitoring table.

Figure 29:
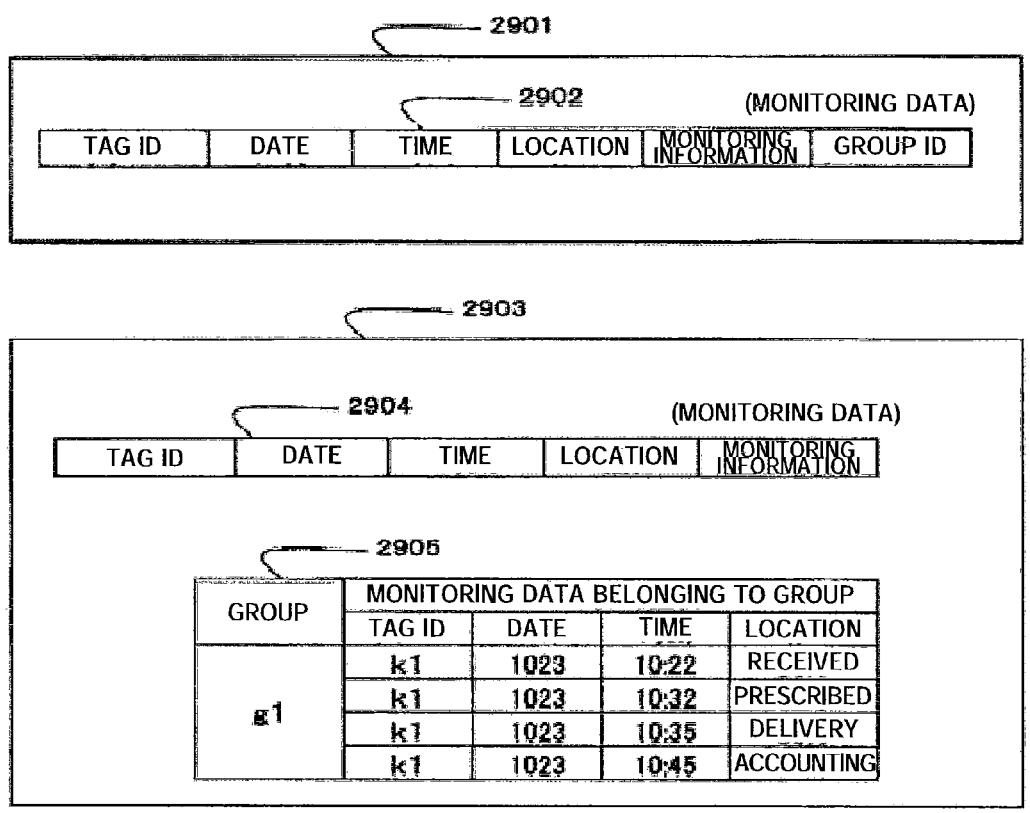
FIG. 29 is a summary diagram in which formulas are compared.

FIG. 29 is a summary diagram comparing above formats. Shown is the monitoring data 2902 stored in the monitoring data storage device 2901 relating to the format which set the group ID items in the monitoring data, and which registers the monitoring data relating to the same task sequence in the management table 2903 without attaching the group ID items, and the monitoring data storage device which stored the monitoring data 2903 without attaching group ID items.

Furthermore, the monitoring information is image information acquired by the monitoring camera or magnified images obtained from the magnifying glass.

(Effective Deadline Table)

FIG. 30 is a diagram showing the composition of the effective deadline table with reference to step 2805 of FIG. 28. Here, there are also cases which are effective within three hours from the initial reception of the tag ID. This is a table to which the "reception of the initial tag ID" is added each time it is recognized. The items of the effective deadline table are composed from the date, time relating to initial reception, and the effective deadline and group ID. Referencing this table, the image acquirer assigns the same group ID relative to monitoring data relating to the same tag ID within the deadline. Data shown in table 30001 and 30002 includes tag ID "k1"; however, if the monitoring data 30002 following the passage of the effective deadline of the "g1" task sequence is recognized as having a different task sequence, a second group ID "g8" is set which differs from the initial "g1".

(Action of the Entire System)

Figure 31:
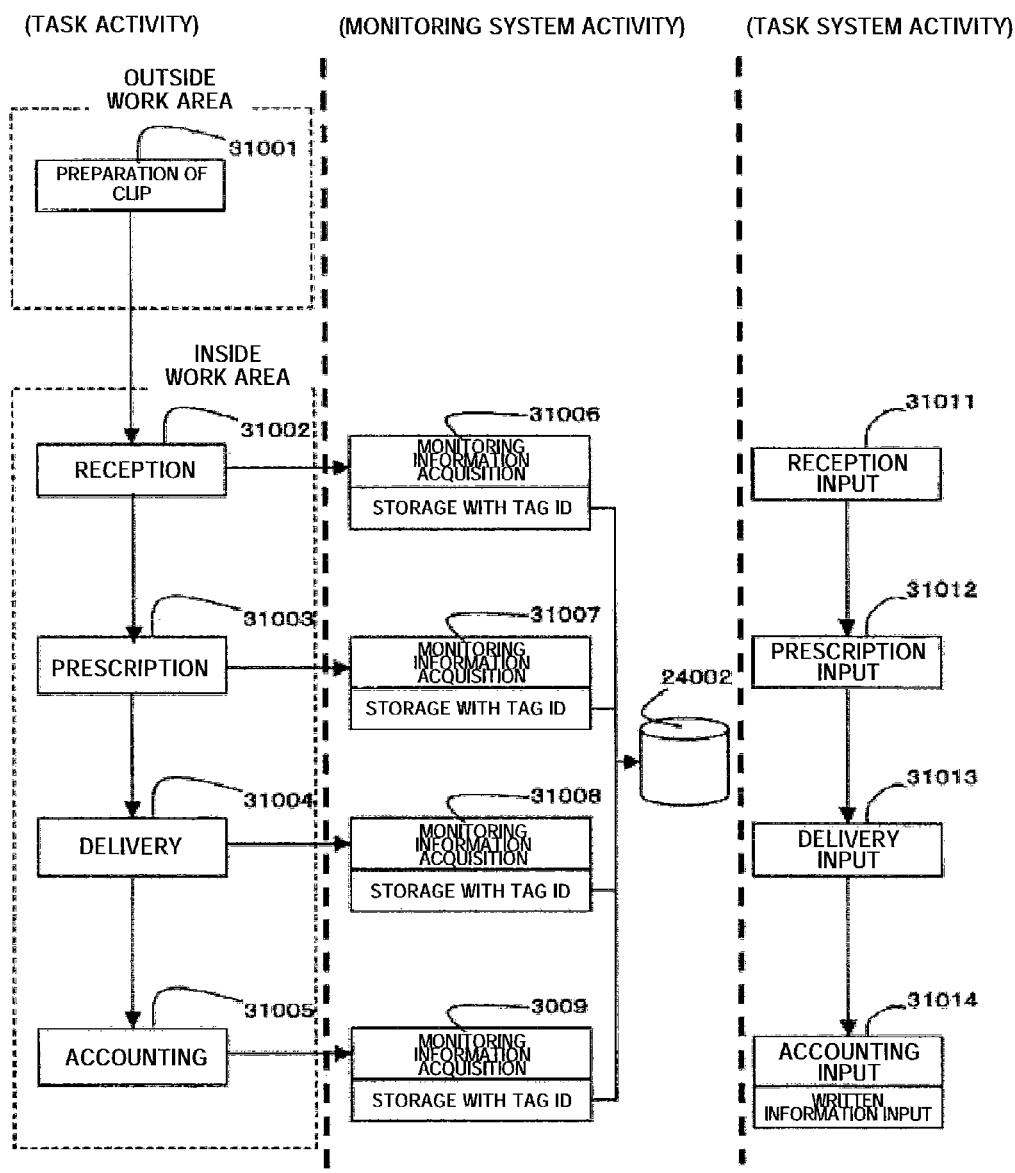
FIG. 31 is a sequence diagram showing the operation of an entire system.

FIG. 31 is a flowchart showing the action of the entire system of the present invention. Here, the 3 tasks accomplished within and outside of the work area, which are the object of monitoring, the action of the monitoring system relative to monitoring within the work area, and the entry to the compounding record, are described in a chronological timeframe.

Step 31001 is a clip preparation step. Here, a document holder is prepared on which a tag ID has been written as written information. This is a task of other than the monitoring object of the monitoring system. Furthermore, the monitoring data of this task step is not managed by the system of the present invention.

Here, the document holder is adopted as an RFID addition; however, as explained hereafter, the document holder is not limited to this, and adoption is also possible of items appropriately provided to tasks. In addition, as written information, an appropriate indication may also be made to something having a relationship to a tag ID, rather than to the tag ID itself The following steps 31002-31005 are tasks carried out within the work area, and are the object of monitoring.

The actions of the monitoring system corresponding to the time chronological time frame are explained and a joint explanation is provided of entries to the compounding record. Furthermore, the monitoring camera, operator and compounding record use the same written account, as convenient; however, the monitoring camera, operator and compounding record use the same written account, and though they are not actually the same, they do nothing more than use the same writing for the same things as the compositional elements in each work area.

Step 31002 is the reception step. At this time, the receiving individual, acting as the operator, performs reception tasks relative to patients coming to the pharmacy, and provides reception input 31011 to the compound record. The monitoring system executes monitoring information acquisition step 31006, generates monitoring data from the task image information acquired by the monitoring camera, enters index information including the tag ID into the monitoring data, and stores it in the monitoring data storage device 24002

Step 31003 is the prescription step. At this time, the pharmacist, acting as the operator, provides prescriptions for patients and the like as written in the instruction manual, and enters the prescription in the compounding record. In the monitoring system, monitoring information acquisition step 31007 is executed, and monitoring data from the images of tasks acquired by the monitoring camera is generated, index information including the tag ID is entered, and stored in the monitoring data storage device 24002.

Here, when monitoring details concerning task objects, the operator operates the magnifying glass 240026, and acquires magnified images. The acquired magnified images are sent to the monitoring system server, and by executing a specific program which processes the images from the magnifying glass attached to the image acquirer, index information is added relative to the tag ID during detection, and stored as monitoring data in the monitoring data storage device 240002.

Step 31004 is the delivery step. At this time, the deliverer, acting as the operator, performs delivery tasks for patients and the like coming to the pharmacy, and provides delivery input 31013 to the compounding record. In the monitoring system, the monitoring information acquisition step 31008 is executed, monitoring data from the image information of tasks acquired by the monitoring camera is generated, index information including the tag ID is entered into the monitoring data, and is stored in the monitoring data storage device 24002.

Here, when monitoring the details of task objects, the operator operates magnifying glass 240026, and acquires magnified images. The acquired magnified images are sent to the monitoring system server, and by executing a specific program to process images from the magnifying glass attached to the image acquirer, index information is added relating to the tag ID during detection, and is stored as monitoring data in a specific location of the monitoring data storage device 240002.

Step 31005 is the accounting step. At this time, the person responsible for accounting performs accounting tasks for patients and the like coming to the pharmacy, and provides accounting and written information input to the compounding record in the input of step 31014. In the monitoring system, monitoring information acquisition step 3009 is executed, monitoring data is generated from the image information of tasks acquired by the monitoring camera, and index information, including that of tag ID is entered to the monitoring data, and stored in the monitoring data storage device 24002.

Input of written information, in the written information input column established in the task pages of the compounding record, is manually input by the operator visually confirming information which can easily extract the tag ID by referencing a specific reference table in which a relationship is established with the tag ID or the tag ID written in the document holder.

Here, input of the written information was accomplished at the time of accounting input; however, the timing of the input of the present invention may appropriately adopt a time when the task load of the person responsible for delivery/prescriptions is low.

In addition, input of written information was manually input following visual confirmation; however, the input of the present invention is not limited to this, and in the case of using a personal computer provided with a ledger function for task input, a format can also be used which reads out RFID tags added to document holder by means of an RFID reader added to the personal computer.

Figure 32:
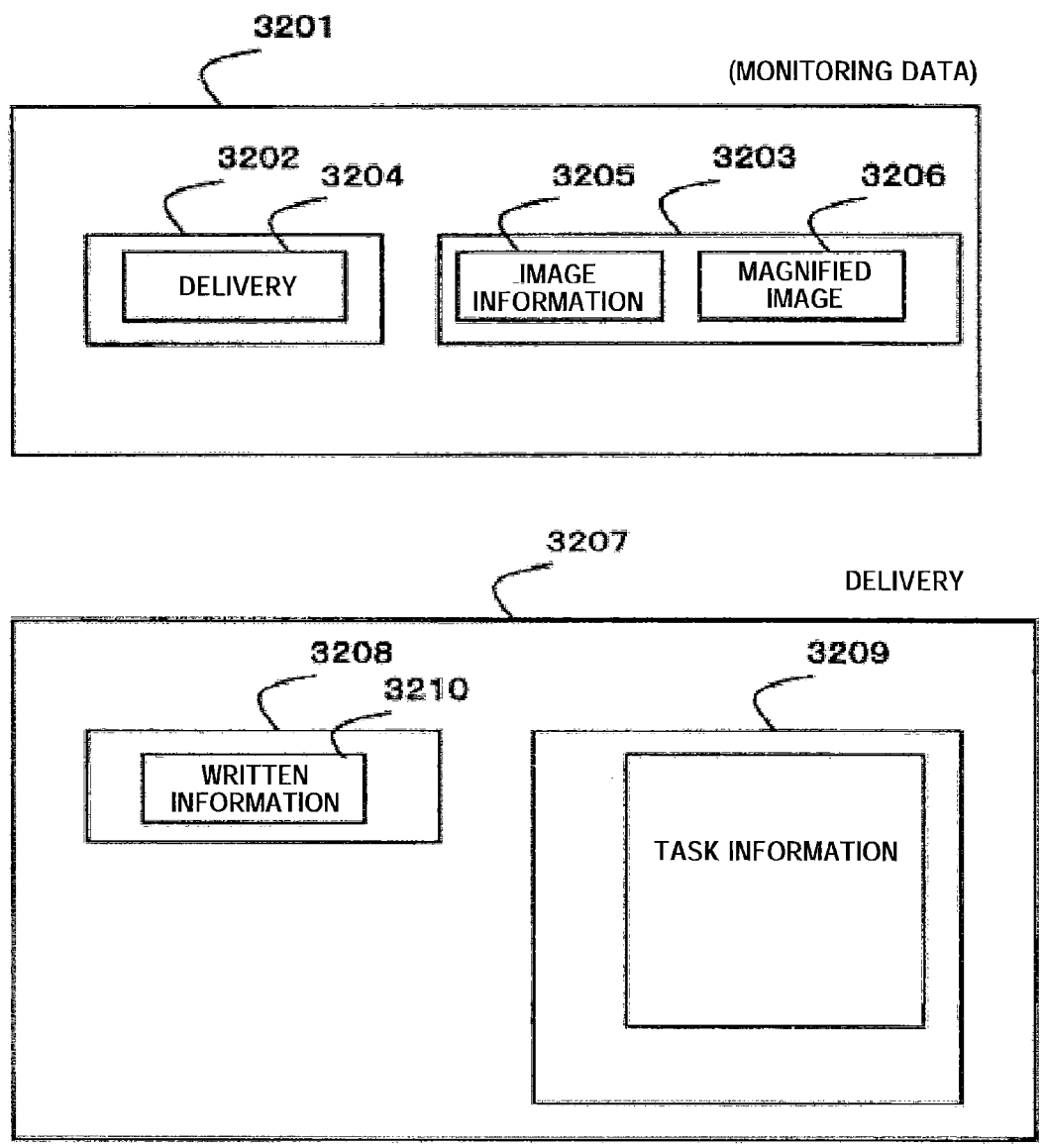
FIG. 32 is a summary diagram showing the recorded information of a data composition and ledger.

FIG. 32 is a summary diagram showing the composition of data generated by the flowchart of FIG. 31 and the written information of the ledger. Monitoring data 3201 is data relating to the monitored image information in magnified images and in monitoring tasks corresponding to entries in the ledger. The monitoring data is composed from an index unit 3202 and a monitoring information unit 3203. Here, the data items of the index unit include tag ID 3204. The data items of the monitoring information is composed from image information 3205 from the monitoring camera and image information 3205 and magnified images 3206 from the magnifying glass.

Page 3207 relating to the ledger tasks are composed from the written information input column 3208 and written task information input column 3209. In the written information input column 3208 is recorded written information 3210, and if written information is input to the monitoring system corresponding to tracking needs, retrieval can be achieved by referencing the index information of the monitoring data. When the written information is not the tag ID itself, a reference table should be prepared which establishes a relationship between the written information and the tag information.

(Tracking)

Figure 33:
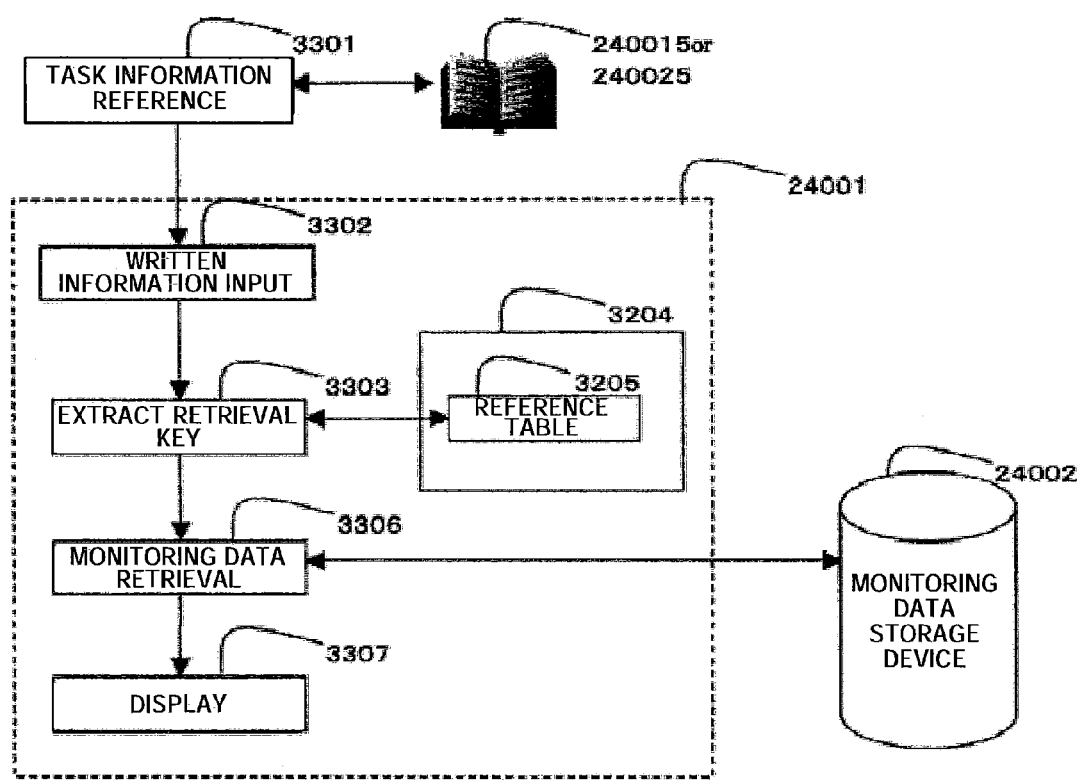
FIG. 33 is a flowchart showing the operation in the case of performing tracking.

FIG. 33 is a flowchart in which problems and the like occur concerning tasks relating to task data during handling by the task system, and shows the action when tracking for the purpose of confirmation.

Here, the action of steps in region 240001 shown by the broken line is actions of the monitoring system server.

In step 3301, the monitoring system server the compounding record 240015 (and 200025) which is opened on the page of the task information recorded column relating to desired task information, and examines written information of the written information recorded column. Next, in step 3302, the monitoring system server receives and attaches the input of examined written information from the specific tracking screen. Next, in step 3303, the monitoring system server, referring to the reference table, extracts the tag ID as a retrieval key corresponding to the input written information developed in the work region 3304 of the memory (not shown in the drawing) of the monitoring system server.

FIG. 4 shows an example of a reference table. Here, since the tag ID used for written information has a different written indication, a reference table is necessary in which the document holder has pre-created preparatory steps and the like; however, if the tag ID is written as it is, then an action to extract such a retrieval key is unnecessary.

In step 3306, the monitoring system server executes retrieval of monitoring data. In this instance, the called out monitoring data, in step 3307, is displayed in a specific format. Also, the monitoring system server calls out desired task data relative to the task data storage device 10032. The subject task data 20003 is developed in work region 20004, maintained in the memory (not shown in the drawing) of the monitoring system server, can be processed in real time, and in step 20002 of FIG. 20, is displayed in a specific format on the monitor (not shown in the drawing).

(Monitoring Data Display)

FIG. 35-38 is an example of the display screen of the retrieval results. Display of the retrieval results relating to the present invention is in a form which can be appropriately changed corresponding to the nature of the object monitoring task.

In FIG. 35, the display screen 3500 is a screen initially displayed after calling out the monitoring data. The retrieved monitoring data tag ID is displayed in region 3501. The tag ID of the "k1" displayed here is activated by the stored RFID, and is selectively displayed by calling out the monitoring data 3502 and 3503 relating to the photograph monitoring sequence/group "G1". The display relating to each monitoring data is in HTML text, and a detailed display of the monitoring data of a desired group can be obtained by adding the appropriate action of clicking or the like.

Figure 36:
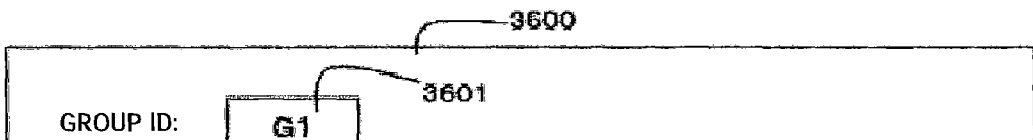
FIG. 36 is a diagram showing the detailed display screen of monitoring data.

FIG. 36 is a detailed display screen of the monitoring data grouped in "G1" of the image region (Group ID Display Column) 3601. The action, location (camera terminal ID) and time of commencement of photography are displayed as headings, with each display being written in HTML text, and by the additional action of clicking and the like, selective monitoring data can be displayed.

Figure 37:
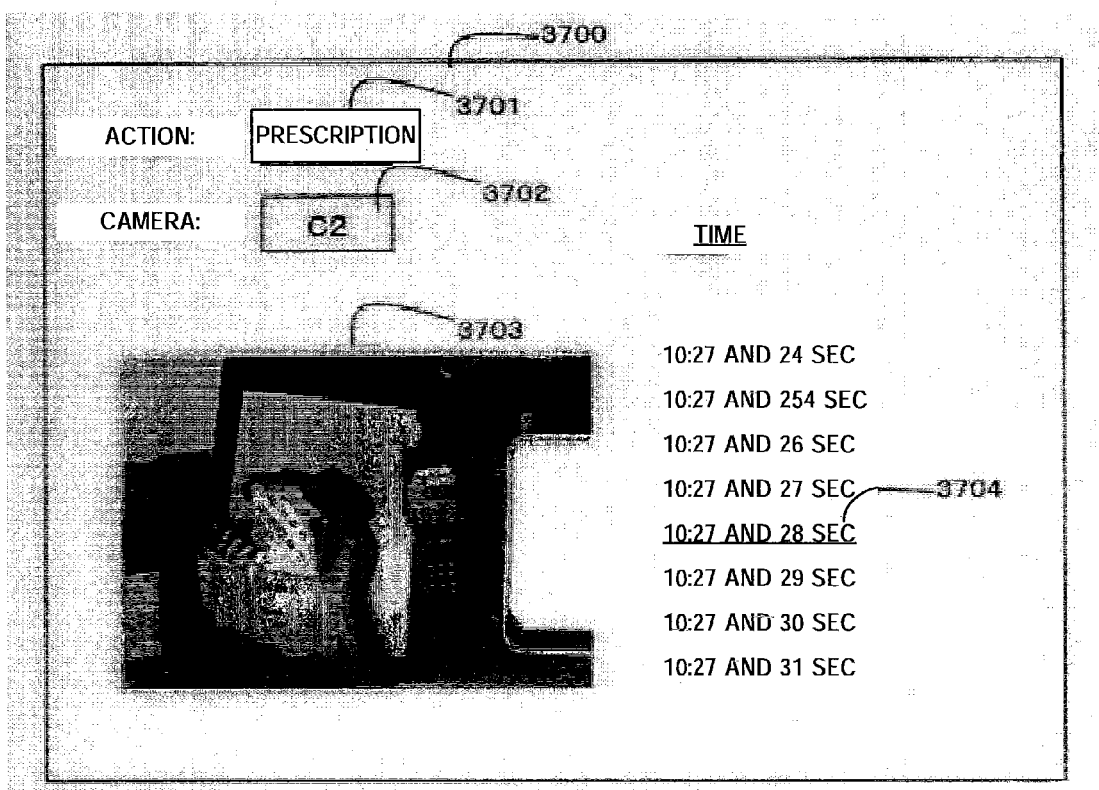
FIG. 37 is a diagram showing a screen on which is displayed monitoring data shown by the image region in FIG. 36.

FIG. 37 shows a screen which displays monitoring data shown in the image region 3602 in FIG. 36. The action of the monitoring object is the "Prescription" displayed in the image region 3701, and the camera terminal ID is "C 2" displayed in image region 3702. C 2 is a terminal ID which shows the monitoring camera of a prescription location. The image region 3703 is an image at a time shown in 3704. Here, the list displayed "time" is in HTML text, and by adding the additional appropriate action of clicking or the like, the image of a desired time can be displayed.

Figure 38:
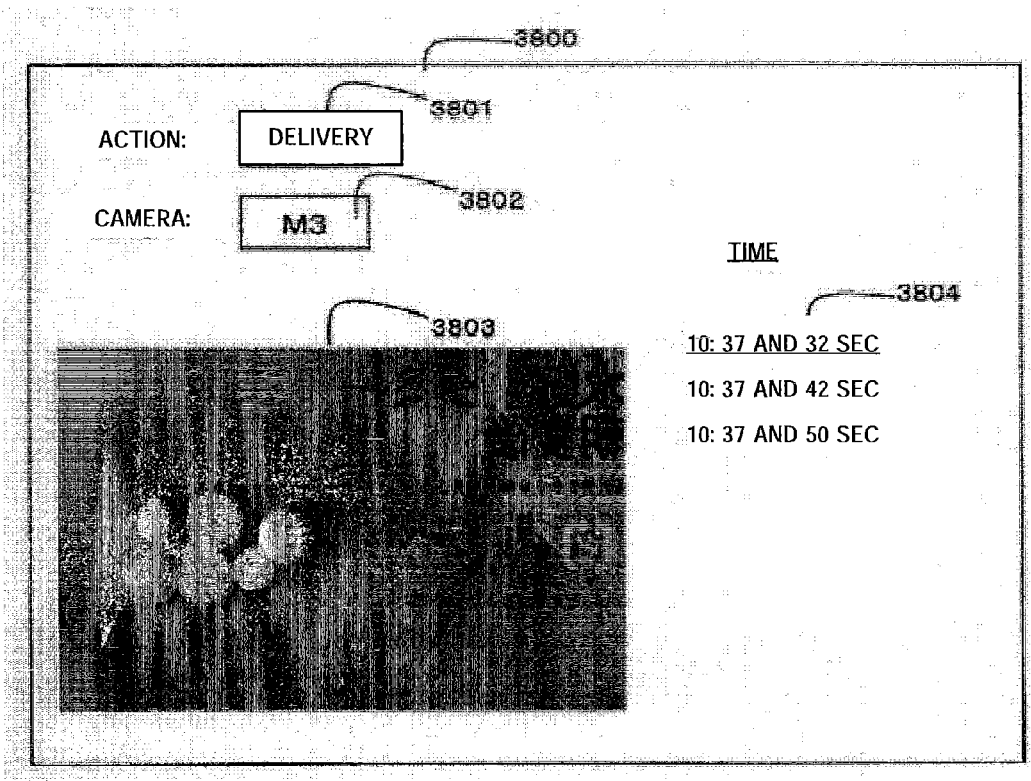
FIG. 38 is a diagram showing a screen on which is displayed monitoring data shown by the image region in FIG. 36.

FIG. 38 shows a screen which displays the monitoring data shown in image region 3603 in FIG. 36. The action of the monitoring object is the "Delivery" displayed in the image region 3801, and the camera terminal ID is the "M3" displayed in image region 3802. M 3 is a terminal ID which shows the magnifying glass of the delivery location. Image region 3803 is a magnified image monitored by the operator at the time shown in the image region 3804. Here, the list displayed "Time" is HTML text, and by adding the appropriate action of clicking and the like, the magnified image of the desired time can be displayed.

Embodiment 3

(Unique ID Entry Format)

Figure 39:
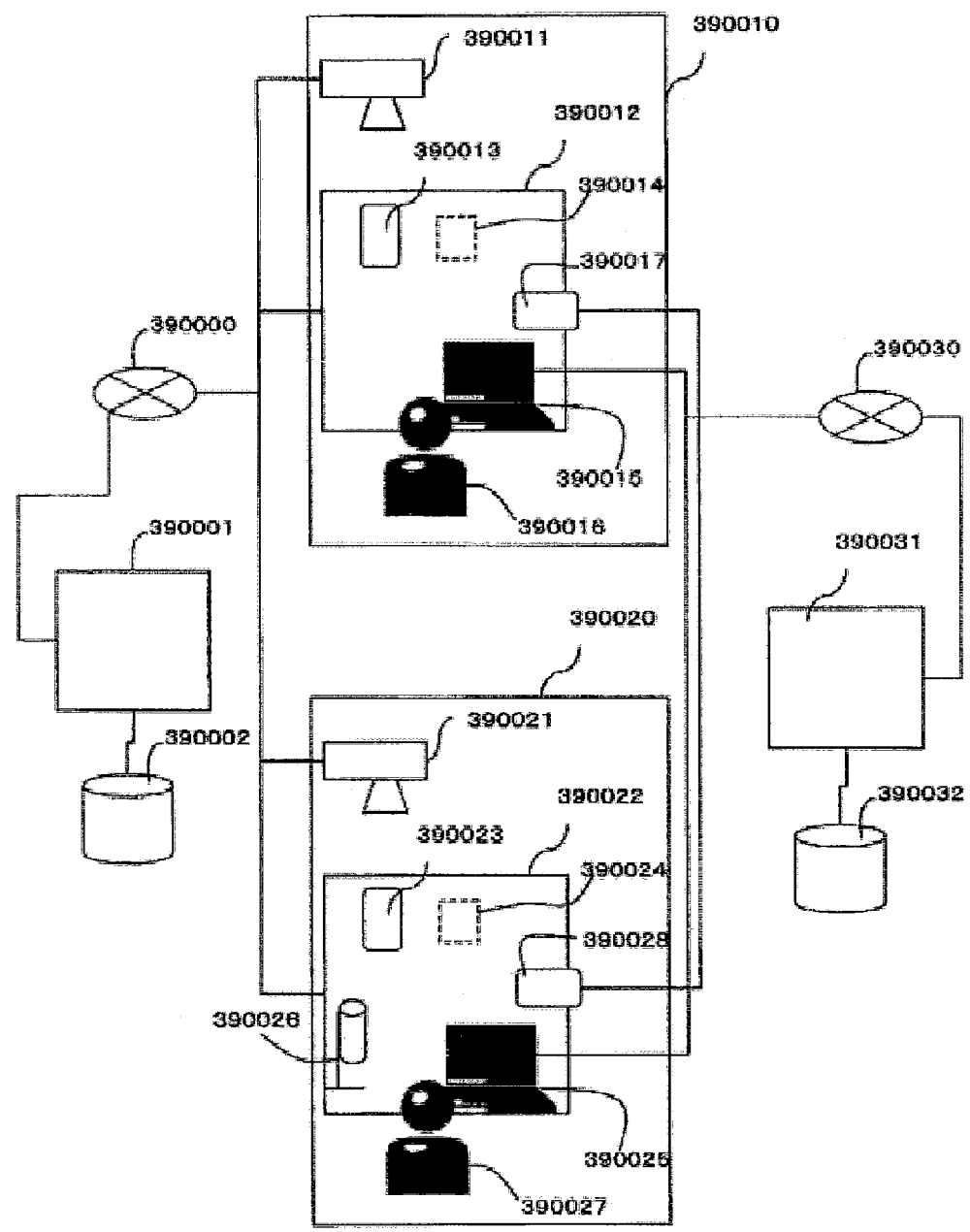
FIG. 39 is a summary composition diagram of a monitoring system relating to embodiment 3.

Next, an explanation is provided of a monitoring system relating to embodiment 3 of the present invention. FIG. 39 is a summary composition diagram of the monitoring system relating to embodiment 3 of the present invention. This is an embodiment form in the case of introducing reception, prescription location, delivery location, and accounting in a system in a pharmacy. The monitoring system is composed from a network 390000, a monitoring system server 390001, and a monitoring data storage device 390002, comprising tasks which are the monitoring objects performed in a first type of work area 390010, a second type of work area 390020, a network 390030, a task system server 390031, and a task data storage device 390032.

Shown here are the two convenient work areas 390000 and 390030, composing one network and a mutually connected substantially single network.

In addition, the explained convenient two types of work areas are displayed one at a time. The first type of work area 390010 is adopted in the reception location and accounting location, the second type of work area 390020 is adopted in the prescription location and the delivery location; therefore, there are a total of four respective work areas, handled two at a time.

Furthermore, the work areas of the present invention is not limited to each type two at a time, but are composed as the appropriate selection of one or two types of work areas corresponding to the scale of the introduced pharmacy or operation, and/or the number of work areas, and there may be only one type of work area, or multiple numbers may also be received.

The composition of the first type of work area is as follows. A monitoring camera 390011 and workbench 390012 are arranged, and a monitoring camera 390011 is set to photograph tasks while the operator 390016 is facing the workbench. Here, to the workbench 390012 is attached an RFID reader/writer 390013 managed in the monitoring system server through the network, and upon placing a document holder 390014 which has an RFID tag in its detection area, a specific trigger signal is transmitted. The operator 390016 performs tasks relating to compounding, and enters tasks in the personal computer terminal 390015 connected to the monitoring system server through the network. Furthermore, a transmission device 390017 connected to the network for transmitting a prescription ID comprising the unique ID described hereafter, is provided.

Here, as the transmission device, adopted is a QR code and handy scanner displayed on a task data display screen of the monitoring system or in the operating manual, the prescription ID which is the unique ID of tasks from the displayed QR code is scanned, and transmitted to the link controller of the monitoring system server.

The composition of the second type of work area is as follows. A monitoring camera 390021 and workbench 390022 are arranged, and a monitoring camera 390021 is used by an operator 3900272 to photograph tasks while facing the workbench. Here, to the workbench 390022 is attached an RFID reader/writer 390023 and a magnifying glass 390026. Upon arranging a document holder 390024 which has an RFID tag in the detection area of the RFID reader/writer, a specific trigger signal is transmitted. A magnifying glass is connected to the network, and the operator sets the subject object in the photographic parameters of the magnifying glass, or faces the magnifying glass to the subject object, and by operating a switch (not shown in the drawing), a magnified image can be acquired.

Here, the magnified image is used for confirmation of the task object by the operator by means of a monitor (not shown in the drawing), along with being transmitted to the monitoring system server via the network.

The operator 390027 performs tasks relating to compounding, and task input to a personal computer terminal 390025 connected to the task system server. Connected to the network, a provided transmission device 390028 for transmitting a prescription ID comprising the unique ID is explained hereafter.

Here, as the transmission device, a QR code and handy scanner displayed on the task data display screen of the task system is adopted, the prescription ID which is the unique ID of the task is scanned from the QR code of the display, and transmitted to the link controller of the monitoring system server.

Furthermore, as the transmission device of the present invention, here, a combined handy scanner and QR code is adopted, however, the transmission device of the present invention is not limited to this, and transmission of the unique ID may also be used by entering the RFID tag only when it is linked, by adopting a separately prepared RFID writer for transmission use.

Here, although not explicitly shown because of the simplified drawing, the monitoring system server 390001 and task system server 390031 are both connected to and are capable of mutually accessing the network.

Furthermore, the composition of the system shown here is nothing more than an example, and an appropriate composition is possible corresponding to the established object and/or specific hardware. For example, task input was made to a personal computer terminal; however, the task input of the present invention is not limited to this. It is possible to do so through an appropriate dedicated terminal or the like corresponding to the scale of the pharmacy.

In addition, the actions of each functional "unit" of the monitoring system server for task system server in the explanation which follows are executed by a prepared program with a personal computer or the computer of a workstation or the like provided with the interface of a monitor, keyboard, or mouse or the like, and realized by controlling each type of device. In addition, these programs are recorded on and capable of being read by a computer from the recording medium of a hard disk, USB memory, CD-ROM, MO or DVD and the like, executed by the operation of the system user.

Figure 40:
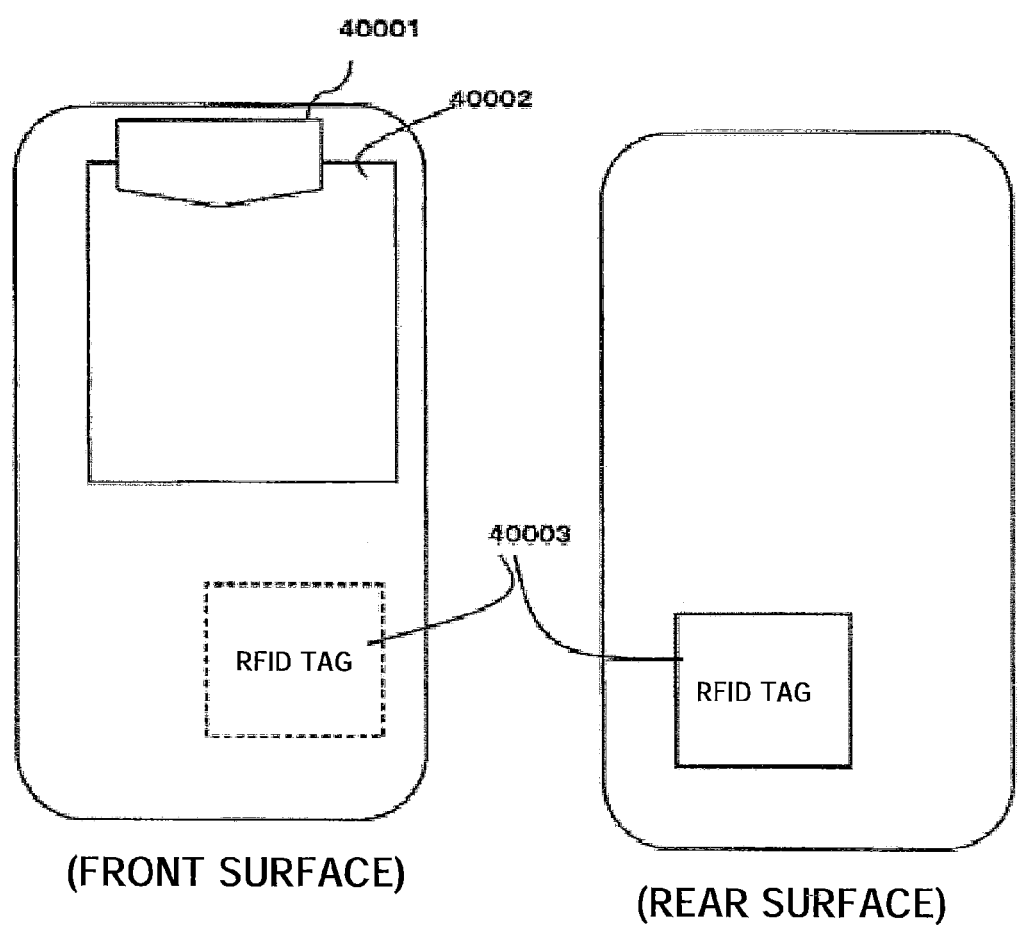
FIG. 40 is a diagram showing the composition of a document holder.

FIG. 40 is a diagram showing the composition of document holders 390014 and 390024 adopted by the present invention. Document holders 390014 and 390024 are prepared one for each single task, and the instructions for the action of the task are contained in documents such as the task manual of instructions and the like, which are carried to each work area along with the task progression. In the specific position of the workbench, the tasks are performed while referring to the instruction items maintained in the document holders 390014 and 390024. Document holders 390014 and 390024, are composed, for example, of a clip 40001 which holds the task instructions or the like, action instruction document 40002, and RFID tag 40003. Upon placing the document holder on the workbench, the RFID tag is detected by the RFID readers 390013 and 390023 attached to the workbench. The progress of the task is detected from the detection/non-detection pattern, and image information of the sequence of task progress is acquired by sending a trigger signal to activate the monitoring camera. Control of the monitoring camera is already known, as recorded in Patent Literature 1.

Data stored by the RFID tag includes data items of temporary ID and unique ID. These data items are freely entered by the specific RFID reader/writer, and in preparing the temporary ID items in advance of the commencement of a task, appropriately created unique ID is entered with the date and time and the like. At this point in time, there is no ID information in the unique ID, and a "Null" signal is returned relative to inquiries relating to the unique ID.

Figure 41:
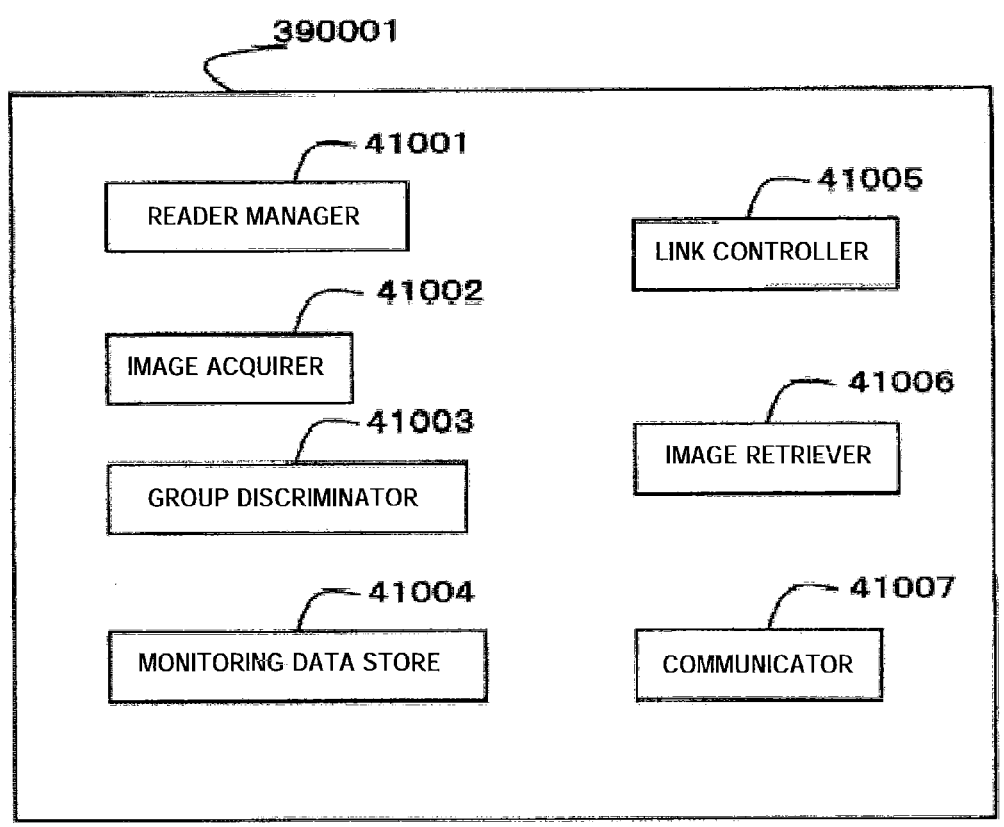
FIG. 41 is a diagram showing the internal composition of a monitoring system server.

FIG. 41 is a diagram showing the internal composition of the monitoring system server 390001 of the present invention. The monitoring system server 390001 is composed from a reader manager in 41001 which manages the detection action of the RFID reader, an image acquirer 41002 which acquires image information sent from the monitoring camera, and creates/assigns index information, a group discriminator 41003 which discriminates and groups task sequence/groups, a monitoring data store 41004 which stores monitoring data in a specific location, a link controller 41005 which detects a prescription ID (unique ID) entered from the task system server, and records it in written form to the unique ID item preset in the monitoring data, the image retriever 41006 which receives the input of the specific key information and calls out monitoring data, and a communicator 41007 which controls the communications action on the network for the actions of each of these functional units.

Here, the monitoring data is composed from a temporary ID comprising the information read out from the detected RFID tag, a unique ID, date, time, the index information generated from the information of the location of the monitoring camera and image information from the monitoring camera. Also, the monitoring data, depending upon whether it is acquired within the specific effective deadline from initial RFID tag detection, and after discriminating if it belongs to a single task sequence/group, is assigned a specific group ID. Here, a monitoring camera terminal ID is adopted as the location of the monitoring camera; however, the location of the monitoring camera of the present invention is not limited to this, and, for example, may be an RFID reader terminal or the like, which sends a trigger signal to activate the monitoring camera.

(Corporative Action of Each Functional Unit in the Monitoring System Server)

Figure 42:
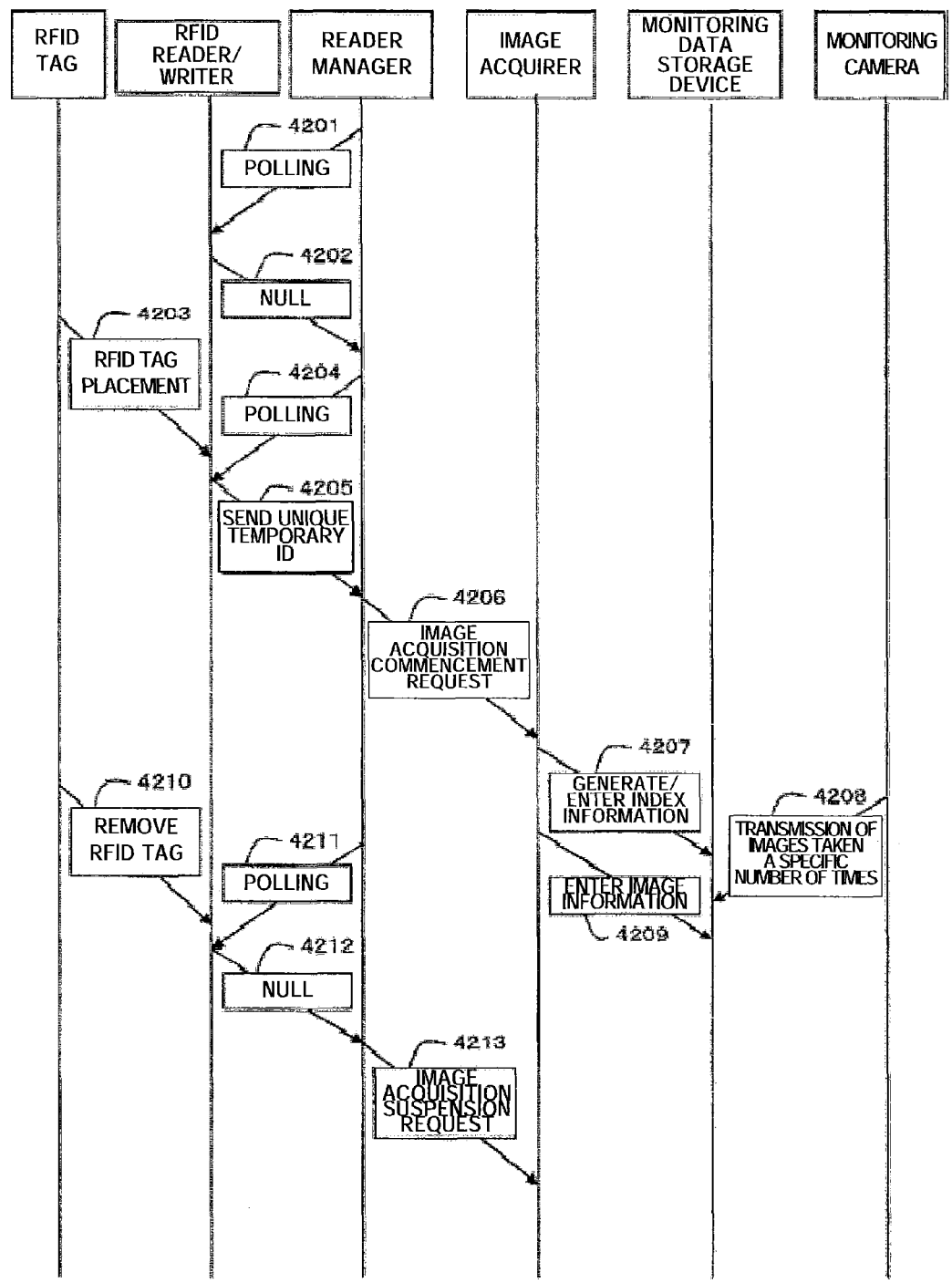
FIG. 42 is a sequence diagram showing the cooperative operation stored in a monitoring data storage device.

FIG. 42 is a sequence diagram showing image acquisition, creation of monitoring data, and the cooperative action by means of each functional unit/device of a reader manager and the like showing the action stored in the monitoring data storage device 390002.

First of all, in step 4201, polling is performed relative to the RFID reader/writer by the action of a reader manager which executes a specific link control program. Here, in the absence of a transmission request, in step 4202, a "Null" signal is returned. In step 4203, upon placing an RFID tag within the specific detection parameters, the unique temporary ID of step 4205 is transmitted relative to the polling of step 4204. The temporary ID is a unique ID pre-stored in the memory of the RFID tag as indicated above. The reader manager which receives the temporary ID signal, in step 4206, requests image acquisition relative to the image acquirer. The image acquirer, in step 4207, generates index information, and enters it to the monitoring data storage device. An explanation of the generation of this index information is described hereafter.

In addition, the monitoring camera, in step 4208, transmits image information of a specific amount to the monitoring data storage device. In step 4209, the image acquirer, enters image information to the storage location of the monitoring data into which index information had been entered in the previous step.

In step 4210, upon removing the RFID tag from within the specific detection parameters, in step 4212, a "Null" is returned relative to the polling of step 4211. The reader manager which returned the "Null", in step 4213, sends a request for the termination of image acquisition relative to the image acquirer.

(Generation of Index Information)

Figure 43:
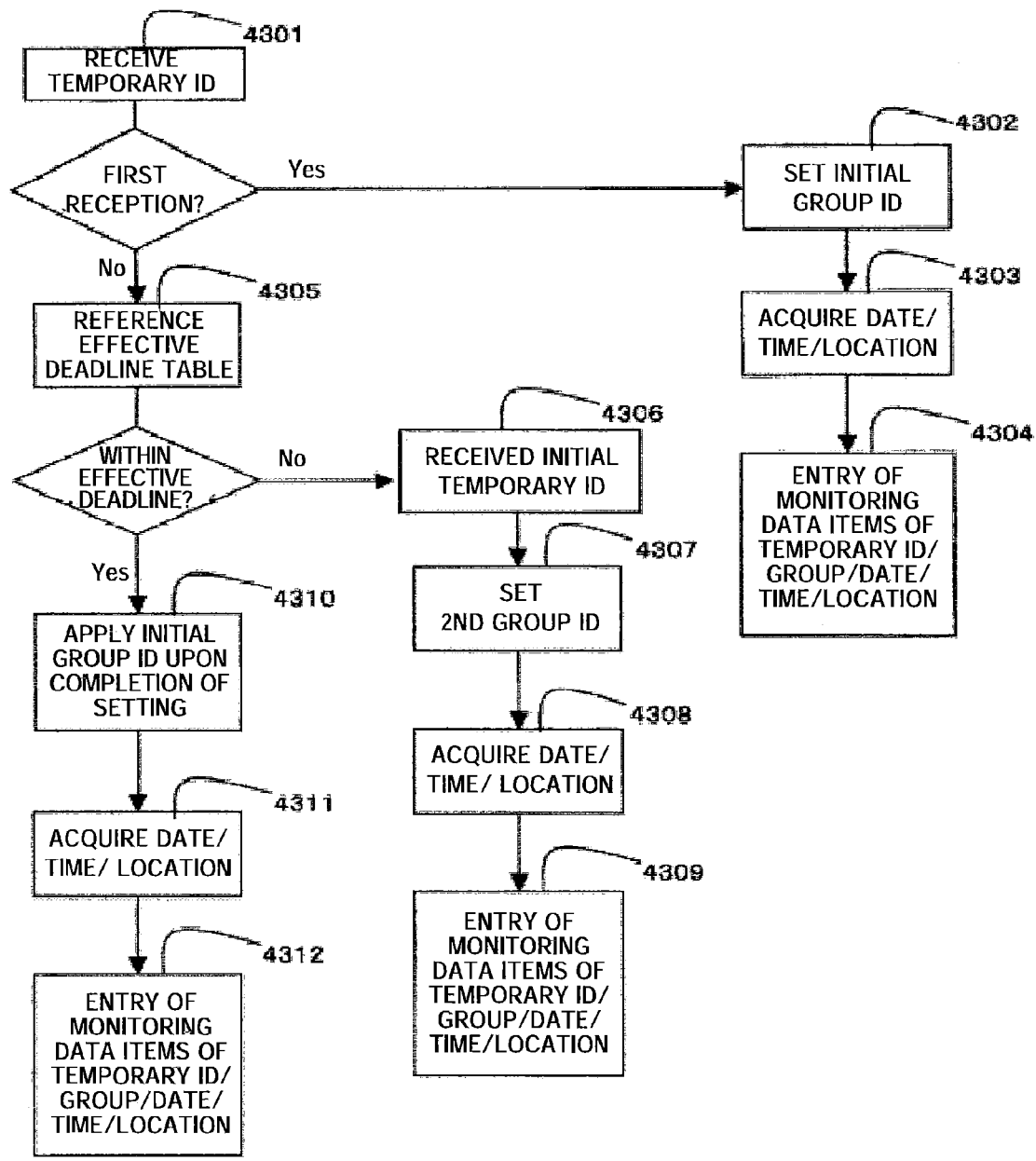
FIG. 43 is a flowchart which explains the operation of the generation/entry of index information.

FIG. 43 is a flowchart explaining the generation/entry action of index information in step 4207 of FIG. 42.

In step 4301, the image acquirer receives the temporary ID sent from the reader manager. Also, the image acquirer queries the monitoring data even for a temporary ID used as index information relative to the monitoring data storage device, and discriminates if it is an initial reception.

If the discrimination results are "Yes", in other words, if there is an initial reception, in Step 4302, the image acquirer establishes the initial group ID. Next, the image acquirer, in Step 4303, acquires the date, time and location information relating to the detection of a temporary ID. Here, the location information is a monitoring camera terminal ID, and by means of the terminal ID, the hardware can be specific.

Furthermore, here, adoption is made of the monitoring camera terminal ID as the location of the monitoring camera. However, the location of the monitoring camera of the present invention is not limited to this, and, for example, may also be the RFID reader/writer terminal ID which transmits a trigger signal activating the monitoring camera.

Also, in Step 4304, the image acquirer the image acquirer enters each item of the acquired group ID, date, time, location and temporary ID corresponding to the pre-established monitoring data.

If the results of discrimination are "No", in other words if they are the temporary ID relating to the already set monitoring data, the image acquirer, in step 4305, references a specific effective deadline table. Also, if not within the effective deadline, the image acquirer, in step 4306, receives the initial provisional ID, and in step 4307, a second group ID is set, which is different from the group ID which had already been set. Next, in step 4308, the image acquirer acquires information of date, time, and location relating to the detection of the provisional ID. Also, in step 4309, the image acquirer enters each item of the set or acquired group ID, date, time, location and provisional ID corresponding to the preset monitoring data.

In step 4305, referencing the specific effective deadline table, if within the effective deadline, then in step 4310, the image acquirer assigns a preset initial group ID. Next, in step 4311, the image acquirer acquires information of information of date, time, and location relating to the detection of the temporary ID. Also, in step 4312, the image acquirer enters each item of assigned or acquired group ID, date, time, location and temporary ID corresponding to the preset monitoring data.

Here, setting the group ID, a format is adopted for setting group items in each monitoring data. However, the invention relating to the task sequence/group of the present invention is not limited to this, and the monitoring data belonging to the same task sequence/group is registered in the management table set for each group, without setting the data items relating to the group in the monitoring data, and a group management format may also be used.

FIG. 44 is a summary diagram comparing the grouped formats, and shows a monitoring data storage device which shows monitoring data 4402 stored in the monitoring data storage device 4401 relating to a format which established group ID items in the monitoring data, and which registers monitoring data relating to the same task sequence, without setting the group ID items in the monitoring data storage device 4403, in the management table 4405, and which stores monitoring data 4404 without setting the group ID.

(Effective Deadline Table)

FIG. 45 shows the composition of the effective deadline table referenced in step 4305 of FIG. 43. Here, there are cases which are effective within three hours from reception of the initial temporary ID. The effective deadline table is a table formed from the addition of the "reception of the initial temporary ID" each time it is recognized. The items of the effective deadline table are formed from the received temporary ID, the day relating to initial reception, the time relating to initial reception, the effective deadline, and the group ID. Referencing this table, the image acquirer assigns the same group ID concerning monitoring data relating to the same temporary ID within the effective deadline. Data shown in table 4501 and 4502 also has the temporary ID "200910230922"; however, monitoring data after the passage of the effective deadline of the task sequence of "g1", is recognized as being a different task sequence, and a second group ID, "g8" is set which is different from the initial "g1".

Figure 46:
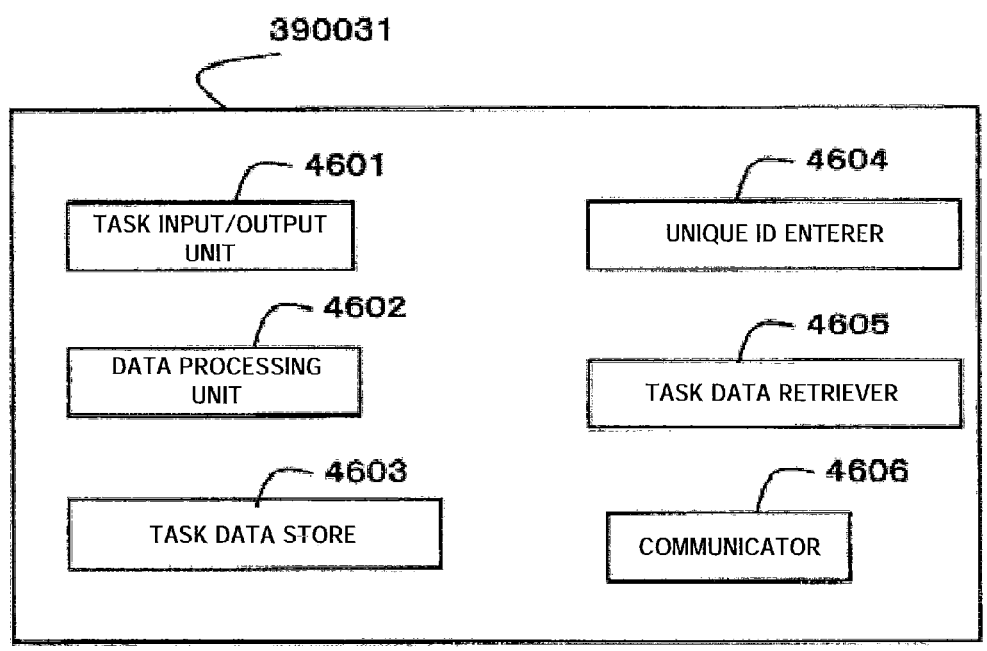
FIG. 46 is a diagram showing the internal composition of a task system server.

FIG. 46 is a diagram which shows the composition within the monitoring system server 390031 of the present invention. Task system server 390031 is composed from a communicator 4606 which controls the communications activity on the network for the actions of each functional unit comprising a task input output unit 4601, a data processing unit 4602 which processes the task input task information in the format of task data, a task data store 4603 which controls storage of task data in the task data storage device 390032, a unique ID enterer 4604 which enters the unique ID included in the task data during processing, in the RFID tag, and the monitoring data retriever 4605 which controls retrieval of task data by means of specific key information input.

Here, the unique ID handled by the unique ID enterer 4004 is the prescription ID relating to the task data during handling by the task system, and the prescription ID, through the entry action of the execution of a specific program, provides entry to preset items as index information of monitoring data. By the key retrieval of a prescription ID, corresponding monitoring data can be called out, and a linkage established between the monitoring data and the task data.

(Action of Linking Monitoring Data and Task Data)

Figure 47:
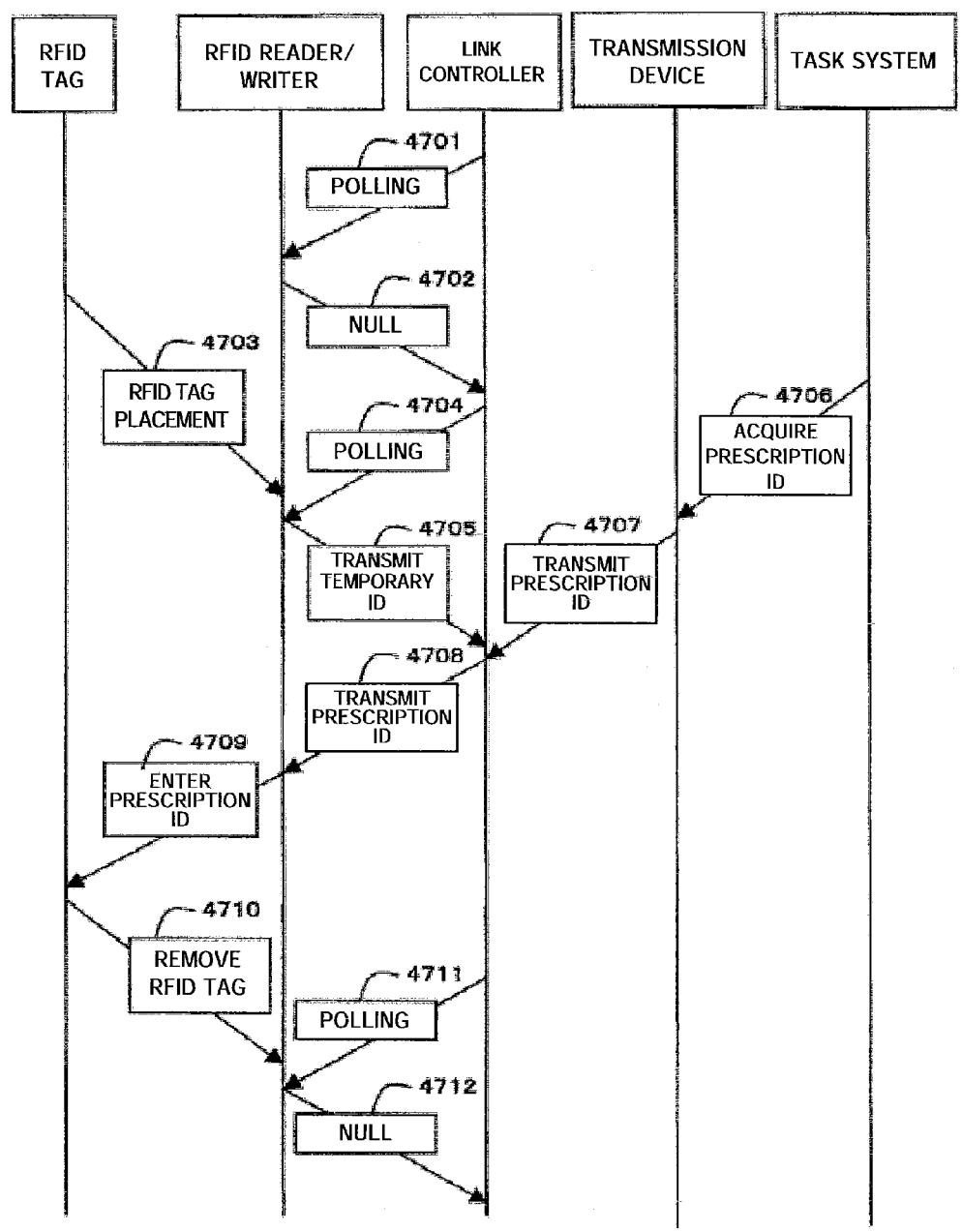
FIG. 47 is a sequence diagram showing the link attachment operation of a monitoring system server.

FIG. 47 is a sequence diagram showing the linkage controller of the monitoring system server, a transmission device, and the linking action cooperatively performed by the task system or the like.

First of all, in step 4701, by means of the action of the linkage controller which executes a specific linkage control program, polling is performed relative to an RFID reader/writer. Here, in the absence of a transmission request, in step 4702, a "Null" signal is returned.

In step 4703, upon placing the RFID tag within specific detection parameters, polling is subsequently performed in step 4704. Also, in step 4705, the transmission of a temporary ID is received from the RFID reader/writer, and becomes a standby state waiting for entry. In the standby state, in step 4706, by scanning a QR code displayed on a task data screen relating to tasks being handled by the task system by means of a transmission device scanner, a prescription ID comprising a unique ID is acquired.

Next, in step 4707, the prescription ID is sent to the linkage controller of the standby state from the transmission device.

In step 4708, the link controller transmits a prescription ID relative to the RFID reader/writer.

The RFID reader/writer, in step 4709, executes entry of the prescription ID to the unique ID of the RFID tag, following the program of the link controller.

Also, in step 4710, if the RFID tag is removed from within the specific detection parameters, then in step 4712, a "Null" signal is returned relative to the polling of step 4711.

Figure 48:
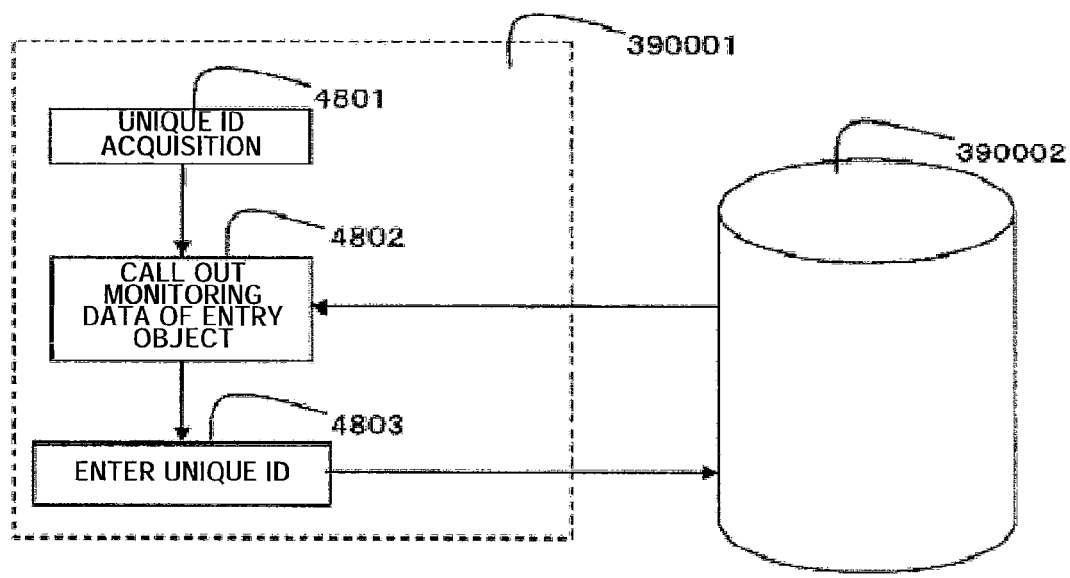
FIG. 48 is a flowchart showing the entry of a prescription ID.

FIG. 48 is a flowchart which shows the prescription ID entry relative to the monitoring data of where the link controller's acquisition of step 4706 of FIG. 47 is completed and the value of unique ID remains "Null".

Step 4801 is a step corresponding to step 4706. The monitoring system server, in step 4801, receives the transmission of the prescription ID composing the unique ID from the transmission device. Next, in step 4802, by referring the acquisition completed temporary ID as the retrieval key, the monitoring system server calls out the monitoring data forming the entry object. Also, in step 4803, the monitoring system server enters the prescription ID in the unique ID items of the developed monitoring data called out from memory (not shown in the drawing) of the monitoring system server, and stores it in the monitoring data storage device 390002.

Here, the prescription data is received, and at the time of step 4706 of FIG. 47, the acquisition completed monitoring data which has a common temporary ID is called out, made to be the entry format, and a unique ID reference table is created which establishes a relationship between the temporary ID and the prescription ID composing the unique ID, which may be entered as a bundle when a load on the system is light.

FIG. 49 is an example of the unique ID reference table. As shown in the same drawing, the temporary ID and unique ID are given an established correspondence, and are stored.

Figure 50:
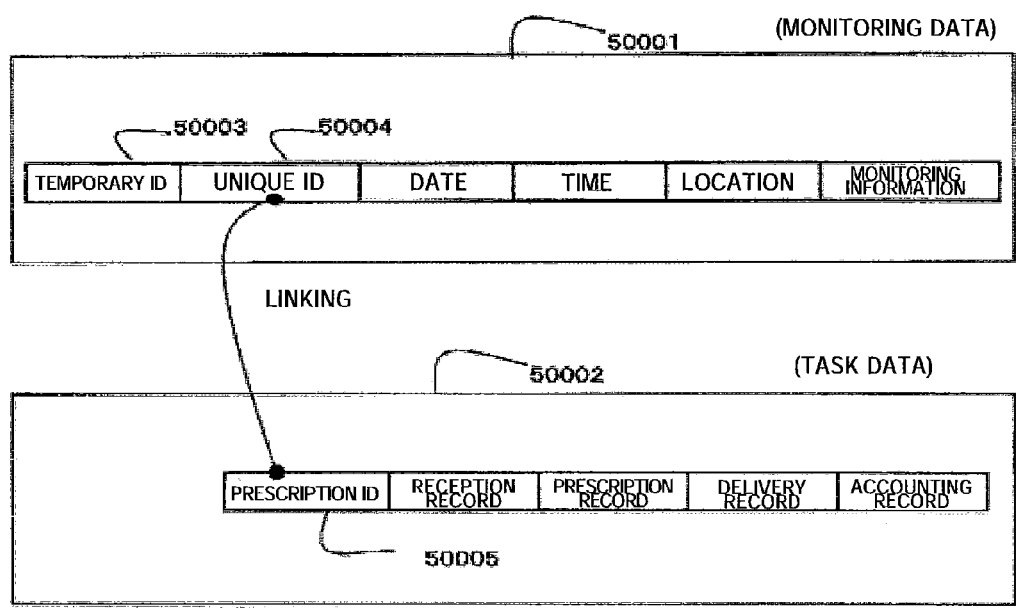
FIG. 50 is a diagram showing the composition of task data and monitoring data.

FIG. 50 is a diagram showing the composition of the task data and monitoring data after the entry of the unique ID. The monitoring data 50001 is composed from data items of temporary ID, unique ID, date, time, location and monitoring information. Here, the monitoring information is image information acquired by a monitoring camera. In addition, the temporary ID 50003 is a unique ID created in an appropriate format from the date and time in preparing the document holder used in the task 50004 is a unique ID, and, in the task system, is a data item in which is entered task data or prescription data or the like in which tasks are uniquely specific.

In addition, task data 50002 is composed from data items of prescription ID, reception record, prescription record, delivery record and accounting record. Here, the reception record and the like summarily suggest items relating to task information, and detailed or specific items are established corresponding to the task need.

The unique ID 50004 of the monitoring data and the prescription ID 50005 of the task data are items for which a link is formed between the monitoring data and the task data, and in examining the prescription ID using the unique ID item value as a retrieval key, the monitoring data of tasks relating to task data can be called out.

Here, one monitoring data and task data are conveniently shown in the diagram, however, data handled by the present invention is the bundling of multiple data, for which links are established.

Figure 51:
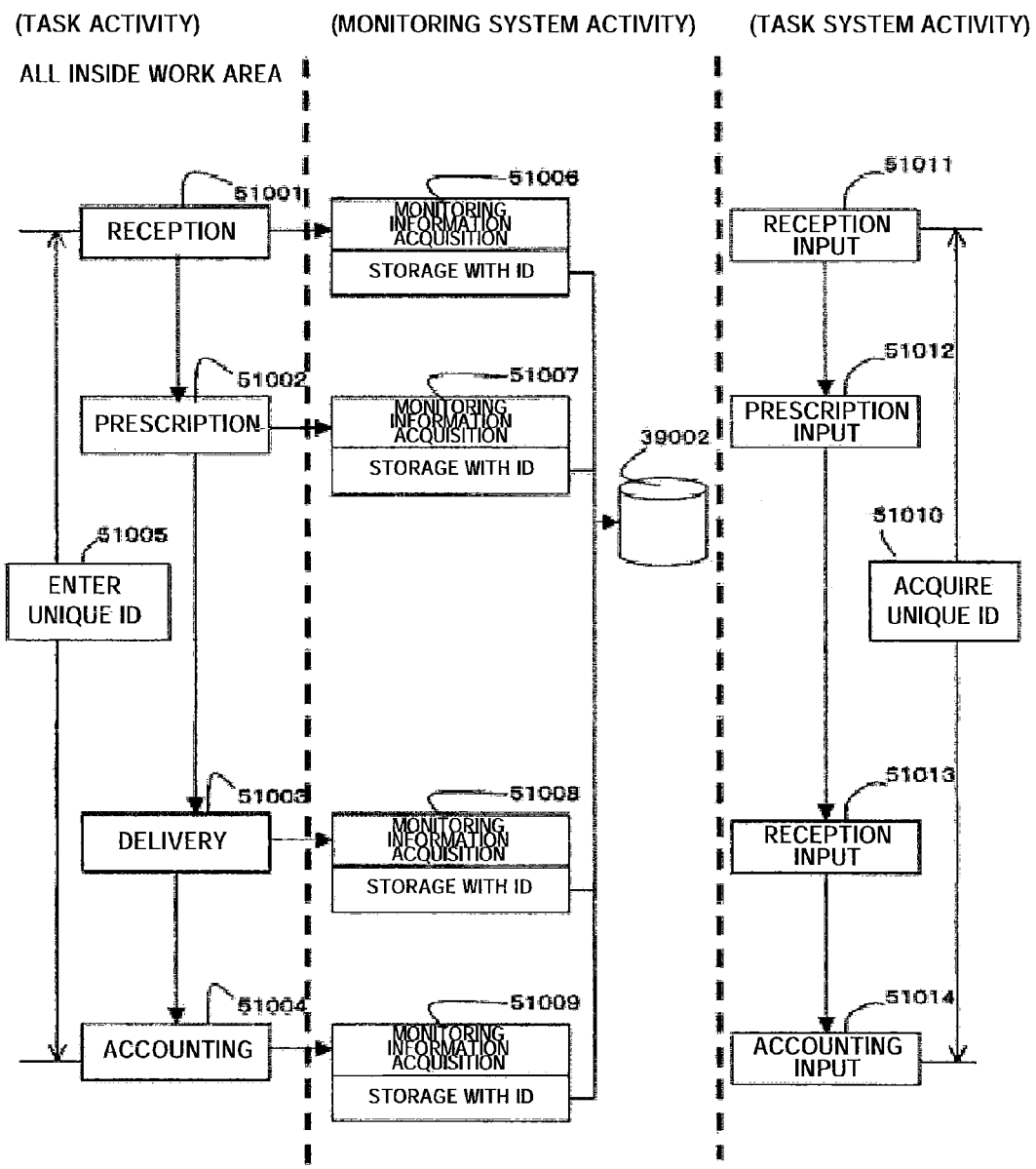
FIG. 51 is a sequence diagram showing the entire operation of a system.

FIG. 51 is a sequence diagram showing the action of the entire system of embodiment 3. Here, tasks which are the object of monitoring performed within the work area and outside of the work area, and actions of the monitoring system relating to monitoring within the work area, composing the three activities of the task system are arranged in a chronological timeline.

First of all, prior to the commencement of a task in the work areas, a document holder is prepared which is provided to the task. As storage information of the RFID tag, a temporary ID item and unique ID item are established. In the temporary ID item, is stored a unique ID created by the previously described method. The unique ID item becomes "Null" data. This action is outside of the monitoring object of the monitoring system. Furthermore, the monitoring date of this task step is not managed by the embodiment system.

Here, a document holder is adopted as the RFID attachment; however, appropriate adoption may also be provided to task without being limited to the document holder.

An explanation is provided of the action of both the monitoring system server and task system server corresponding to the chronological timeline. Furthermore, the monitoring camera, operator and personal computer terminal, in regard to the convenient composition of the same type of work area, use the same writing, and while these are actually not the same things, the compositional elements of the system are nothing more than being the same in terms of the monitoring object.

Here, step 51005 is a step in which entry is made of the prescription ID as the unique ID accomplished by selecting a point in time, where there are a few additions, and is the reception step of any of steps 51001-51004, corresponding to the nature of the task. In step 51005, use is made of the prescription ID required by the transmission device in step 51010 which acts with the same timing.

Step 51001 is a reception step. In the reception location, the composition is adopted of the first type of work area 390010 shown in FIG. 39. At this time, the action of the task system server, in step 51011, receives input, and the receiver, as the operator, performs reception tasks relative to patients coming to the pharmacy, and performs reception input from a personal computer terminal. At this time, the monitoring system server, in monitoring information acquisition step 51006, acquires image information of tasks photographed by the monitoring camera 390011, and if, at this point in time, step 51005 is executed, index information is generated which includes a temporary ID and a unique ID. On the other hand, if prior to execution, the monitoring system server generates index information which includes the temporary ID, and generates monitoring data by adding index information to the image information. Also, the monitoring system server discriminates the task sequence/group, and stores the monitoring data in the specific location of the monitoring data storage device 390002.

Here, step 51002 is a prescription step, and is a composition of the second type of work area 390020 provided with the magnifying glass 390026 shown in FIG. 39. The action of the task system server at this time, in step 51012, receives the prescription input, and the pharmacist, acting as the operator, provides prescriptions for patients and the like as described in the instruction manual, and provides prescription input from a personal computer terminal. At this time, the monitoring system server, in monitoring information acquisition step 51007, acquires image information of tasks photographed by the monitoring camera 390021, and if entry is executed of step 51005 at this point in time, index information is generated which includes a temporary ID and a unique ID. On the other hand, if prior to execution, the monitoring system server generates index information which includes the temporary ID, and monitoring data is generated by adding the index information to the image information. Also, the monitoring system server, discriminates the task sequence/group and stores the monitoring data in a specific location of the monitoring data storage device 390002. Here, in the case where the operator performs detailed monitoring of the task object, the magnifying glass 390026 is operated, and magnified images are acquired. The acquired magnified images are sent to the monitoring system server, and by executing a specific program to process the image from the magnifying glass provided in the image acquirer, index information is added relating to the RFID tag during detection, and is stored in a specific location of the monitoring data storage device 390002 as monitoring data.

Figure 52:
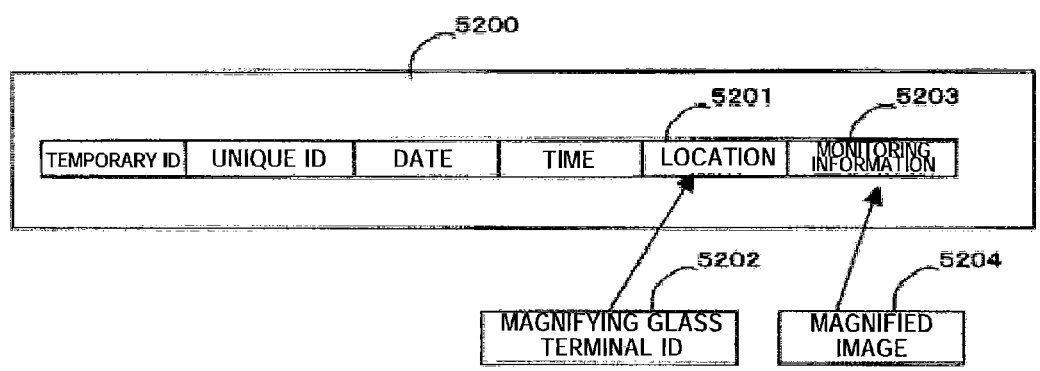
FIG. 52 is a diagram showing the composition of monitoring data relating to a magnified image.

FIG. 52 shows the composition of monitoring data relating to a magnified image. The monitoring data 5200 relating to a magnified image is composed from data items of a temporary ID, unique ID, date, time, location and monitoring information and is the same as monitoring data relating to image information from the monitoring camera. In location 5201, entry is made of the magnification glass terminal ID 5202, and the magnified image 5204 is stored in the monitoring information 5203. The storage/retrieval of monitoring data is executed by the same action as for monitoring data relating to the images of the monitoring camera. In addition, discrimination of the task sequence/group is also the same, and a group ID may also be established as the data item of monitoring data in accordance with the need.

Step 51004 is a delivery step. This is a composition of the second type of work area 390020 provided with the magnifying glass 390026 shown in FIG. 39. At this time, the action of the task system, in step 51013, receives input, and the deliverer, acting as the operator, performs delivery tasks relative to patients and the like who come to the pharmacy, and performs delivery input from the personal computer terminal.

At this time, the monitoring system server, in monitoring information acquisition step 51008, acquires image information of tasks photographed by the monitoring camera 390021, and if entry is accomplished of step 51005 at this time, index information is generated which includes a temporary ID and unique ID. On the other hand, if prior to execution, the monitoring system server generates index information which includes a temporary ID, and monitoring data is generated by adding the index information to the image information. Also, the monitoring system server discriminates the task sequence/group, and stores it in a specific location of the monitoring data storage device 390002. Here, in the case where the operator performs detailed monitoring of the task object, the magnifying glass 390026 is operated, and the magnified image is acquired. The acquired magnified image is transmitted to the monitoring system server, and by executing a specific program which processes images from the magnifying glass provided in the image acquirer, index information relating to the RFID tag during detection is added, and stored as monitoring data in a specific location of the monitoring data storage device 390002.

Step 51005 is an accounting step. In the accounting location, shown in FIG. 39, adoption is made of the composition of a first type of work area 390010. At this time, the action of the task system, in step 51014, receives accounting input, and the accountant, acting as the operator, performs accounting tasks relative to patients who come to the pharmacy, and performs accounting input from the personal computer terminal.

At this time, the monitoring system server, in monitoring information acquisition step 51009, acquires the image information of tasks photographed by the monitoring camera 390011, and if entry is accomplished of step 51005 at that point in time, index information is generated which includes a temporary ID and unique ID. On the other hand, if prior to execution, the monitoring system server generates index information which includes a temporary ID, and monitoring data is generated by adding index information to the image information. Also, the monitoring system server discriminates the task sequence/group, and stores them in a specific location of the monitoring data storage device 390002.

(Tracking)

Figure 53:
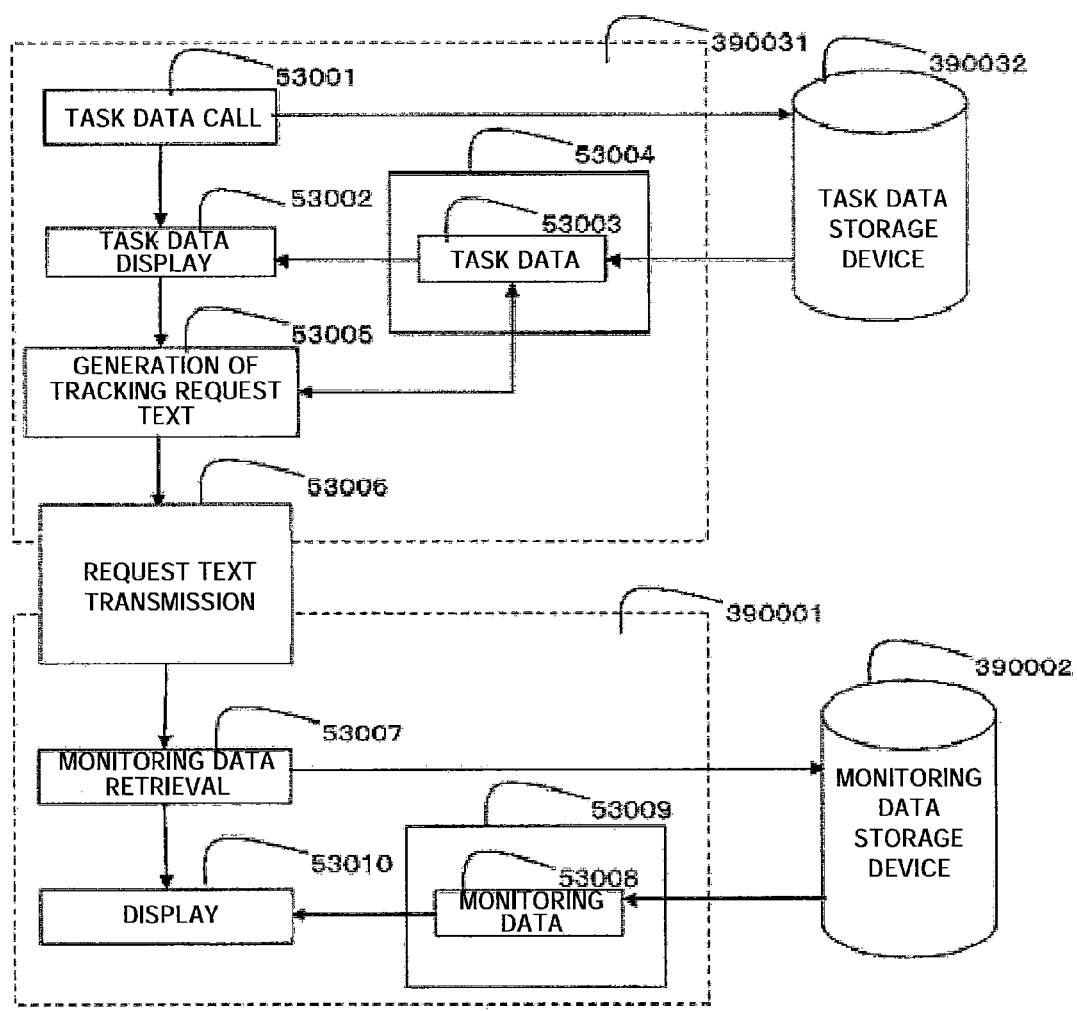
FIG. 53 is a flowchart showing the operation in the case of performing tracking.

FIG. 53 is a flowchart which shows activity in the case of generating problems concerning task data handled by the task system, and activity in the case of accomplishing confirmation tracking Here, the action of the regional step 390031 shown by the broken line is the action of the task system server. In addition, the action of the 3900001 region shown by the broken line is the action of the monitoring system server.

In step 53001, the task system server calls out desired task data relative to a task data storage device 390032 in a known format for the key input of patient names and the like. The object of task data 53003 is developed in work region 53004 maintained in the task system server memory (not shown in the drawing), and can be processed in real time, and in step 53002 is displayed in a specific format on a monitor (not shown in the drawing).

In the next step 53005, the task system server generates tracking request text which includes a retrieval key required for monitoring data retrieval from the data items of the task developed in the work area. Also, in step 53006, the generated request text is sent to the monitoring system server.

In step 53007, the monitoring system server extracts the retrieval key from the received request text, and performs extraction of monitoring data. The retrieval key, in the format described below, indicates the data item and the item value. The value of the unique ID is a key indicated as a prescription ID item value. For example, it is indicated as the value of the data item examined with the format of (the value of the prescription ID and unique ID).

In step 53010, the monitoring system server, in the work region 53009 of the memory (not shown in the drawing) of the monitoring system server, is retrieved, called out, and displayed the developed monitoring data 53008. The monitoring data called out here conveniently records one data; however, this is everything which belongs to the same task sequence/group. Since each monitoring data sets the group ID, and the group ID is managed, calling out and displaying can be performed for each group. In this manner a link is formed which directly calls out monitoring data from the task data, with the effective realization of high traceability.

Figure 56:
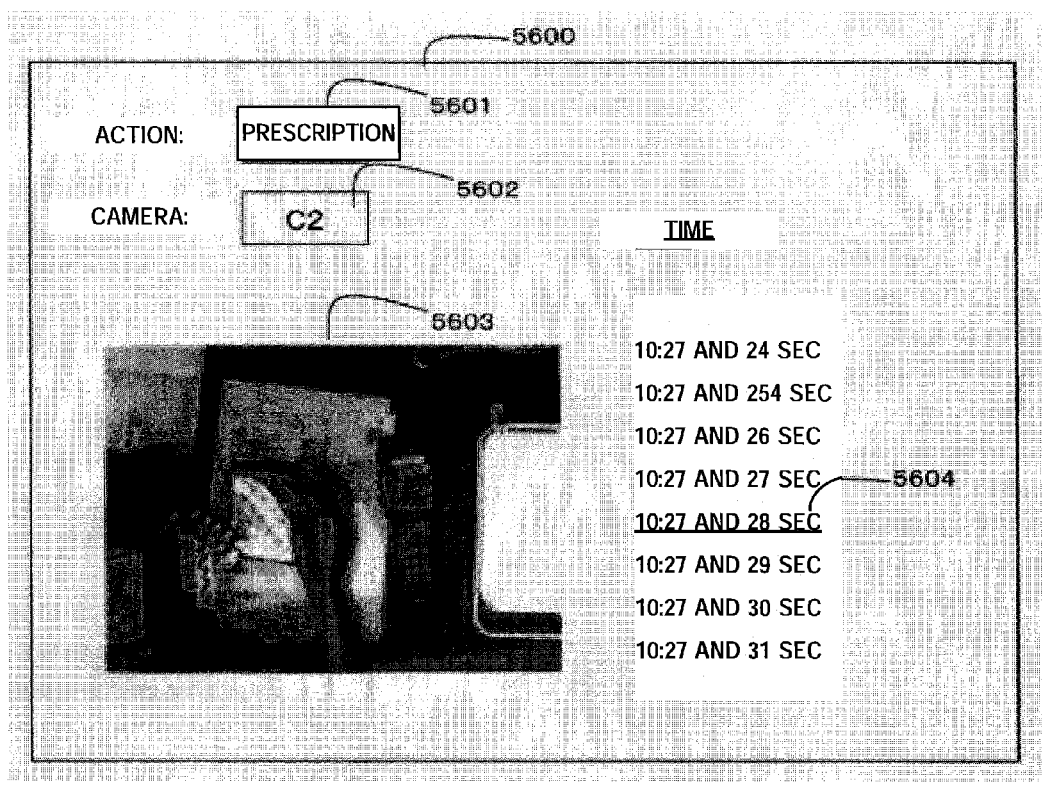
FIG. 56 is a diagram showing a screen on which is displayed the information data shown in an image region in FIG. 55.

FIG. 54-56 is an example of the display screen of the retrieval results. The display of the retrieval results relating to the present invention may be appropriately changed corresponding to the properties of the task of the monitoring object.

In FIG. 54, the display image 5400 is the screen initially displayed after calling out the monitoring data. The prescription ID of retrieved monitoring data is displayed in image region 5401. Here, the unique ID of the displayed "10000000k 1" is activated by the entered RFID tag, and the monitoring data 5402 and 5403 relating to the photographed task sequence/groups "J 1" and "G 1" are called out, and caption displayed. The display relating to each monitoring data is HTML text, and by adding the appropriate action of clicking and the like, the monitoring data of the desired group can be displayed in detail. The task, location, (terminal 1 of the camera ID) and date and time of the commencement of photography is list displayed as a caption, and with each display, by adding an appropriate action of clicking and the like recorded in HTML text, captioned monitoring data can be displayed.

FIG. 55 is a detailed displayed screen of the monitoring data grouped in "G 1" shown in the image region 5403 in FIG. 54. The operation, location (camera terminal ID), photography commencement date/time are list displayed as captions, and each display, by adding an appropriate action of clicking and the like, can display captioned monitoring data in HTML text.

FIG. 56 shows a screen which displays the monitoring data shown by the image region 5502 in FIG. 55. The action of the monitoring object is the "prescription" displayed by image region 5601, and the camera terminal ID is the "C 2" displayed by the image region 5602. C 2 is a terminal ID showing the monitoring camera of the prescription location. The image region 5603 is the image at the time shown in 5604. Here, the list displayed "time" is HTML text, and by adding the appropriate action of clicking and the like, the image of a specific time can be displayed.

Figure 57:
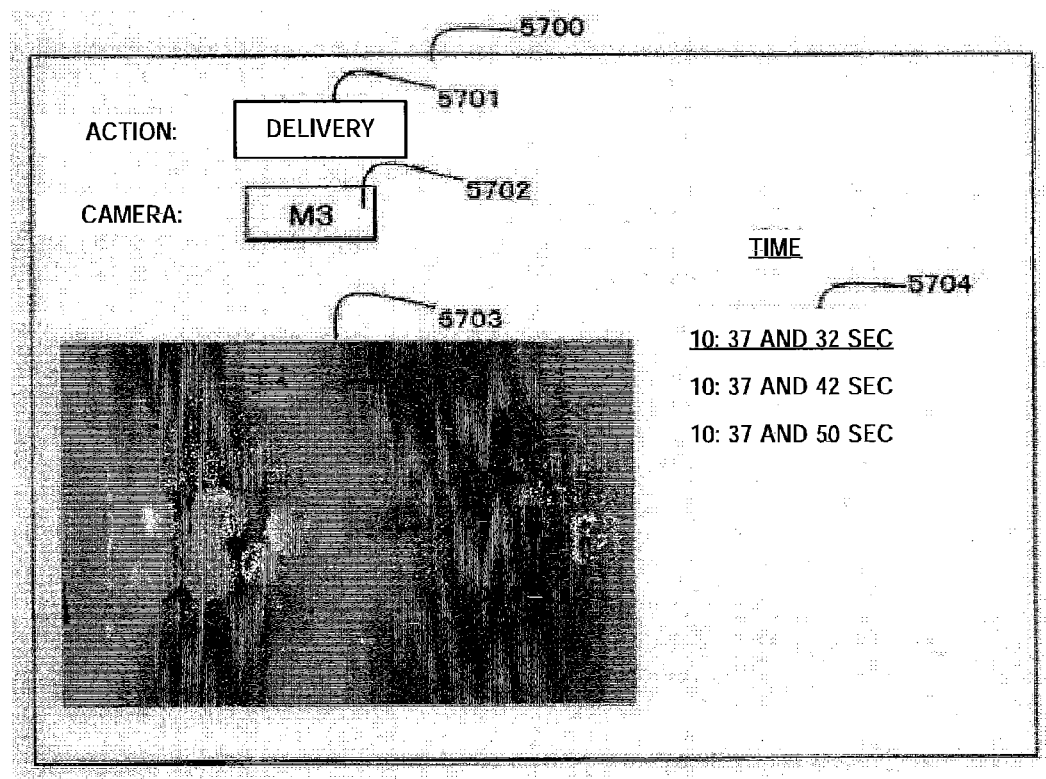
FIG. 57 is a diagram showing a screen on which is displayed monitoring data shown in the image region in FIG. 55.

FIG. 57 shows a screen on which is displayed the monitoring data shown by the image region 5503 in FIG. 55. The action of the monitoring object is the "delivery" displayed by image region 5701, and the camera terminal ID is "M 3" shown by image region 5702. M 3 is a terminal ID showing the magnifying glass of the delivery location. The image region 5703 is a magnified image monitored by the operator at the time shown in 5704. Here, the list displayed "time" is HTML text, and by adding the appropriate action of clicking and the like, a magnified image of the specific time can be displayed.

Embodiment 4

(Member Card Format)

Figure 58:
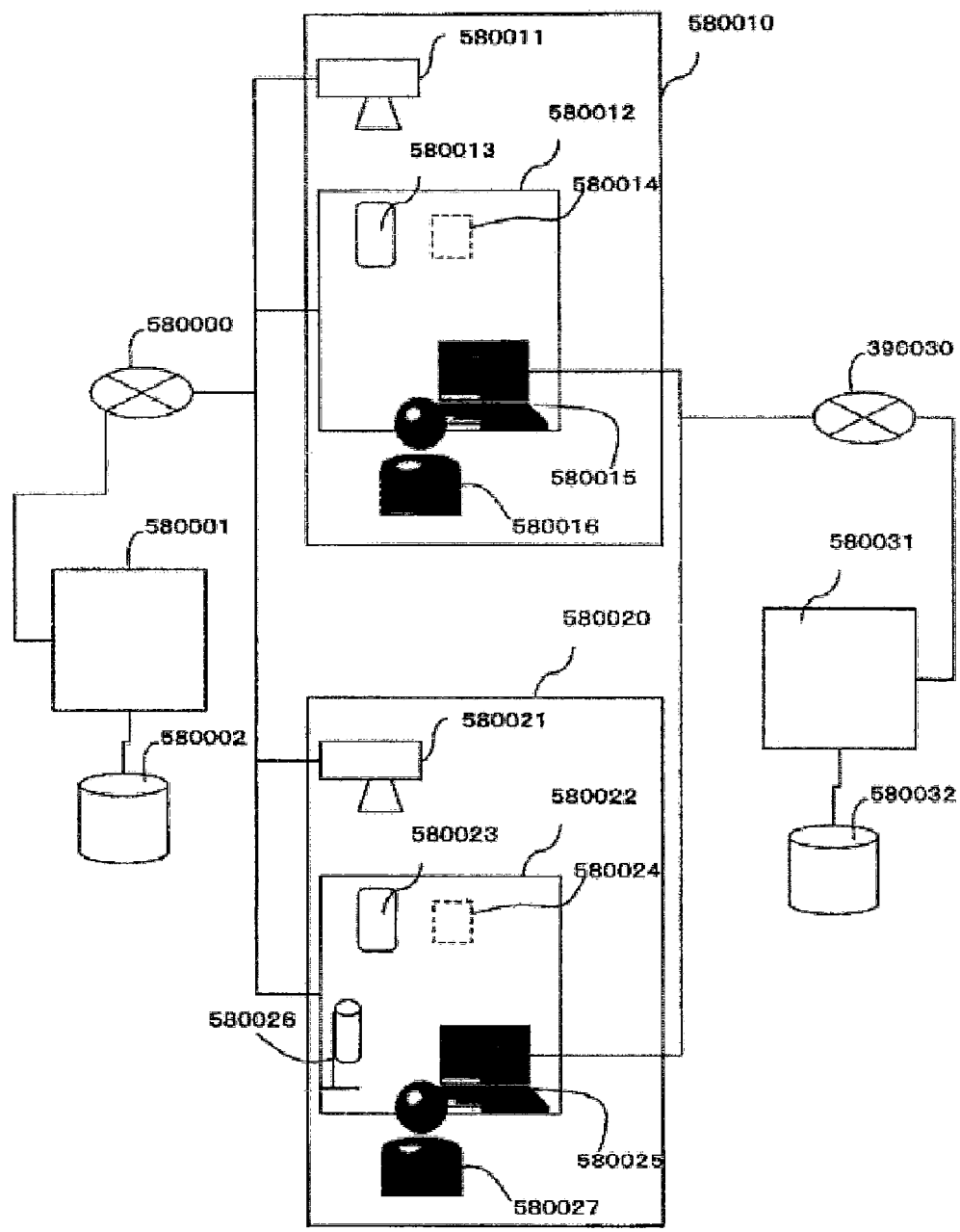
FIG. 58 is a summary composition diagram of a monitoring system relating to embodiment 4.

Next, an explanation is provided concerning the monitoring system relating to Embodiment 4 of the present invention. FIG. 58 is a summary composition diagram of the monitoring system relating to Embodiment 4 of the present invention. This is an embodiment form in the case of introducing reception, prescription location, delivery location, and accounting in a pharmacy. The monitoring system is composed from a network 580000, a monitoring system server 580001, a monitoring data storage device 580002, a first type of work area 580010, a second type of work area 580020, a network 580030, a task system server 580031, and a task data storage device 580032 where tasks are performed relating to the monitoring object, Here, 2 convenient networks 580000 and 580030 are shown in the drawing; however, these are composed of one network and a mutually connected substantially single network.

In addition, here, the explained convenient two types of work areas are shown one at a time, and are adopted in the reception location and in accounting. Since the second type of work area 580020 is adopted in the prescription location and the delivery location, these respective work areas total 4 work areas, shown 2 at a time. Furthermore, the work areas of the present invention are not limited to each type being handled two at a time, but may be composed by appropriately selecting a composition of one or two types of work areas corresponding to the introduction of the pharmacy, the scale of the task, or the number of work areas, and one type of work area alone may also receive multiple activities.

The composition of the first type of work area is as follows. A monitoring camera 580011 and a workbench 580012 are set to photograph tasks while the operator is facing the workbench. On the workbench 580012 is provided an RFID reader 580013 which manages the monitoring system server via the network. Upon arranging a document holder 580014 which holds a membership card fitted with an RFID chip in the detection area, a specific trigger signal is transmitted. The operator 580016 performs tasks relating to compounding, and performs task entry to the personal computer terminal 580015 connected to the task system server via the network.

The composition of the second type of work area is as follows. Arranging a monitoring camera 580021 and a workbench 580022, the operator 580027 uses the monitoring camera 580021 to photograph tasks while facing the workbench. Here, on the workbench 580022 is provided an RFID reader 580023 and a magnifying glass 580026. Upon arranging a document holder 580024 which holds a member card fitted with an RFID chip in the detection area of the RFID, a specific trigger signal is transmitted. The magnifying glass 580026 is connected to the network, and the operator sets the subject object in the photographic range of the magnifying glass, or faces the magnifying glass toward the subject object, and by operating a switch (not shown in the drawing), a magnified image can be acquired. Here, the magnified image can be used to confirm the task object by the operator, using a monitor (not shown in the drawing), along with transmitting it to the monitoring system server via the network. In addition, the operator 580027 performs compounding tasks, and inputs tasks to the personal computer terminal 580025 connected to the task system server.

Here, although not exclusively shown because of the simplification of the drawing, the monitoring system server 580001 and task system server 580031 are connected to the network, and are capable of mutual access.

Furthermore, the composition of the system shown here is nothing more than an example, and the established object and composition can be appropriately composed corresponding to the specific hardware. For example, task input is made to a personal computer terminal; however, the task input of the present invention is not limited to this. It is possible for a dedicated terminal and the like to be made corresponding to the scale of the pharmacy.

In addition, the action of each functional "unit" of the monitoring system server or task system server in the following explanation may be executed by a personal computer or the computer of a workstation or the like using a program prepared in advance, and the interface of a monitor, keyboard, and mouse and the like, realized by controlling each type of device. In addition, these programs are recorded on a storage medium readable by a computer comprising a hard disk, USB memory, CD-ROM, MO, and DVD and the like, and executed by the operation of the system user.

Figure 59:
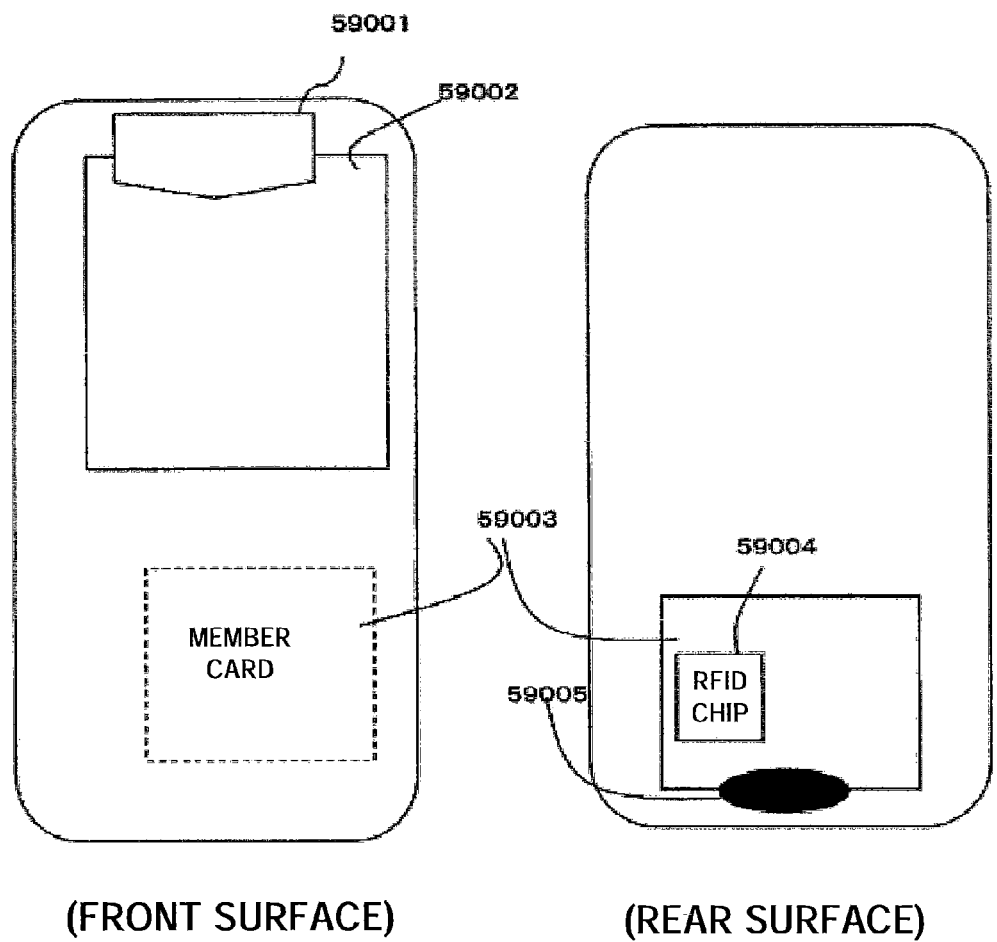
FIG. 59 is a diagram showing the composition of the document holder.

FIG. 59 is a diagram showing the composition of the document holder 580014 and 580024 used by the present invention. One of the document holders 580014 and 580024 is prepared relative to a single task, and holds the document of the task manual or the like on which is recorded the actions relating to the task, and accompanying the progression of the task is carried to each work area. The operator in the specific position of the workbench, performs the task while referring to the indicated items held in the document holders 580014 and 580024. The document holders 580014 and 580024, for example, are composed of for example from a clip 59001 which holds the task instruction manual or the like, a task instruction manual 59002, a member card 590032 which is attached an RFID chip, an RFID chip 59004, and a holding unit 59005 which secures the member card to the document holder. The holding unit 59005 is able to adopt a format which provides a frame into which a clip is inserted or into which are cut grooves, or an appropriate format in which the operator can carry the holder without dropping. If the document holder is placed on the workbench, by means of the RFID reader 580013 and 580023 provided on the workbench, the RFID chip is detected. Detecting the progress of a task from the detected/non-detected pattern, a trigger signal activated by the monitoring camera is transmitted, and the image information of the task progress sequence is acquired. Monitoring camera control is already known, as recorded in Patent Literature 1.

In the workplace of a pharmacy or the like which introduces the monitoring system of the present invention, a member number, which is pre-published relative to clients, is stored which uniquely specifies the clients as data stored by the RFID chip.

In addition, a document holder is adopted as a member card holding unit, however, the document holder is not limited to this, and can be appropriately adopted by being provided with a holding unit capable of holding the member card along with providing it to the task.

Figure 60:
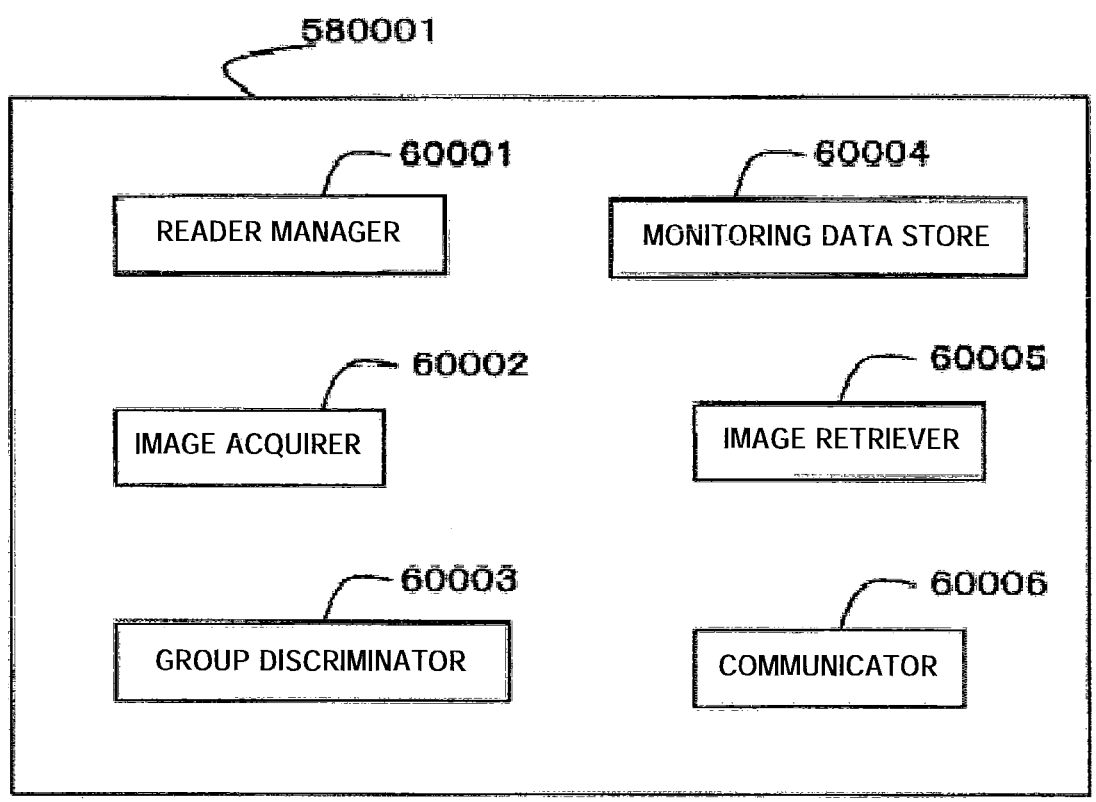
FIG. 60 is a diagram showing the internal composition of a monitoring system server.

FIG. 60 is a diagram showing the internal composition of the monitoring system server 580001 of the present invention. Monitoring system server 580001 is composed of a reader manager 60001 which manages the detection operation of the RFID reader, an image acquirer 60002 which acquires image information transmitted from the monitoring camera, and stores the generated/applied index information, a group discriminator 60003 which discriminates and groups task sequences/groups, a monitoring data store 6004 which stores monitoring data in a specific location, a monitoring data call out image retriever 60005 which receives the input of specific key information, and a communicator 60006 which controls the communication action of a network for the activity of each of the functional units.

Here, the monitoring data is composed from index information generated from the index information of a member number comprising the information read out from the detected RFID chip, date, time, and location of the monitoring information, and composed from image information from a monitoring camera. In the monitoring data, furthermore, depending upon whether acquisition is made within a specific effective time from the initial RFID chip detection, a specific group ID is assigned after discriminating if it belongs to a single task sequence/group, Here, monitoring camera terminal ID is adopted as the location of the monitoring camera, however, the location of the monitoring camera of the present invention is not limited to this, and may also, for example, be the RFID reader terminal ID which transmits a trigger signal activating the monitoring camera.

(Cooperative Action of Each Function Unit in A monitoring System Server)

Figure 61:
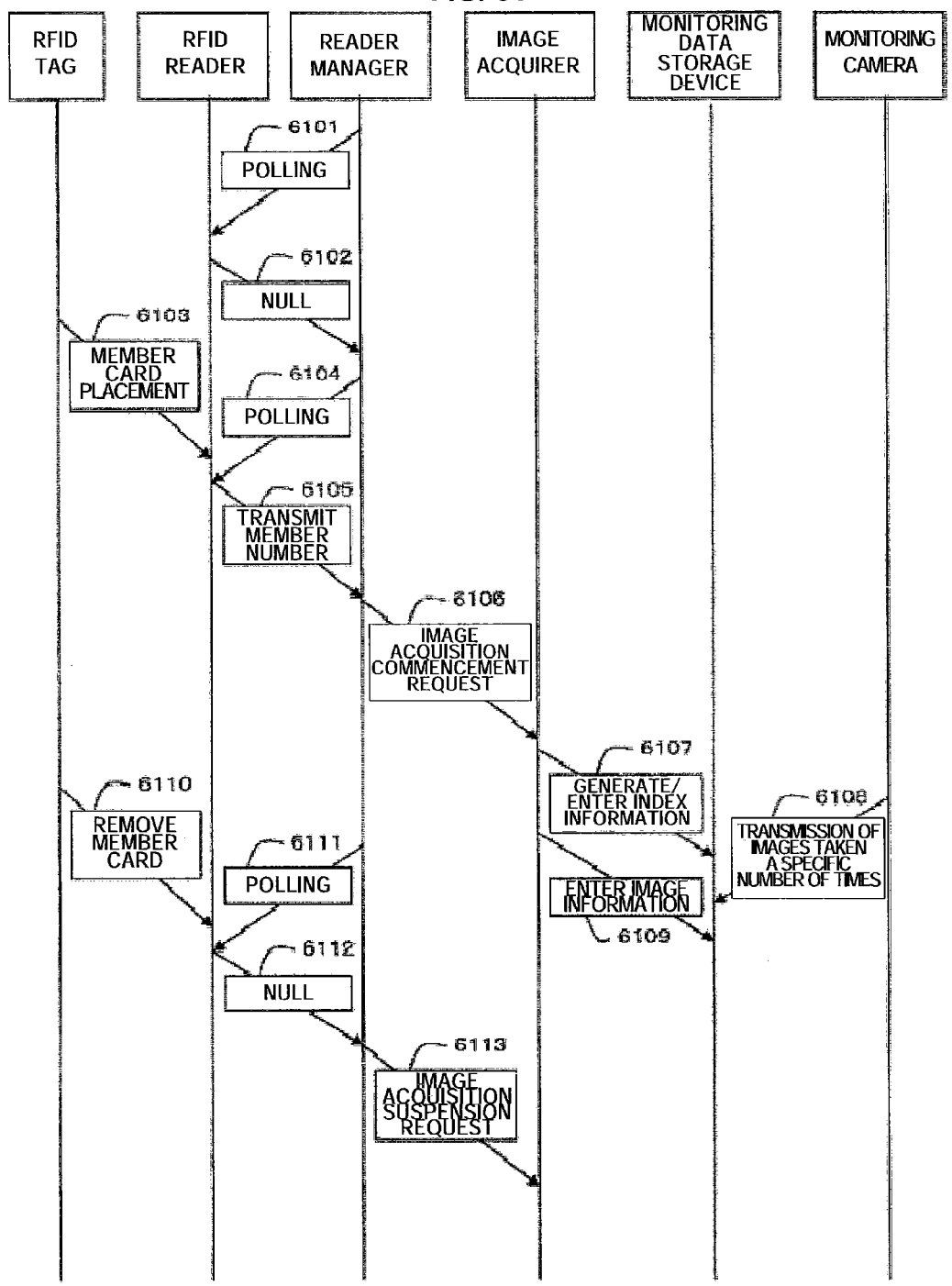
FIG. 61 is a sequence diagram showing the corporative operation stored in a monitoring data storage device.

FIG. 61 is a sequence diagram of the cooperative activity by each function unit/device of the reader manager and the like which shows image acquisition, generation of monitoring data, and action stored in the monitoring data storage device 580002.

In step 6101, polling is performed relative to the RFID reader by the action of the reader manager which executes a specific link control program. Here, if there is no translation request, then in step 6102, a "Null" signal is returned. In step 6103, upon placing the member card in a specific detection range, then, relative to the polling of step 6104, transmission is accomplished of the member number of step 6105. The member number is the number which specifies the clients stored in the RFID chip memory as indicated above.

The reader manager which received the member signal, in step 6106, requests image acquisition relative to the image acquirer. The image acquirer, in step 6107, generates index information, and writes it to the monitoring data storage device. An explanation concerning the generation of the index information is described hereafter.

In addition, the monitoring camera, in step 6108, transmits the image information of specific time units to the monitoring data storage device. In step 6109, the image acquirer enters index information to the storage location of the monitoring data which had entered the index information of the previous step.

In addition, in step 6110, if the member card is removed from within the specific detection parameters, then in step 6112, "Null" is returned relative to the polling of step 6111. The reader manager for which "Null" has been returned, in step 6113, sends a request for the termination of image acquisition relative to the image acquirer.

(Generation of Index Information)

Figure 62:
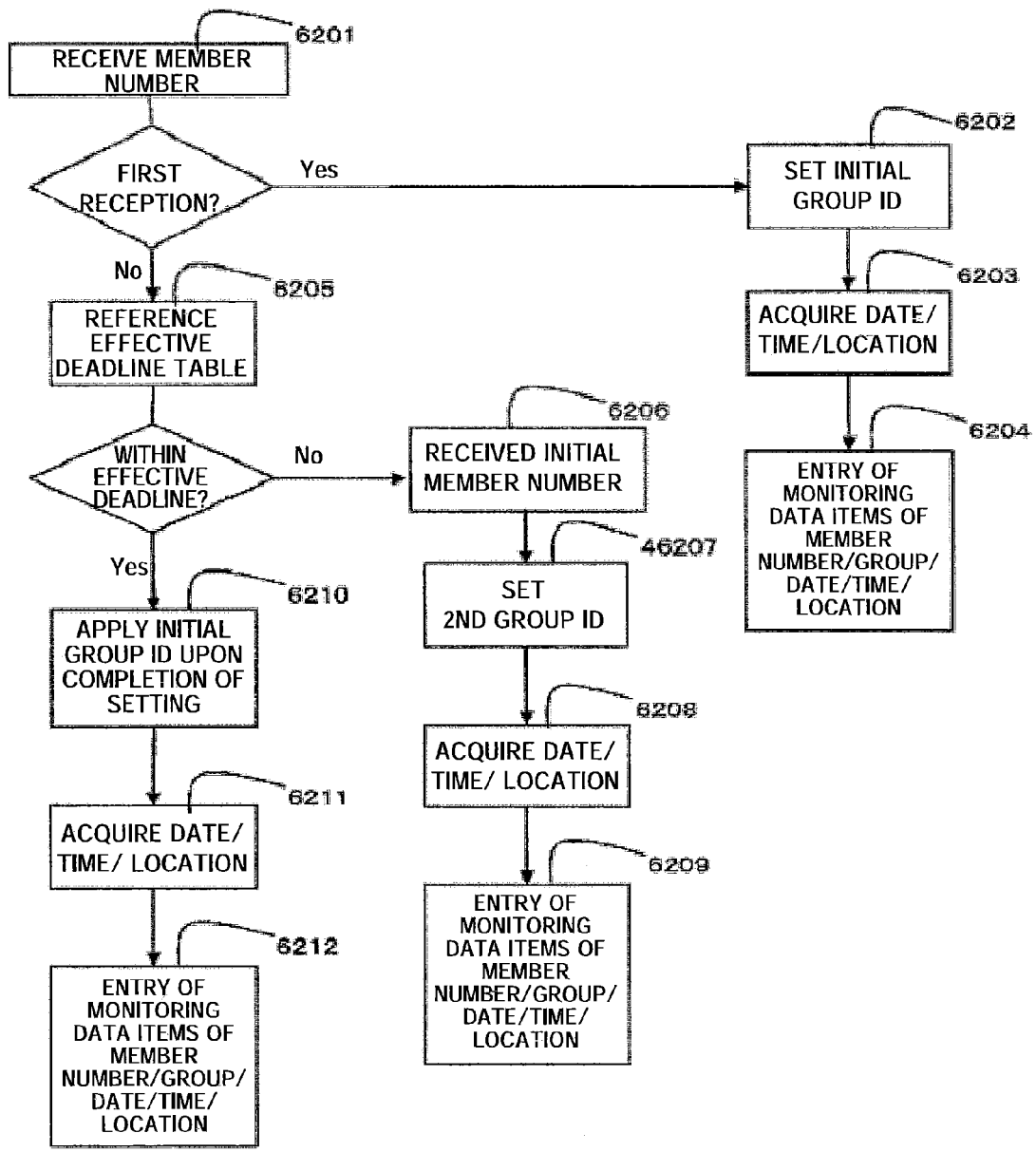
FIG. 62 is a flowchart which explains the operation of generation/entry of index information.

FIG. 62 is a flowchart which explains the action of the generation/entry of index information in step 6107 of FIG. 61.

First of all, in step 6201, the image acquirer receives the member number transmitted from the reader manager. Also, the image acquirer introduces the image data member number held relative to the monitoring data storage device monitoring data as index information, and discriminates whether it is an initial reception.

If the results of discrimination are "Yes", in other words, if it is initial reception, then in step 6202, the image acquirer sets the initial group ID. Next, in step 6203, the image acquirer acquires information of date, time, and location relating to the detection of the member number. Here, information of location is the monitoring camera terminal ID, and the work area can be specific by this terminal ID.

Furthermore, here, the monitoring camera terminal ID is adopted as the location of the monitoring camera, however, the location of the monitoring camera of the present invention is not limited to this, and, for example, it may also be the terminal ID of the RFID reader which transmits a trigger signal to activate the monitoring camera.

Also, in step 6204, the image acquirer enters the set or acquired group ID, date, time, location and member number to each item corresponding to the pre-established monitoring data.

If the discrimination result is "No", in other words if the task sequence/group has already been set as the member number relating to the monitoring data, then in step 6205, the image acquirer refers to a specific effective deadline table. Also, if within the effective deadline, the image acquirer, in step 6206 performs the initial member number reception, and in step 6207 image acquirer sets a second group ID which is different from the already sent group ID. In other words, in step 6208, the image acquirer acquires information of date, time, and location relating to the detection of the member number. Also, in step 6209 the image acquirer enters the set or acquired group ID, date, time, location and member number to each item corresponding to the pre-set monitoring data.

In step 6205, if in referring to the specific effective deadline table, it is within the effective deadline, then in step 6210, the image acquirer applies the already established initial group ID. Next, in step 6211, the image acquirer acquires information of date, time, and location relating to the detection of the member number. Also, in step 6212, the image acquirer enters the applied or acquired group ID, date, time, location and temporary ID to each item corresponding to the pre-established monitoring ID.

Here, the group ID is set, and a format is adopted which sets the group items in each monitoring data. However, the invention relating to the task sequence/group of the present invention is not limited to this format, and a format may also be established for managing a group in which, without setting the data items relating to the group in the monitoring data, the monitoring data belonging to the same task sequence/group is registered in the management table established for each group.

Figure 63:
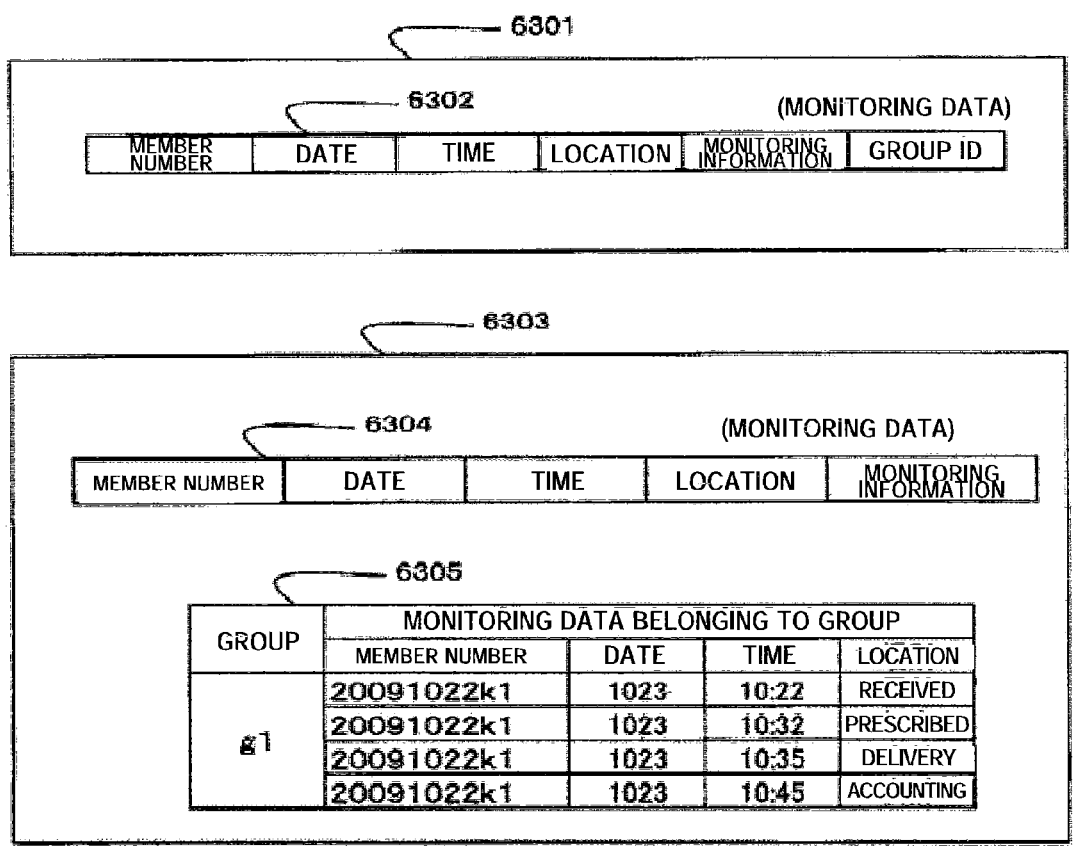
FIG. 63 is a summary diagram which compares grouped formats.

FIG. 63 is a summary diagram which compares the group formats. Here, in the items which showed the monitoring data 6302 stored in the monitoring data storage device 6301 relating to the format which established the group ID items in the monitoring data, and in the monitoring data storage device, shown are the monitoring data relating to the same task sequence registered in management table 6305 without attaching group ID items, and the monitoring data storage device stored in the monitoring data 6304 without attaching group ID items. Here, management table 6305 is in the format stored in the monitoring data storage device; however, the format relating to the present invention is not limited to this, and the management table may have a format stored in the memory of the monitoring system server or in an external storage device. In addition, monitoring information may be image information acquired by the monitoring camera or magnified images obtained from a magnifying glass.

(Effective Deadline Table)

FIG. 64 shows the composition of a referenced effective deadline table in step 6205 of FIG. 62. Here, there also cases which are effective for within three hours from the reception of an initial member number. The effective deadline table is a table in which an edition is made each time there is recognition of the "reception of an initial member number". Items of the effective deadline table are composed from the received member number, the date relating to initial reception, the time relating to initial reception, the effective deadline and the group ID. Referring to this table, with the image acquirer, the same group ID is assigned concerning monitoring data relating to the same member number within the effective deadline. Data shown in table 64001 and 64002 is the member number "20091022k1"; however concerning monitoring data of 6402 after passing the effective deadline of the task sequence of "g1" it is recognized as a different task sequence, and a second group ID "g8" is established which differs from the initial "g1".

Figure 65:
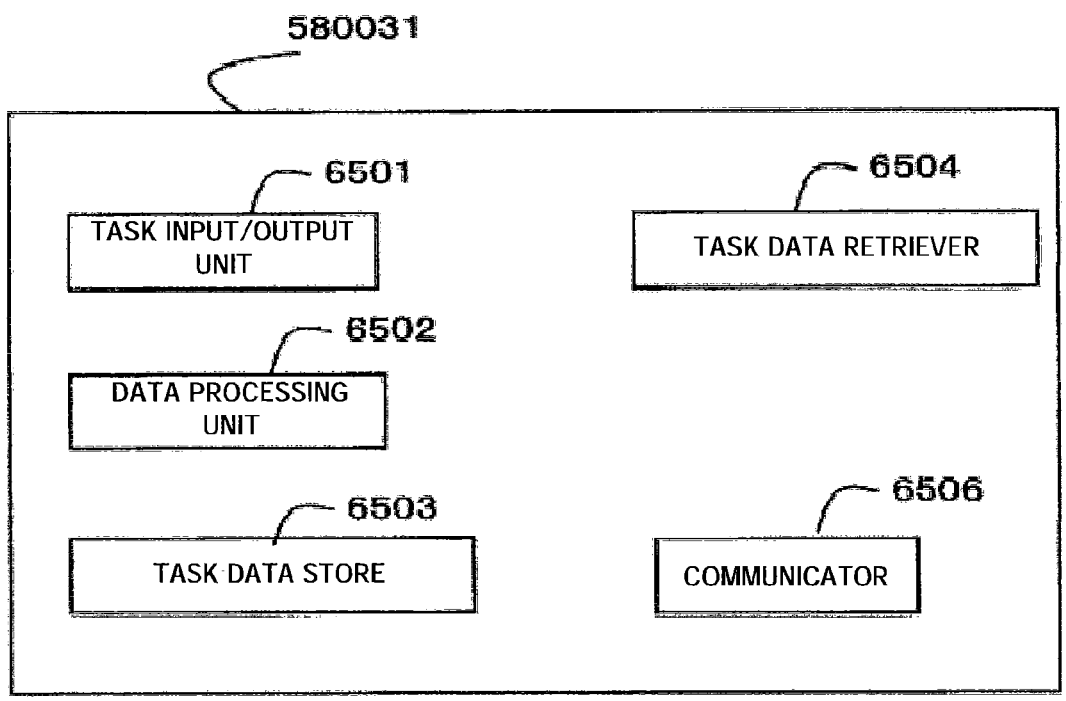
FIG. 65 is a diagram showing the internal composition of a task system server.

FIG. 65 is a diagram showing the internal composition of the task system server 580031 of the present invention. Task system server 580031 is composed from a task input/output unit 6501, data processing unit 6502 which adds task information of input tasks in the format of task data, task data storage 6503 which controls the storage of task data in the task data storage device 580032, task data retriever 6504 which controls retrieval of task data by specific key information input, and communicator 6505 which controls communications actions on the network for the actions of each of these functional units.

Figure 66:
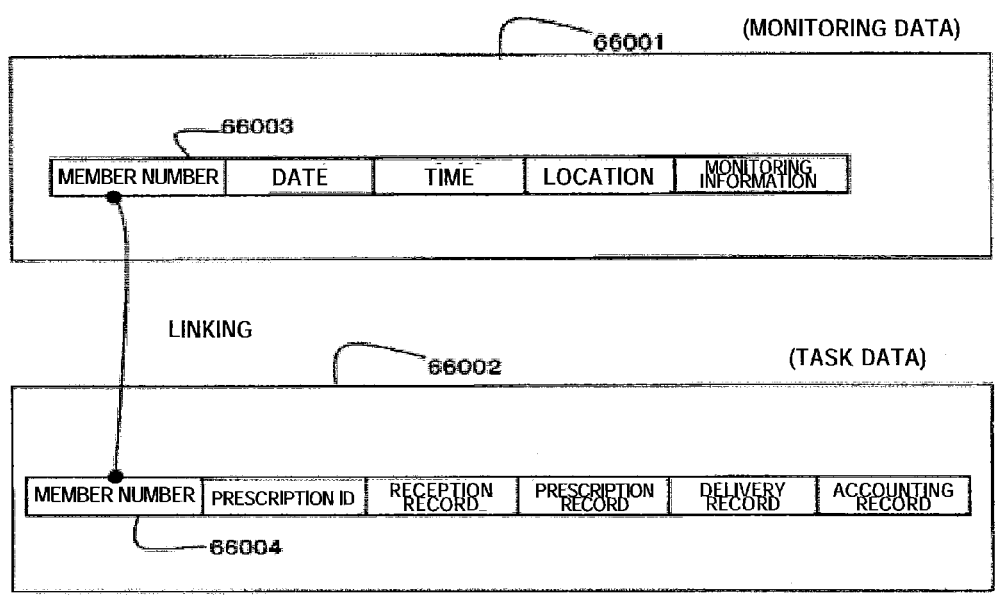
FIG. 66 is a diagram showing the composition of monitoring data and task data.

FIG. 66 is a diagram showing the composition of acquired generated monitoring data and task data. Monitoring data 566001 is composed from the data items of member number, date, time, location and monitoring information. Here, monitoring information is image information acquired by the monitoring camera. Task data 6002 is composed from the member number, prescription ID, reception record, prescription record, delivery record and accounting record. Here, the reception record summarily suggests items relating to monitoring information. Detailed specific items are established corresponding to the task need.

Here, member number 66003 comprising the data items of the monitoring data and the member number 66004 comprising the data items of the task data are the same, and are linked items. As the retrieval key for member number items of the task data, if the member numbers composed of the data items of the monitoring data are examined, the monitoring data of a task relating to the task data can be called out.

Conveniently, one monitoring data and task data are shown in the figure, however, data handled by the present invention is the bundling of multiple linked data.

Figure 67:
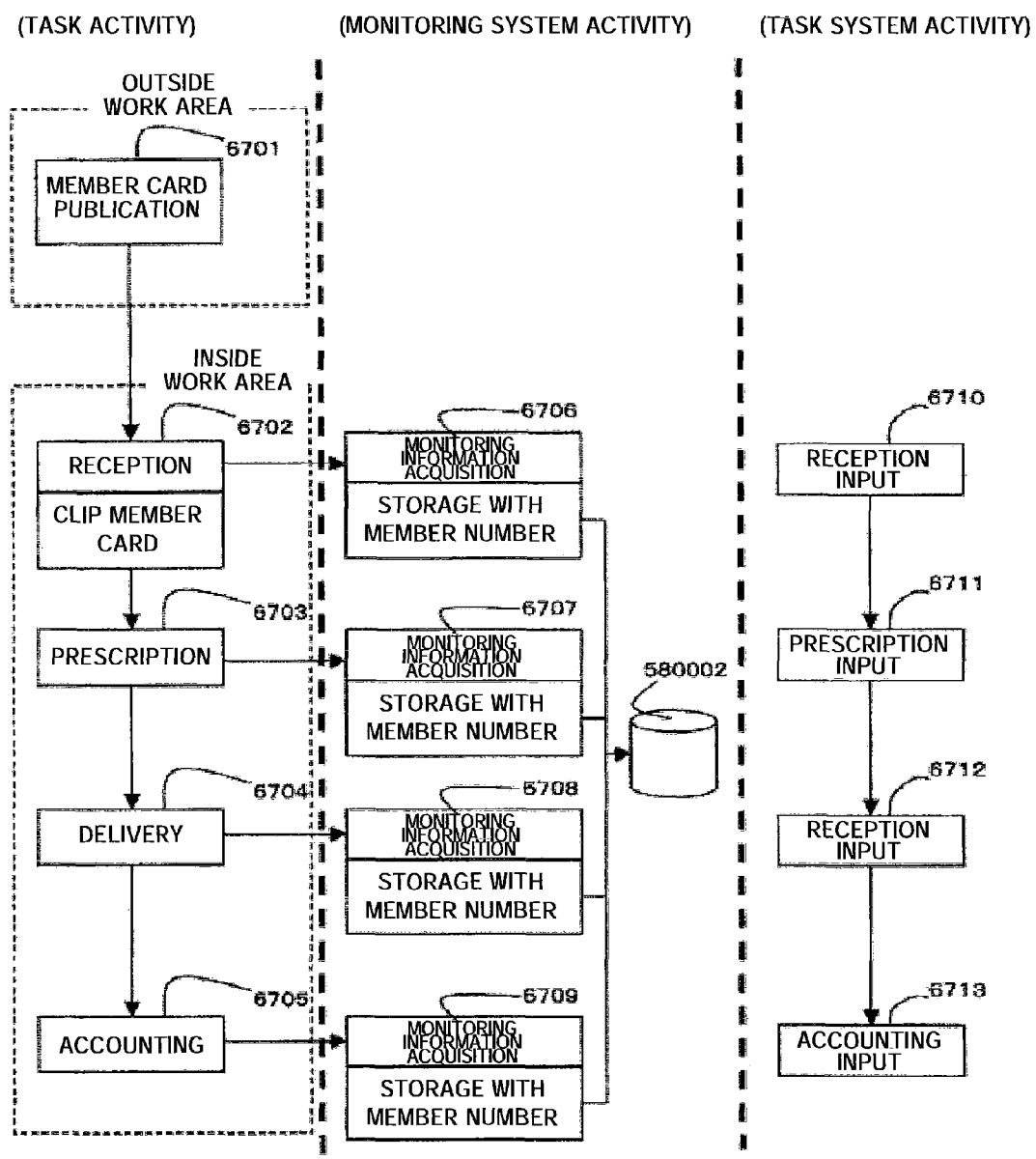
FIG. 67 is a sequence diagram showing the entire system operation of embodiment three.

FIG. 67 is a sequence diagram showing the activity of the entire system of embodiment 3. Here, the three activities of task performed within the work area and outside of the work area which is the object of monitoring, activity of the monitoring system relating to monitoring within the work area, and activity of the monitoring system are arranged in a chronological timeline.

First of all, in step 6701, preceding the initiation of a task, by inputting individual information and the like of the clients of the pharmacy comprising the workplace in which the present invention is introduced, allocating a member number to the clients, and registering them in a task data storage device from the task system server, and a member card to which an RFID chip is affixed which stores the member number is published.

An explanation is provided of both the monitoring system server and task system server corresponding to a chronological timeline. Furthermore, a monitoring camera, operator and personal computer terminal, use the same type of writing, as convenient with regard to the location of the same type of work area composition, and are no more than equal in terms of the compositional elements of the system or as monitoring objects.

Step 6702 is a reception step. In the reception location, adoption is made of the composition of the first type of work area 580010 shown in FIG. 58. At this time, the action of the task system server, in step 6710, receives input, and the receiver, acting as the operator, performs reception relative to patients and the like coming to the office, and performs reception input from a personal computer terminal.

At this time, the monitoring system server, in monitoring information acquisition step 6706, acquires image information of tasks photographed by the monitoring camera 580011. Index information is generated which includes a member number, and monitoring data is generated by adding the index information to the image information. Also, the monitoring system server discriminates task sequence/groups, and then stores them in a specific location of the monitoring data storage device 580002.

Step 6702 is a prescription step. Here, shown in FIG. 58, is the composition of a second type of work area 580020 provided with a magnifying glass 580026. The activity of the task system server at this time, in step 6711, receives the prescription input, and the pharmacist, acting as the operator, provides prescriptions relative to the patients and the like, as recorded in the manual, and performs prescription input from a personal computer terminal.

At this time, the monitoring system server, in the monitoring information acquisition step 707, acquires image information of tasks photographed by the monitoring camera 580021, and generates index information including the member number, and monitoring data is generated by adding index information to image information. Also, the monitoring system server discriminates task sequence/group, and records them in a specific location of the monitoring data storage device 580002.

Here, the operator, when making a detailed monitoring of the task object, acquires a magnified image by operating a magnifying glass 580026. The acquired magnified image is transmitted to the monitoring system server, and by executing a specific program which processes an image from the magnifying glass attached to the image acquirer, index information is added relating to the RFID chip during detection, and is stored as monitoring data in a specific location of the monitoring data storage device 580002.

Figure 68:
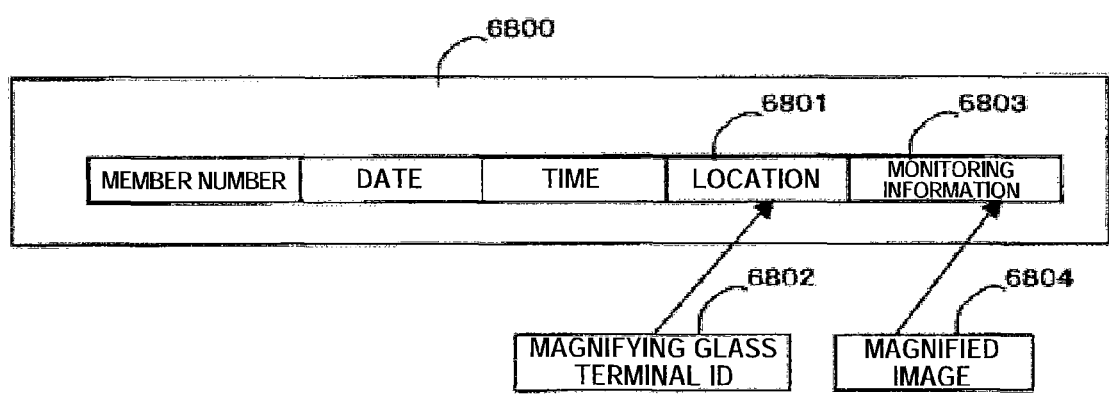
FIG. 68 is a diagram showing the composition of monitoring data relating to a magnified image.

FIG. 68 shows the composition of monitoring data relating to a magnified image. The monitoring data 6800 relating to the magnified image composed from data items of member number, date, time, location and monitoring information is the same as the monitoring data relating to the image information obtained from the monitoring camera. Here, the terminal ID 6802 of the magnifying glass is entered in location 6801, and the magnified image 6804 is stored in the monitoring information 6803. The storage/retrieval of monitoring data is executed by the same action as the monitoring data relating to the image of the monitoring camera. In addition, the discrimination of the task sequence/group is the same, and the group ID may also be set as a data item of the monitoring data, corresponding to the need.

Step 6704 is a delivery step. Here, FIG. 58 shows the composition of the second type of work area 580020 provided with a magnifying glass 580026. The action of the task system at this time, in step 6712, receives input, and the deliverer, acting as the operator, performs the delivery function toward patients and the like coming to the pharmacy, and provides delivery input from a personal computer terminal.

At this time, the monitoring system server, in monitoring information acquisition step 6708, acquires image information of tasks photographed by the monitoring camera 580021, and generates index information including a membership number, and monitoring data is generated by adding index information to the image information. Also, the monitoring system server discriminates task sequence/group and stores them in a specific location of the monitoring data storage device 580002.

Here, when the operator makes a detailed monitoring of the task object, a magnifying glass 580026 is operated, and a magnified image is acquired. The acquired magnified image is transmitted to the monitoring system server, and by executing a specific program which processes an image from the magnifying glass attached to the image acquirer, index information relating to the RFID chip is added during detection, and is stored as monitoring data in a specific location of the monitoring data storage device 58002.

Step 6705 is an accounting step. In the accounting location, the composition is adopted of the first type of work area 580010 shown in FIG. 58. The activity of the task system at this time, in step 6713, receives accounting input, and the accounting responsible supervisor, as the operator, performs accounting tasks relative to patients who come to the pharmacy, and provides accounting input from the personal computer terminal.

At this time, the monitoring system server, in monitoring information acquisition step 6709, acquires image information of tasks photographed by the monitoring camera 580011, generates index information including member number, and generates monitoring data by adding index information to the image information. Also, the monitoring server discriminates the task sequence/group, and stores it in a specific location of the monitoring data storage device 580002.

(Tracking)

Figure 69:
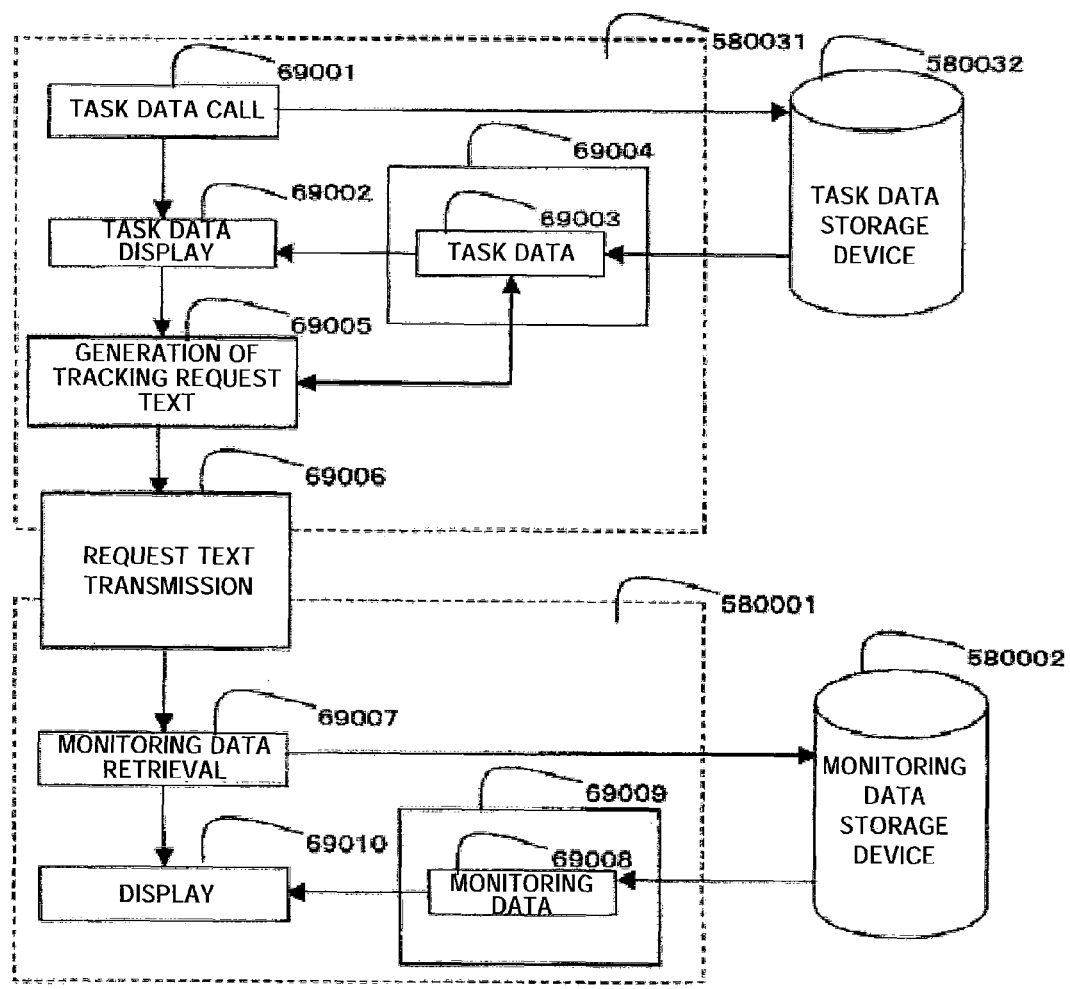
FIG. 69 is a flowchart showing the operation in the case of performing tracking.

FIG. 69 is a flowchart which generates problems relative to tasks relating to the task data being handled by the task system, and shows the action of the case of tracking for the purpose of confirmation.

Here, the action of the step of the region 580031 shown by the broken line is the action of the monitoring server. An addition, the action of the region 580001 shown by the broken line is an action of the monitoring system server.

In step 69001, task system server patient names and the like are called out from desired task data relative to task data storage device 580032 in a known key input format. The object task data 69003 is developed in work region 69004 maintained in the memory (not shown in the drawing) of the task system server, and is data that can be processed in real-time, and in step 69002, is displayed in a specific format on and un-shown monitor or the like.

Next, in step 69005, the task system server generates tracking request text which includes the member number comprising the retrieval key essential to retrieving monitoring data from the data items of task data developed in the work region. Also, in step 69006, the generated request text is sent to the monitoring system server.

In step 69007, the retrieval key is extracted from the request text received by the monitoring system server, and the monitoring data is retrieved. The retrieval key indicates the data item and its item value in a format such as that indicated below.

This indicates the value of the data item and key examined in the format of (Data item, item value) equals (member number, member number value)

In step 69010, the monitoring system server displays monitoring data 69008 retrieved, called out, and developed in work region 69009 of the memory (not shown in the drawing) of the monitoring system server. Here, the called out monitoring data conveniently records one data shown in the diagram; however, all belong to the same task sequence/group. Since each monitoring data sets the group ID and is group managed, call out and display can be performed for each group. In this manner, a link is formed so that monitoring data can be directly called out from the task data, with the result of realizing a high degree of traceability.

FIG. 70-73 is an example of a display screen of the retrieval results. The display of the retrieval results relating to the present invention can be appropriately changed corresponding to the nature of the task of the monitoring object.

In FIG. 70, display image 7000 is an image initially displayed after calling out the monitoring data. The member number of the retrieved monitoring data is displayed in image region 7001. Here, the displayed member number "20091022k1" is activated by the RFID chip, in which the member number had been entered, and the monitoring data 7002 and 7003 relating to the photographed task sequence/group "G 8" "G 1" is called out and selectively displayed. The display relating to each monitoring data is an HTML text, and by adding the appropriate action of a click and the line, the monitoring date of a desired group can be displayed in detail.

FIG. 71 is a detailed display screen of the monitoring data group in "G1" shown by the image region 7003 in FIG. 70. The operation, location (camera terminal ID), of the camera is list displayed with the date and time of the commencement of photography as a heading, and each display, by adding the appropriate action of clicking or the like recorded in the HTML text, the monitoring data can be selectively displayed.

Figure 72:
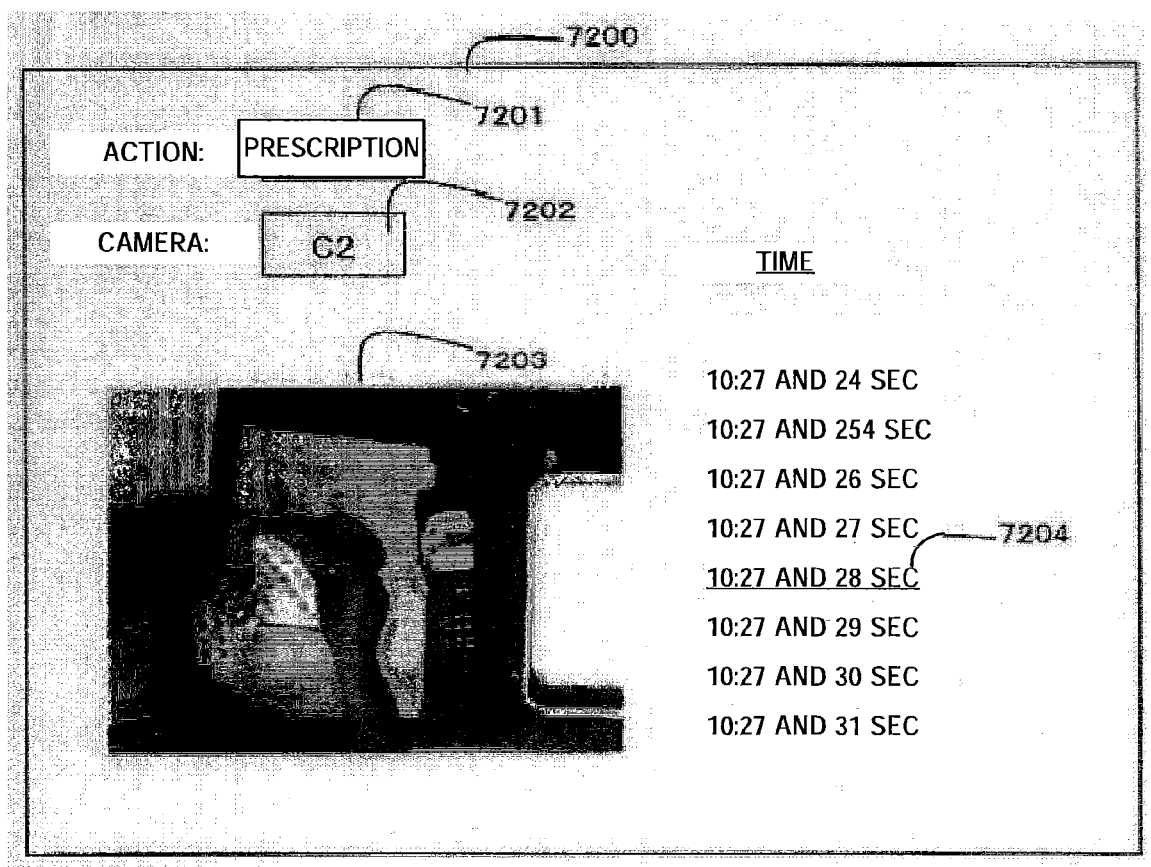
FIG. 72 is a diagram showing a screen on which is displayed the information data shown in the image region in FIG. 71.

FIG. 72 shows a screen which displays the monitoring data shown in the image region 7102 in FIG. 71. The action of the monitoring object is the "prescription" displayed in the image region 7201, and the camera terminal ID is the "C 2" shown in the image region 7202. C 2 is the terminal ID which shows the monitoring camera of the prescription location. The image region 7203 is an image of the time shown in 7204. Here, the list displayed "time" is HTML text, and by adding the appropriate action of a click or the like, an image of the desired time can be displayed.

Figure 73:
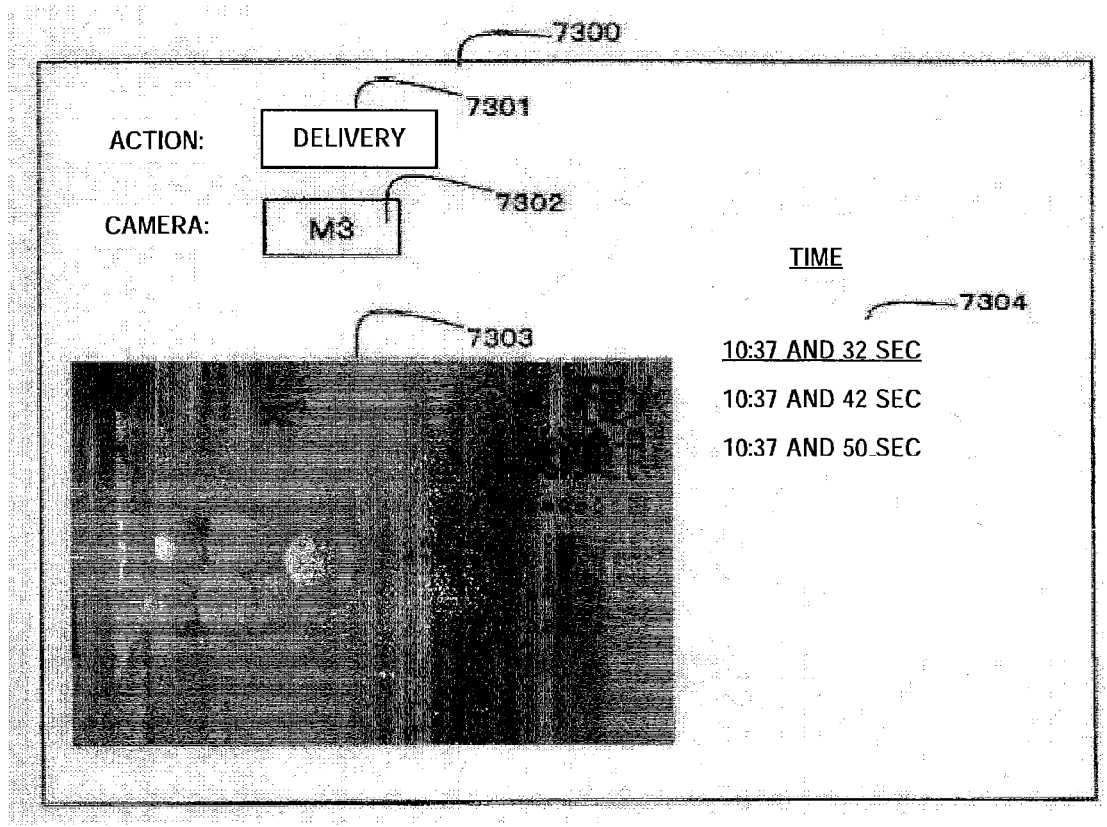
FIG. 73 is a diagram showing a screen on which is displayed the monitoring data shown in the image region in FIG. 71.

FIG. 73 shows a screen which displays the monitoring data shown in image region 7103. The action of the monitoring object is the "Delivery" displayed in the image region 7301. The camera terminal ID is "M3" shown in the image region 7302. M3 is a terminal ID which shows the magnifying glass of the delivery location. The image region 7303 is a magnified image monitored by the operator at the time shown in 7304. Here, the list displayed "time" is HTML text, and by adding the action of an appropriate click or the like, a magnified image of the desired time can be displayed.

The currently displayed embodiment form is an illustration of all of the points, and is not thought to be limiting. The parameters of the present invention are not limited to the above explanation, and are described by the Scope of Patent Claims, and it is intended that they include all of the changes within the meaning and scope equivalent to the Scope of Patent Claims.

INDUSTRIAL APPLICABILITY

In the system of the present invention which acts as explained in above Embodiments 1-4, since the index information of task data handled by the task and index information of the monitoring data managed by the task system are partially common to, and/or linked to the storage location, if task data relating to tasks for which tracking by the task system is desired is in the process of being handled, index information of task data being developed in the work region of the task system can be easily keyed, and the monitoring data can called out from the monitoring system.

As a result, high-speed traceability can be realized, and the monitoring system relating to the present invention can be coupled with various task systems and broadly used broad industrial sectors without being limited to the field of medical treatment.

In addition, in the known monitoring system of Patent Literature 1, a unique ID is allocated for initial task commencement, and along with the task flow, a relationship is established for recorded data relating to the unique ID. Immediately prior to or at the same time as the commencement of a task, an RFID tag needs to be set, and a unique ID stored. Owing to this, in order to resolve the problem of increasing the weight of the task burden without having enough time for reception and the like. Initially, by not specifying the task, the image information in the appropriately allocated "tag ID" was left hanging, and "after" the relative task burden had become lighter, and it could be made more specific (=by linking), the task group could specify the type of task. This resulted in dispersing the task burden, making use possible in various industrial monitoring systems.

LEGEND

10001 Monitoring system server
10010 First type of work area
10020 Second type of work area
10031 Task system server
10013 RFID reader
10023 RFID reader
10014 Document holder
10024 Document holder
10015 Personal computer terminal
10025 Personal computer terminal It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A monitoring system comprising:
at least one motion picture or still picture device, wherein:
(a) tasks for each of at least one work area is established so as to be provided within photographic parameters;
(b) connection is made to a network;
(c) a trigger signal is received which provides notification of the timing of a task;
(d) the progress of the task is continuously photographed;
(e) the photographed image information is transmitted to a specific transmission destination; and
(f) included as compositional elements are:
  (i) an RFID tag which is added to something supplied to the task;
  (ii) an RFID reader which transmits a trigger signal in a specific format to the photographic device connected to the network, and, the detection area of the RFID tag is set so as to detect an RFID tag which is located on the standard position that is assumed corresponding to the nature of the task accomplished in the work area, the detection area of the RFID tag is set so as to provide the position, and upon detecting the RFID tag, the tag ID which stores the RFID tag is read out, and the initial/termination timing of the task is extracted from a specific detection/non-detection pattern of the RFID tag; and
  (iii) a monitoring system server connected to the network, which receives the image information, and creates index information which at least includes the tag ID, stored as monitoring data related to the image information; a specific effective deadline being set from the point in time at which the tag ID is initially read out, and monitoring data which hold the same tag ID acquired within the effective deadline as index information are recognized as the task sequence group relating to a single task, and the monitoring data are retrieved for each group.

2. The monitoring system of claim 1, wherein:
(a) the tag ID stored in the RFID tag is a read-only fixed ID;
(b) the fixed ID in the input means attached to the task system performing input relating to the execution of the task is entered; and
(c) the monitoring data and task data are linked by adding the fixed ID to index information of the task data handled by the task system.

3. The monitoring system of claim 1, wherein the tag ID stored in the RFID tag is a read-only fixed ID, and upon inputting the fixed ID to the input means attached to the task system performing input relating to the execution of the task, and the monitoring data and task data are linked by adding the URI which shows the storage location of the task sequence/group which holds the fixed ID as index information.

4. The monitoring system of claim 1 wherein:
(a) written information corresponding to the tag ID stored in the RFID tag is displayed on items supplied to the task;
(b) a reference table is attached for calling out the corresponding tag ID from the display information; and
(c) by inputting written information transcribed to a ledger or prescription as a retrieval key, the monitoring data is retrieved.

5. The monitoring system of claim 1, wherein written information corresponding to the tag ID stored in the RFID tag is displayed on items supplied to the task, and a reference table is provided for reading out the corresponding tag ID from written information, and upon inputting the written information to an input means attached to the task system performing input relative to the execution of the task, by adding the URI which shows the storage location of the task sequence/group's monitoring data holding the tag ID corresponding to the written information as index information, to the index information of task data handled by the task system, the task data and monitoring data are linked.

6. The monitoring system of claim 1, wherein, prior to the commencement of a task, the temporary ID is entered to the RFID tag, and at the time of detection/entry by the RFID reader/writer attached to the task system after task commencement, a unique ID which has been allocated to each task is entered to the RFID tag, and index information which includes the temporary ID is rewritten to index information including the unique ID.

7. The monitoring system of claim 1, wherein the RFID tag is a component of a membership card storing the membership number, and index information including the membership number has a relationship established with the image information, and is stored in the monitoring system server as monitoring data, and by providing a reference table in which a relationship is established between the unique ID which the task system has pre-allocated to a task and the membership number, monitoring data is directly retrieved relating to a task from the task data while being handled by the task system connected to the monitoring system server.

8. The monitoring system of claim 6, wherein the unique ID is a prescription ID of a prescription relating to a task.

9. The monitoring system of claim 1, wherein items provided to a task are at least one selected from an operation indication sheet, a document holder, and a tray.

10. The monitoring system of claim 1, wherein the task system is selected, at a minimum, from among the group including the compounding system, reception system and accounting system which manages compounding tasks in a pharmacy.

11. The monitoring system of claim 2, wherein, when adding a fixed ID to the index information, by further adding the use frequency of the fixed ID, when retrieving monitoring data belonging to multiple task sequence/groups, relative to a single ID, in referencing the item value relating to the use frequency of the fixed ID in the task data and monitoring data, it is specified in the monitoring data of a single task sequence/group.

12. The monitoring system of claim 2, wherein, when calling out monitoring data linked by task data during handling, in the case of retrieving monitoring data belonging to multiple task sequence/groups relative to a single fixed ID included in the index information of task data, the monitoring data of the single task sequence/group is specified by referring to another data item.

13. The monitoring system of claim 2, wherein the input means is the RFID reader, and upon placing the RFID tag within detection parameters, the tag ID stored by the RFID tag is read out, and the action of linking the task data of a task being handled by the task system, with the monitoring data is executed.

14. The monitoring system of claim 4, wherein, in the case of retrieving monitoring data belonging to multiple task sequence/groups by inputting written information as a retrieval key, the monitoring data of a single task sequence/group is specified by referencing other data items.

15. The monitoring system of claim 1, wherein, the task data includes, as data items, the prescription ID, patient name, date of reception, time of reception and prescription content.

16. The monitoring system of claim 1, wherein the monitoring data includes, as data items, the tag ID, the date, time, location of photographic device, image information and task sequence/group ID.

17. The monitoring system of claim 1, wherein the monitoring data, attached to the work area or in the work area, includes magnified image information photographed by means of a magnifying glass and used for tasks, and receives the transmission of magnified image information, generates index information including the tag ID during detection in the work area, with a relationship being established with the magnified image information, which is then stored as monitoring data in the monitoring system server.

* * * * *